US009221845B2

(12) United States Patent
Cao

(10) Patent No.: US 9,221,845 B2
(45) Date of Patent: Dec. 29, 2015

(54) PROCESSES AND INTERMEDIATES FOR MAKING A JAK INHIBITOR

(71) Applicants: Incyte Corporation, Wilmington, DE (US); Incyte Holdings Corporation, Wilmington, DE (US)

(72) Inventor: Ganfeng Cao, Newark, DE (US)

(73) Assignees: Incyte Holdings Corporation, Wilmington, DE (US); Incyte Corporation, Wilmington, DE (US)

( * ) Notice: Subject to any disclaimer, the term of this patent is extended or adjusted under 35 U.S.C. 154(b) by 0 days.

(21) Appl. No.: 14/645,046

(22) Filed: Mar. 11, 2015

(65) Prior Publication Data

US 2015/0183805 A1 Jul. 2, 2015

Related U.S. Application Data

(62) Division of application No. 14/197,701, filed on Mar. 5, 2014, now Pat. No. 8,987,443.

(60) Provisional application No. 61/773,659, filed on Mar. 6, 2013.

(51) Int. Cl.

| | |
|---|---|
| ***C07D 487/04*** | (2006.01) |
| ***C07D 401/14*** | (2006.01) |
| ***C07F 5/04*** | (2006.01) |
| ***C07F 5/02*** | (2006.01) |

(52) U.S. Cl.

CPC ................ *C07F 5/04* (2013.01); *C07D 401/14* (2013.01); *C07D 487/04* (2013.01); *C07F 5/025* (2013.01)

(58) Field of Classification Search

USPC .................................... 544/280; 546/13, 193

See application file for complete search history.

(56) References Cited

U.S. PATENT DOCUMENTS

| | | | |
|---|---|---|---|
| 2,985,589 | A | 5/1961 | Broughton et al. |
| 3,832,460 | A | 8/1974 | Kosti |
| 4,402,832 | A | 9/1983 | Gerhold |
| 4,498,991 | A | 2/1985 | Oroskar |
| 4,512,984 | A | 4/1985 | Seufert et al. |
| 4,548,990 | A | 10/1985 | Mueller et al. |
| 4,814,477 | A | 3/1989 | Wijnberg et al. |
| 5,378,700 | A | 1/1995 | Sakuma et al. |
| 5,510,101 | A | 4/1996 | Stroppolo |
| 5,521,184 | A | 5/1996 | Zimmermann |
| 5,630,943 | A | 5/1997 | Grill |
| 5,795,909 | A | 8/1998 | Shashoua et al. |
| 5,856,326 | A | 1/1999 | Anthony |
| 5,919,779 | A | 7/1999 | Proudfoot et al. |
| 6,060,038 | A | 5/2000 | Burns |
| 6,075,056 | A | 6/2000 | Quigley, Jr. et al. |
| 6,136,198 | A | 10/2000 | Adam et al. |
| 6,217,895 | B1 | 4/2001 | Guo |
| 6,335,342 | B1 | 1/2002 | Longo et al. |
| 6,375,839 | B1 | 4/2002 | Adam et al. |
| 6,413,419 | B1 | 7/2002 | Adam et al. |
| 6,486,322 | B1 | 11/2002 | Longo et al. |
| 6,548,078 | B2 | 4/2003 | Guo |
| 6,569,443 | B1 | 5/2003 | Dawson |
| 6,579,882 | B2 | 6/2003 | Stewart et al. |
| 6,624,138 | B1 | 9/2003 | Sung et al. |
| 6,635,762 | B1 | 10/2003 | Blumenkopf et al. |
| 6,712,973 | B2 | 3/2004 | Adam et al. |
| 6,713,089 | B1 | 3/2004 | Bertelsen et al. |
| 6,852,727 | B2 | 2/2005 | Goulet et al. |
| 6,953,776 | B2 | 10/2005 | Di Napoli |
| 7,005,436 | B2 | 2/2006 | Lloyd et al. |
| 7,167,750 | B2 | 1/2007 | Knudson et al. |
| 7,265,108 | B2 | 9/2007 | Ozaki |
| 7,335,667 | B2 | 2/2008 | Rodgers et al. |
| 7,358,255 | B2 | 4/2008 | Nakamura |
| 7,517,870 | B2 | 4/2009 | Auricchio |
| 7,598,257 | B2 | 10/2009 | Rodgers et al. |
| 7,745,437 | B2 | 6/2010 | Ren et al. |
| 7,750,007 | B2 | 7/2010 | Bearss et al. |
| 7,834,022 | B2 | 11/2010 | Rodgers et al. |
| 8,053,433 | B2 | 11/2011 | Rodgers et al. |
| 8,158,616 | B2 | 4/2012 | Rodgers et al. |
| 8,309,718 | B2 | 11/2012 | Li et al. |
| 8,410,265 | B2 | 4/2013 | Zhou et al. |
| 8,415,362 | B2 | 4/2013 | Rodgers et al. |
| 8,420,629 | B2 | 4/2013 | Rodgers et al. |
| 8,445,488 | B2 | 5/2013 | Rodgers et al. |
| 8,486,902 | B2 | 7/2013 | Rodgers et al. |
| 8,513,270 | B2 | 8/2013 | Arvanitis et al. |
| 8,530,485 | B2 | 9/2013 | Rodgers et al. |

(Continued)

FOREIGN PATENT DOCUMENTS

| | | |
|---|---|---|
| DE | 30 36 390 | 5/1982 |
| EP | 0223420 | 5/1987 |

(Continued)

OTHER PUBLICATIONS

26th Annual JPMorgan Healthcare Conference presentation dated Jan. 8, 2008 (28 pages).

Abe, et al., Heterocycles, "Effective Methods for Introducing Some Aryl and Heteroaryl Substituent onto 1-Azaazulene Nuclei", 66, 229-240 (2005).

Abelson et al., "Alternate reference values for tear film break-up time in normal and dry eye populations, Lacrimal Gland, Tear Film, and Dry Eye Syndromes 3 Part B", Adv Exp Med Biol, 2002; 506:1121-1125.

(Continued)

*Primary Examiner* — Kristin Vajda

(74) *Attorney, Agent, or Firm* — Fish & Richardson P.C.

(57) ABSTRACT

This invention relates to processes and intermediates for making {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, useful in the treatment of diseases related to the activity of Janus kinases (JAK) including inflammatory disorders, autoimmune disorders, cancer, and other diseases.

30 Claims, No Drawings

(56) References Cited

U.S. PATENT DOCUMENTS

| | | | |
|---|---|---|---|
| 8,541,425 | B2 | 9/2013 | Rodgers et al. |
| 8,563,541 | B2 | 10/2013 | Arvanitis et al. |
| 8,604,043 | B2 | 12/2013 | Li et al. |
| 8,691,807 | B2 | 4/2014 | Yao et al. |
| 8,716,303 | B2 | 5/2014 | Rodgers et al. |
| 8,722,693 | B2 | 5/2014 | Rodgers et al. |
| 8,741,895 | B2 | 6/2014 | Rodgers et al. |
| 8,748,401 | B2 | 6/2014 | Rodgers et al. |
| 8,765,734 | B2 | 7/2014 | Huang et al. |
| 8,822,481 | B1 | 9/2014 | Rodgers et al. |
| 8,829,013 | B1 | 9/2014 | Rodgers et al. |
| 8,835,423 | B2 | 9/2014 | Arvanitis et al. |
| 8,841,318 | B2 | 9/2014 | Arvanitis et al. |
| 8,883,806 | B2 | 11/2014 | Zhou et al. |
| 8,889,697 | B2 | 11/2014 | Rodgers et al. |
| 8,933,085 | B2 | 1/2015 | Rodgers et al. |
| 8,933,086 | B2 | 1/2015 | Rodgers et al. |
| 8,946,245 | B2 | 2/2015 | Rodgers et al. |
| 2002/0111353 | A1 | 8/2002 | Ledeboer et al. |
| 2003/0064969 | A1 | 4/2003 | Bhagwat et al. |
| 2003/0100756 | A1 | 5/2003 | Adams et al. |
| 2003/0144309 | A1 | 7/2003 | Choon-Moon |
| 2003/0165576 | A1 | 9/2003 | Fujii et al. |
| 2004/0009222 | A1 | 1/2004 | Chou et al. |
| 2004/0009983 | A1 | 1/2004 | Cox et al. |
| 2004/0029857 | A1 | 2/2004 | Hale et al. |
| 2004/0077654 | A1 | 4/2004 | Bouillot |
| 2004/0198737 | A1 | 10/2004 | Cox et al. |
| 2004/0204404 | A1 | 10/2004 | Zelle |
| 2004/0214928 | A1 | 10/2004 | Aronov |
| 2004/0235862 | A1 | 11/2004 | Burns |
| 2005/0014966 | A1 | 1/2005 | Tabe |
| 2005/0054568 | A1 | 3/2005 | Ling |
| 2005/0153989 | A1 | 7/2005 | Grotzfeld et al. |
| 2006/0004010 | A1 | 1/2006 | Habashita et al. |
| 2006/0020011 | A1 | 1/2006 | Wu et al. |
| 2006/0079511 | A1 | 4/2006 | Liu et al. |
| 2006/0106020 | A1 | 5/2006 | Rodgers et al. |
| 2006/0106027 | A1 | 5/2006 | Furet et al. |
| 2006/0128803 | A1 | 6/2006 | Klimko |
| 2006/0135537 | A1 | 6/2006 | Knegtel et al. |
| 2006/0178393 | A1 | 8/2006 | Pitts |
| 2006/0183761 | A1 | 8/2006 | Ledeboer et al. |
| 2006/0183906 | A1 | 8/2006 | Rodgers et al. |
| 2006/0223864 | A1 | 10/2006 | Biju |
| 2006/0293311 | A1 | 12/2006 | Li et al. |
| 2007/0135461 | A1 | 6/2007 | Rodgers et al. |
| 2007/0135466 | A1 | 6/2007 | Ledeboer et al. |
| 2007/0149506 | A1 | 6/2007 | Arvanitis et al. |
| 2007/0149561 | A1 | 6/2007 | Dhanak et al. |
| 2007/0191364 | A1 | 8/2007 | Braun et al. |
| 2007/0191405 | A1 | 8/2007 | Noronha |
| 2007/0208053 | A1 | 9/2007 | Wang et al. |
| 2007/0259904 | A1 | 11/2007 | Noronha |
| 2008/0021026 | A1 | 1/2008 | Borchardt et al. |
| 2008/0085898 | A1 | 4/2008 | Lu |
| 2008/0096852 | A1 | 4/2008 | Yanni |
| 2008/0119496 | A1 | 5/2008 | Ohlmeyer |
| 2008/0161346 | A1 | 7/2008 | Cheng |
| 2008/0188500 | A1 | 8/2008 | Arvanitis et al. |
| 2008/0194468 | A1 | 8/2008 | Bodor |
| 2008/0207570 | A1 | 8/2008 | Segura-Orsoni |
| 2008/0207584 | A1 | 8/2008 | Habashita et al. |
| 2008/0280876 | A1 | 11/2008 | Hobson et al. |
| 2008/0312258 | A1 | 12/2008 | Rodgers et al. |
| 2008/0312259 | A1 | 12/2008 | Rodgers et al. |
| 2009/0018156 | A1 | 1/2009 | Tang et al. |
| 2009/0076070 | A1 | 3/2009 | Harada et al. |
| 2009/0088445 | A1 | 4/2009 | Ledeboer et al. |
| 2009/0131403 | A1 | 5/2009 | Kusuda |
| 2009/0181959 | A1 | 7/2009 | Rodgers et al. |
| 2009/0197869 | A1 | 8/2009 | Arvanitis et al. |
| 2009/0203637 | A1 | 8/2009 | Hocek et al. |
| 2009/0215766 | A1 | 8/2009 | Rodgers et al. |
| 2009/0221608 | A1 | 9/2009 | Cui et al. |
| 2009/0233903 | A1 | 9/2009 | Rodgers et al. |
| 2009/0318405 | A1 | 12/2009 | Li et al. |
| 2010/0022522 | A1 | 1/2010 | Rodgers et al. |
| 2010/0069381 | A1 | 3/2010 | Itoh et al. |
| 2010/0113416 | A1 | 5/2010 | Friedman et al. |
| 2010/0190981 | A1 | 7/2010 | Zhou et al. |
| 2010/0210627 | A1 | 8/2010 | Mao et al. |
| 2010/0298334 | A1 | 11/2010 | Rodgers et al. |
| 2010/0298355 | A1 | 11/2010 | Li et al. |
| 2011/0059951 | A1 | 3/2011 | Rodgers et al. |
| 2011/0082159 | A1 | 4/2011 | Rodgers et al. |
| 2011/0086810 | A1 | 4/2011 | Rodgers et al. |
| 2011/0086835 | A1 | 4/2011 | Rodgers et al. |
| 2011/0201593 | A1 | 8/2011 | Babu et al. |
| 2011/0207754 | A1 | 8/2011 | Li et al. |
| 2011/0223210 | A1 | 9/2011 | Rodgers et al. |
| 2011/0224157 | A1 | 9/2011 | Rodgers et al. |
| 2011/0224190 | A1 | 9/2011 | Huang et al. |
| 2011/0288107 | A1 | 11/2011 | Parikh et al. |
| 2012/0014989 | A1 | 1/2012 | Rodgers |
| 2012/0077798 | A1 | 3/2012 | Rodgers et al. |
| 2012/0149681 | A1 | 6/2012 | Rodgers |
| 2012/0149682 | A1 | 6/2012 | Rodgers et al. |
| 2012/0214825 | A1 | 8/2012 | Vannucchi et al. |
| 2012/0301464 | A1 | 11/2012 | Friedman et al. |
| 2012/0329782 | A1 | 12/2012 | Arvanitis et al. |
| 2013/0018034 | A1 | 1/2013 | Yao et al. |
| 2013/0040973 | A1 | 2/2013 | Vannucchi et al. |
| 2013/0045963 | A1 | 2/2013 | Rodgers et al. |
| 2013/0060026 | A1 | 3/2013 | Zhou et al. |
| 2013/0137681 | A1 | 5/2013 | Rodgers et al. |
| 2013/0225556 | A1 | 8/2013 | Rodgers et al. |
| 2013/0253190 | A1 | 9/2013 | Zhou et al. |
| 2013/0253191 | A1 | 9/2013 | Zhou et al. |
| 2013/0253193 | A1 | 9/2013 | Zhou et al. |
| 2013/0274257 | A1 | 10/2013 | Arvanitis et al. |
| 2013/0296299 | A1 | 11/2013 | Rodgers et al. |
| 2014/0005166 | A1 | 1/2014 | Rodgers et al. |
| 2014/0005210 | A1 | 1/2014 | Rodgers et al. |
| 2014/0018374 | A1 | 1/2014 | Rodgers et al. |
| 2014/0031344 | A1 | 1/2014 | Arvanitis et al. |
| 2014/0073657 | A1 | 3/2014 | Li et al. |
| 2014/0094477 | A1 | 4/2014 | Rodgers et al. |
| 2014/0121198 | A1 | 5/2014 | Li et al. |
| 2014/0171409 | A1 | 6/2014 | Yao et al. |
| 2014/0221379 | A1 | 8/2014 | Rodgers et al. |
| 2014/0228346 | A1 | 8/2014 | Rodgers et al. |
| 2014/0243360 | A1 | 8/2014 | Rodgers et al. |
| 2014/0256941 | A1 | 9/2014 | Liu et al. |
| 2014/0275031 | A1 | 9/2014 | Huang et al. |
| 2014/0303196 | A1 | 10/2014 | Rodgers et al. |
| 2014/0343030 | A1 | 11/2014 | Li et al. |
| 2015/0087632 | A1 | 3/2015 | Rodgers et al. |

FOREIGN PATENT DOCUMENTS

| | | |
|---|---|---|
| EP | 0587473 | 3/1994 |
| EP | 0727217 | 8/1996 |
| EP | 0795556 | 9/1997 |
| EP | 1104764 | 6/2001 |
| JP | 07-010876 | 1/1995 |
| JP | 2003/155285 | 5/2003 |
| JP | 2006/518341 | 8/2006 |
| WO | WO 96/30343 | 10/1996 |
| WO | WO 97/02262 | 1/1997 |
| WO | WO 97/02266 | 1/1997 |
| WO | WO 97/36587 | 10/1997 |
| WO | WO 97/38664 | 10/1997 |
| WO | WO 97/45412 | 12/1997 |
| WO | WO 98/44797 | 10/1998 |
| WO | WO 98/51391 | 11/1998 |
| WO | WO 99/00654 | 1/1999 |
| WO | WO 99/62908 | 12/1999 |
| WO | WO 99/65908 | 12/1999 |
| WO | WO 99/65909 | 12/1999 |
| WO | WO 00/09495 | 2/2000 |
| WO | WO 00/51614 | 9/2000 |
| WO | WO 00/53595 | 9/2000 |
| WO | WO 00/63168 | 10/2000 |

(56) References Cited

FOREIGN PATENT DOCUMENTS

| | | |
|---|---|---|
| WO | WO 01/14402 | 3/2001 |
| WO | WO 01/27104 | 4/2001 |
| WO | WO 01/42246 | 6/2001 |
| WO | WO 01/64655 | 9/2001 |
| WO | WO 01/81345 | 11/2001 |
| WO | WO 01/98344 | 12/2001 |
| WO | WO 02/00196 | 1/2002 |
| WO | WO 02/00661 | 1/2002 |
| WO | WO 02/16370 | 2/2002 |
| WO | WO 02/46184 | 6/2002 |
| WO | WO 02/055084 | 7/2002 |
| WO | WO 02/055496 | 7/2002 |
| WO | WO 02/060492 | 8/2002 |
| WO | WO 02/080926 | 10/2002 |
| WO | WO 02/092573 | 11/2002 |
| WO | WO 02/096909 | 12/2002 |
| WO | WO 03/000695 | 1/2003 |
| WO | WO 03/011285 | 2/2003 |
| WO | WO 03/024967 | 3/2003 |
| WO | WO 03/037347 | 5/2003 |
| WO | WO 03/048162 | 6/2003 |
| WO | WO 03/092595 | 11/2003 |
| WO | WO 03/099771 | 12/2003 |
| WO | WO 03/099796 | 12/2003 |
| WO | WO 2004/003026 | 1/2004 |
| WO | WO 2004/005281 | 1/2004 |
| WO | WO 2004/005282 | 1/2004 |
| WO | WO 2004/026406 | 4/2004 |
| WO | WO 2004/041814 | 5/2004 |
| WO | WO 2004/046120 | 6/2004 |
| WO | WO 2004/047843 | 6/2004 |
| WO | WO 2004/056786 | 7/2004 |
| WO | WO 2004/072063 | 8/2004 |
| WO | WO 2004/080980 | 9/2004 |
| WO | WO 2004/092154 | 10/2004 |
| WO | WO 2004/099204 | 11/2004 |
| WO | WO 2004/099205 | 11/2004 |
| WO | WO 2005/005988 | 1/2005 |
| WO | WO 2005/013986 | 2/2005 |
| WO | WO 2005/020921 | 3/2005 |
| WO | WO 2005/026129 | 3/2005 |
| WO | WO 2005/028444 | 3/2005 |
| WO | WO 2005/049033 | 6/2005 |
| WO | WO 2005/051393 | 6/2005 |
| WO | WO 2005/060972 | 7/2005 |
| WO | WO 2005/061463 | 7/2005 |
| WO | WO 2005/062795 | 7/2005 |
| WO | WO 2005/089502 | 9/2005 |
| WO | WO 2005/095400 | 10/2005 |
| WO | WO 2005/105146 | 11/2005 |
| WO | WO 2005/105814 | 11/2005 |
| WO | WO 2005/105988 | 11/2005 |
| WO | WO 2005/110410 | 11/2005 |
| WO | WO 2005/117909 | 12/2005 |
| WO | WO 2005/121130 | 12/2005 |
| WO | WO 2005/123719 | 12/2005 |
| WO | WO 2006/004984 | 1/2006 |
| WO | WO 2006/013114 | 2/2006 |
| WO | WO 2006/022459 | 3/2006 |
| WO | WO 2006/039718 | 4/2006 |
| WO | WO 2006/046023 | 5/2006 |
| WO | WO 2006/046024 | 5/2006 |
| WO | WO 2006/052913 | 5/2006 |
| WO | WO 2006/056399 | 6/2006 |
| WO | WO 2006/067445 | 6/2006 |
| WO | WO 2006/069080 | 6/2006 |
| WO | WO 2006/077499 | 7/2006 |
| WO | WO 2006/096270 | 9/2006 |
| WO | WO 2006/101783 | 9/2006 |
| WO | WO 2006/108103 | 10/2006 |
| WO | WO 2006/122806 | 11/2006 |
| WO | WO 2006/127587 | 11/2006 |
| WO | WO 2006/129199 | 12/2006 |
| WO | WO 2006/136823 | 12/2006 |
| WO | WO 2007/002433 | 1/2007 |
| WO | WO 2007/025090 | 3/2007 |
| WO | WO 2007/041130 | 4/2007 |
| WO | WO 2007/043677 | 4/2007 |
| WO | WO 2007/044894 | 4/2007 |
| WO | WO 2007/049041 | 5/2007 |
| WO | WO 2007/062459 | 6/2007 |
| WO | WO 2007/070514 | 6/2007 |
| WO | WO 2007/076423 | 7/2007 |
| WO | WO 2007/077949 | 7/2007 |
| WO | WO 2007/084557 | 7/2007 |
| WO | WO 2007/090141 | 8/2007 |
| WO | WO 2007/090748 | 8/2007 |
| WO | WO 2007/116313 | 10/2007 |
| WO | WO 2007/117494 | 10/2007 |
| WO | WO 2007/129195 | 11/2007 |
| WO | WO 2007/135461 | 11/2007 |
| WO | WO 2007/140222 | 12/2007 |
| WO | WO 2008/013925 | 1/2008 |
| WO | WO 2008/028937 | 3/2008 |
| WO | WO 2008/035376 | 3/2008 |
| WO | WO 2008/043031 | 4/2008 |
| WO | WO 2008/058126 | 5/2008 |
| WO | WO 2008/064157 | 5/2008 |
| WO | WO 2008/067119 | 6/2008 |
| WO | WO 2008/077712 | 7/2008 |
| WO | WO 2008/079291 | 7/2008 |
| WO | WO 2008/079292 | 7/2008 |
| WO | WO 2008/082198 | 7/2008 |
| WO | WO 2008/082839 | 7/2008 |
| WO | WO 2008/082840 | 7/2008 |
| WO | WO 2008/106692 | 9/2008 |
| WO | WO 2008/124323 | 10/2008 |
| WO | WO 2008/139161 | 11/2008 |
| WO | WO 2008/145681 | 12/2008 |
| WO | WO 2008/145688 | 12/2008 |
| WO | WO 2008/157207 | 12/2008 |
| WO | WO 2008/157208 | 12/2008 |
| WO | WO 2009/016460 | 2/2009 |
| WO | WO 2009/049028 | 4/2009 |
| WO | WO 2009/064486 | 5/2009 |
| WO | WO 2009/064835 | 5/2009 |
| WO | WO 2009/071577 | 6/2009 |
| WO | WO 2009/100130 | 8/2009 |
| WO | WO 2009/109576 | 9/2009 |
| WO | WO 2009/114512 | 9/2009 |
| WO | WO 2009/115572 | 9/2009 |
| WO | WO 2009/155156 | 12/2009 |
| WO | WO 2009/158687 | 12/2009 |
| WO | WO 2010/000978 | 1/2010 |
| WO | WO 2010/001169 | 1/2010 |
| WO | WO 2010/020905 | 2/2010 |
| WO | WO 2010/022076 | 2/2010 |
| WO | WO 2010/022081 | 2/2010 |
| WO | WO 2010/026121 | 3/2010 |
| WO | WO 2010/026122 | 3/2010 |
| WO | WO 2010/026124 | 3/2010 |
| WO | WO 2010/039939 | 4/2010 |
| WO | WO 2010/081692 | 7/2010 |
| WO | WO 2010/083283 | 7/2010 |
| WO | WO 2010/135621 | 11/2010 |
| WO | WO 2010/135650 | 11/2010 |
| WO | WO 2011/003418 | 1/2011 |
| WO | WO 2011/025685 | 3/2011 |
| WO | WO 2011/028685 | 3/2011 |
| WO | WO 2011/029802 | 3/2011 |
| WO | WO 2011/031554 | 3/2011 |
| WO | WO 2011/035900 | 3/2011 |
| WO | WO 2011/044481 | 4/2011 |
| WO | WO 2011/057784 | 5/2011 |
| WO | WO 2011/069141 | 6/2011 |
| WO | WO 2011/112662 | 9/2011 |
| WO | WO 2011/130146 | 10/2011 |
| WO | WO 2011/144338 | 11/2011 |
| WO | WO 2011/146808 | 11/2011 |
| WO | WO 2012/003457 | 1/2012 |
| WO | WO 2012/068440 | 5/2012 |
| WO | WO 2012/068450 | 5/2012 |
| WO | WO 2012/177606 | 12/2012 |
| WO | WO 2013/007765 | 1/2013 |

(56) References Cited

FOREIGN PATENT DOCUMENTS

| | | |
|---|---|---|
| WO | WO 2013/007768 | 1/2013 |
| WO | WO 2013/023119 | 2/2013 |
| WO | WO 2013/026025 | 2/2013 |
| WO | WO 2013/036611 | 3/2013 |
| WO | WO 2013/173720 | 11/2013 |
| WO | WO 2014/071031 | 5/2014 |

OTHER PUBLICATIONS

Abelson et al., "Dry eye syndrome: diagnosis, clinical trials, and pharmaceutical treatment-'improving clinical trials'. Lacrimal Gland, Tear Film, and Dry Eye Syndromes 3 Part B", Adv Exp Med Biol, 2002; 506:1079-86).

Abstract of Chilean patent application No. 3496-06 published in Official Gazette of the Republic of Chile (Jun. 1, 2007) and publication (2 pages).

Aho, T. et al., Expression of human pim family genes is selectively up-regulated by cytokines promoting T helper type 1, but not T helper type 2, cell differentiation, Immunology 116: 82-88, 2005.

Albach et al., "Diagnosis of keratoconjunctivitis sicca in rheumatoid arthritis. The value of various tests", Ophthalmologe, Apr. 1994; 91(2):229-34—in German (with English abstract/summary contained therein).

Anderson et al., "Biochemical characterization of GSK1070916, a potent and selective inhibitor of Aurora B and Aurora C kinases with an extremely long residence time", Biochem. J., 420(2), 259-265 (2009).

Bachmann, et al., "The serine/threonine kinease Pim-1," The International Journal of Biochechemistry and Cell Biology 37: 726-730 (2005).

Banker, et al., "Modern Pharmaceuticals" p. 596 (1996).

Barabino et al., "Tear film and ocular surface tests in animal models of dry eye; uses and limitations", Experimental Eye Research, 2004, 79, 613-621.

Barr et al., "Corneal scarring in the Collaborative Longitudinal Evaluation of Keratoconus (CLEK) Study: baseline prevalence and repeatability of detection", Cornea, 1999; 18(1):34-46.

Baudouin et al., "Flow cytometry in impression cytology specimens. A new method for evaluation of conjunctival Inflammation", Invest Ophthalmol Vis Sci, 1997; 38:1458-1464.

Baytel et al., "The human Pim-2 proto-oncogene and its testicular expression" Biochimica et Biophysica Acta 1442: 274-285, (1998).

Begley, et al., "Use of the dry eye questionnaire to measure symptoms of ocular irritation in patients with aqueous tear deficient dry eye", Cornea, 2002:21:664-70.

Bell, Malcolm, and Zalay, Andrew, "Synthesis of Substituted 3-Amino[6, 5-b] triazinoindoles." Journal of Heterocyclic Chemistry, 12(5):1001-1004, Oct. 1975.

Berge, et al., "Pharmaceutical salts", J. Pharma. Science (1977) vol. 66(1) pp. 1-19.

Beyer, "Uber die Synthese von 2-Methylmercapto-1.3.4-thiodiazinen and deren Umlagerung in Pyrazolderivate (The synthesis of 2-methylthio-1,3,4-thiadiazines and their rearrangement to pyrazole derivatives)", Chem. Berichte Jahrg., 92:2593-2599 (1959) (abstract provided).

Bhattacharya et al., "Brittain, ed. Polymorphism in Pharmaceutical Solids," 2009, p. 327-345.

Bhovi, et al., "1 ,3-Dipolar Cycloaddition Reaction: Synthesis and Antimicrobial, Activity of Some New 3-Ethoxycarbonyl-s-Methoxy-6-Bromo-2-Triazolylmethylindoles", Indian Journal of Heterocyclic Chemistry, vol. 14, (Jul.-Sep. 2004), pp. 15-18.

Bioreversible Carriers in Drug Design, ed. Edward B. Roche, American Pharmaceutical Association and Pergamon Press, 1987* too voluminous to provide.

Blume-Jensen, et al, "Oncogenic kinase signaling", Nature 2001, 411(6835):355-365.

Bock, C., et al. "Managing drug resistance in cancer: lessons from HIV therapy." Nature. (Jul. 2012), vol. 12, pp. 494-501.

Bolen, "Nonreceptor tyrosine protein kinases", Oncogene, 1993, 8(8):2025-31.

Bollrath et al., "gp130-Mediated Stat3 Activation in Enterocytes Regulates Cell Survival and Cell-Cycle Progression during Colitis-Associated Tumorigenesis," Cancer Cell, 15:91-102 (2009).

Borie, et al., "Combined Use of the Jak3 Inhibitor CP-690, 550 with Mycophenolate Mofetil to Prevent Kidney Allograft Rejection in Nonhuman Primates", Transplantation, Dec. 27, 2005;80(12):1756-64.

Bosworth, JAK1/JAK2 Inhibitor Ruxolitinib Is a Rising Start, Clinical Oncology, vol. 06:04 (Apr. 2011) 3 pages.

Boudny, et al., "JAK/STAT signaling pathways and cancer", Neoplasm, 49:349-355, 2002.

Bourcier et al., "Expression of CD40 and CD40 ligand in the human conjunctival epithelium", Invest Ophthalmol Vis Sci, 2000;41:120-126.

Bowman, et al. "STATs in oncogenesis", Oncogene, 19:2474-2488, 2000.

Brignole et al., "Expression of Fas-Fas Ligand Antigens and Apoptotic Marker APO2-7 by the Human Conjunctival Epithelium. Positive correlation with class II HLA DR expression in inflammatory Ocular Surface Disorders", Exp Eye Res, 1998;67:687-697.

Brignole et al., "Flow cytometric analysis of inflammatory markers in conjunctival epithelial cells of patients with dry eyes", Invest Ophthalmol Vis Sci, 2000; 41:1356-1363.

Brignole et al., "Flow cytometric analysis of inflammatory markers in KCS: 6-month treatment with topical cyclosporin A", Invest Ophthalmol Vis Sci, 2001; 42:90-95.

Brignole et al., "Flow cytometry in conjunctival impression cytology: a new tool for exploring ocular surface pathologies", Exp Eye Res, 2004;78:473-481.

Bromberg et al., "Inflammation and Cancer: IL-6 and STAT3 Complete the Link," Cancer Cell, 15:79-80 (2009).

Bron, et al., "Grading of corneal and conjunctival staining in the context of other dry eye tests", Cornea, 2003;22(7):640-50.

Bron, et al., "Methodologies to Diagnose and Monitor Dry Eye Disease: Report of the Diagnostic Methodology Subcommittee of the International Dry Eye Workshop (2007)", The Ocular Surface, 5(2), 108-152 (Apr. 2007).

Burger et al., "Janus kinase inhibitor INCB20 has antiproliferative and apoptotic effects on human myeloma cells in vitro and in vivo", Mol. Cancer Ther. 2009:8(1), Jan. 2009 pp. 26-35.

Burger, et al., "Gp130 and ras mediated signaling in human plasma cell line IN/a-6: a cytokine-regulated tumor model for plasmacytoma", Hematol J., 2:42-53, 2001.

Campas-Moya, C., "Ruxolitinib. Tyrosine-protein kinase JAK1/2 inhibitor, treatment of myelofibrosis, treatment of myeloproliferative neoplasms, treatment of psoriasis", Drugs of the Future, (Jun. 2010) vol. 35, No. 6, pp. 457-465.

Candotti, et al. (2002). "Molecular aspects of primary immunodeficiencies: lessons from cytokine and other signaling pathways.", J Clin Invest, 109(10): 1261-9.

Candotti, F., et al. (1997). "Structural and functional basis for JAK3-deficient severe combined immunodeficiency.", Blood, 90(10): 3996-4003.

Carey and Sundberg, Advanced Organic Chemistry, Part B: Reactions and Synthesis, 4th ed., Kluwer Academic/Plenum Publishers:New York, pp. 111-119 (2001).

Carey and Sundberg, Advanced Organic Chemistry, Part B: Reactions and Synthesis, Oxidations, 4th ed., Kluwer Academic/Plenum Publishers:New York, pp. 747-757 (2001).

Cermak, et al, "Is complete androgen insensitivity syndrome associated with alterations in the meibomium gland and ocular surface", Cornea, 2003;22:516-521.

Cetkovic-Cvrlje, et al. (2003). "Targeting JAK3 with JANEX-1 for prevention of autoimmune type 1 diabetes in NOD mice.", Clin Immunol, 106(3): 213-25.

Chalandon, "Targeting mutated protein tyrosine kinases and their signaling pathways in hematologic malignancies", Haematologica, 90 (7):949-68 (2005).

Changelian, et al., "Prevention of Organ Allograft Rejection by a Specific Janus Kinase 3 Inhibitor", Science, 2003, 302, 875-878.

Chauhan, et al, "Autoimmunity in Dry Eye due to resistance of Th17 to Treg Suppression", J. Immunology, 182(3):1247-52 (2009).

(56) References Cited

OTHER PUBLICATIONS

Chen, et al., "Stat3 Activation in Human Endometrial and Cervical Cancer", British Journal of Cancer, 96, 591-599, 2007.
Chew, et al., "An instrument for quantifying meibomian lipid on the lid margin: the Meibometer", Curr Eye Res, 1993a;12:247-254.
Chew, et al., "The casual level of meibomian lipids in humans", Current Eye Research, 1993b;12:255-259.
Cho, et al, "Review of the tear break-up time and a closer look at the tear break-up time of Hong Kong Chinese", Optom Vis Sci, 1993;70(1):30-8.
Choi Ha-Soon, et al, "Design and synthesis of 7H-pyrrolo[2,3-d]pyrimidines as focal adhesion kinase inhibitors. Part 1", Bioorg. & Med. Chem. Lett., 16(8):2173-2176 (2006).
Chu-Moyer, et al., "Preparation of the Four Regioisomeric 2-(Methylthio)oxazolopyridines: Useful Synthons for Elaboration to 2-(Amino substituted)oxazolopyridines", J. Org. Chem. 60(17): 5721-5725 (1995).
Cilloni et al., "Emerging drugs for chronic myeloid leukemia", Expert Opinion on Emerging Drugs, (Jun. 2010) vol. 15, No. 2, pp. 175-184.
Clark et al., "Discovery and Development of Janus Kinase (JAK) inhibitors for Inflammatory Diseases," J Med Chem., 2014, pp. A-P.
Coligan, J.E. et al, Wiley Press; Methods in Molecular Biology: vol. 225, Inflammation Protocols., Winyard, P.G. and Willoughby, D.A., Humana Press (2003)* too voluminous to provide.
Communication dated Jan. 22, 2009 for European Appln. No. 06839328.9 (5 pgs.)
Conklyn, M. et al., "The JAK3 inhibitor CP0690550 selectively reduces NK and CD8+ cell numbers in cynomolgus monkey blood following chronic oral dosing", Journal of Leukocyte Biology, 2004, 76, 1248-1255.
Costa Rican Office Action in CR Application No. 10065, dated Jul. 16, 2013, 8 pages.
Craig et al. "Tear lipid layer structure and stability following expression of the meibomian glands.", Ophthalmic Physiol Opt, 1995, 15(6):569-74.
Current Protocols in Immunology, vol. 3., Coligan, J.E. et al, Wiley Press (1988)* too voluminous to provide.
Daniels et al., "Imatinib mesylate inhibits the profibrogenic activity of TGF-? and prevents bleomycinmediated lung fibrosis." J. Clin. Invest., 114(9):1308-1316, Nov. 2004.
Danjo et al., "Observation of precorneal tear film in patients with Sjogren's syndrome", Acta Ophthalmol Scand, 73:501-505 (1995).
De Paiva, et al, "IL-17 disrupts corneal barrier following desiccating stress", Mucosal Immunol. 2(3):243-53 (2009).
De Vos, J., et al. (2000). "JAK2 tyrosine kinase inhibitor tyrphostin AG490 downregulates the mitogen-activated protein kinase (MAPK) and signal transducer and activator of transcription (STAT) pathways and induces apoptosis in myeloma cells.", Br J Haematol, 109(4): 823-8.
Deng Jun, et al, "Rh-catalyzed asymmetric hydrogenation of gamma-phthalimido-substituted esters: an efficient enantioselective synthesis of beta-aryl-gamma-amino acids", Org. Lett. 9(23):4825-4827 (2007).
Deuse, T. et al., "Novel Immunosuppression: R348, a JAK3- and Syk-Inhibitor Attenuates Acute Cardiac Allograft Rejection", Transplantation, 2008, 85(6) 885-892.
Doane, "An instrument for in vivo tear film interferometry", Optom Vis Sci, 1989; 66: 383-8.
Doleschall G., et al., "Thermal and Acid Catalysed Degradations of 3-alkylthio-6,7- dihydro[1.2.4]triazino[1,6-c]quinazolin-5-ium-l-olates", Tetrahedron, 30:3997-4012, 1974.
Dudley, A.C., et al. "AVEGF/JAK2/STAT5 axis may partially mediate endothelial cell tolerance to hypoxia", Biochem. J. 2005, 390(Pt 2):427-36.
Eghtedar, "Phase II Study of the JAK2 Inhibitor, INCB018424, in Patients with Refractory Leukemias Including Post-Myeloproliferative Disorder Acute Myeloid Leukemia", American Society of Hematology (ASH) annual meeting in Orlando, FL (Dec. 6, 2010), Abstract/poster 509.
Einmahl, et al., "Therapeutic applications of viscous and injectable poly(ortho esters)", Adv. Drug. Deliv. Rev. 53:45-73 (2001).
Eliason, et al., "Staining of the conjunctiva and conjunctival tear film", Br J Ophthalmol, 1990;74:519-22.
Expert Scientific Group on Phase One Clinical Trials Final Report, Nov. 30, 2006, pp. Cl, C35-C38.
Fabrizio Saettone, "Ocular inserts for topical delivery", Advanced Drug Delivery Reviews 16:95-106 (1998).
Farrell et al., "A classification for dry eyes following comparison of tear thinning time with Schirmer tear test", Acta Ophthalmol (Copenh), 1992; 70(3):357-60.
Farrell et al., "A clinical procedure to predict the value of temporary occlusion therapy in keratoconjunctivitis sicca" Ophthal Physiol Opt, 2003;23:1-8.
Farris, "Tear osmolarity—a new gold standard?" Adv Exp Med Biol, 350:495-503, 1994.
Fiskus, W. et al., "Synergistic Activity of Combinations of JAK2 Kinase Inhibitor with PI3K/mTOR, MEK or PIM Kinase Inhibitor Against Human Myeloproliferative Neoplasm Cells Expressing JAK2V617F" J. American Chem. Soc., 52nd Annual Meeting of the American-Society-of-Hematology (ASH); Orlando, FL, USA; Dec. 4-7, 2010, ACS Publications; vol. 116, No. 21 Nov. 1, 2010 p. 349, XP002667216, ISSN: 0002-7863 (1 page).
Flex E., et al., "Somatically acquired JAK1 mutations in adult acute lymphoblastic leukemia", J. Exp Med. 205:751-8, (2008).
Fonseca, J.E. et al., "Interleukin-6 as a key player in systemic inflammation and joint destruction", Autoimmunity Reviews, 8:538-42, (2009).
Fridman, et al., "Preclinical evaluation of local JAK1 and JAK2 inhibition in cutaneous inflammation", Journal of Investigative Dermatology, (Sep. 2011) vol. 131, No. 9, pp. 1838-1844.
Fridman, J. et al. "Selective JAK Inhibition is Efficacious against Multiple Myeloma Cells and Reverses the Protective Effects of Cytokine and Stromal Cell Support" Abstract #0956, presented Sunday, Jun. 15, 2008 at the European Hematology Association, 13th Congress, Jun. 12-15, Copenhagen, Denmark (1 page).
Fridman, Jordan et al. "Discovery and Preclinical Characterization of INCB018424, a Selective JAK2 Inhibitor for the Treatment of Myeloproliferative Disorders" poster presented at the American Society of Hematology, 49th Annual Meeting and Exposition, GA. Abstract #3538, poster #757, Dec. 10, 2007 (1 page).
Fridman, Jordan et al. "Efficacy and Tolerability of Novel JAK Inhibitors in Animal Models of Rheumatoid Arthritis" poster presented at the ACR/ARHP (American College of Rheumatology/Association of Rheumatology Health Professionals) Scientific Meeting 2007, Boston, MA. Nov. 10, 2007. Abstract 1771, poster 285 (1 page).
Fridman, Jordan, et al. "Discovery and Preclinical Development of Selective JAK Inhibitors for the Treatment of Hematological Malignancies" poster presented at European Hematology Association, 12th Congress, Vienna, Austria. Abstract 0324, Jun. 8, 2007 (1 page).
Fridman, Jordan, et al. "Discovery and Preclinical Development of Selective JAK Inhibitors for the Treatment of Myeloproliferative Disorders" poster presented at the 4th International Congress on Myeloproliferative Diseases and Myelodysplastic Syndromes, New York, NY. Nov 8-10, 2007. Poster 0009 (1 page).
Fujihara et al., "Evaluation of human conjunctival epithelium by a combination of brush cytology and flow cytometry: an approach to the quantitative technique", Diagn Cytopathol, 1997;17:456-60.
Fujii, C. et al., "Aberrant expression of serine.thereonine kinase Pim-3 in hepatocellular carcinoma development and its role in the proliferation of human hepatoma cell lines" International Journal of Cancer 114: 209-218, (2005).
Fukagawa et al., "Histological evaluation of brush cytology of rabbit conjunctiva", Nippon Ganka Gakkai Zasshi, 1993;97:1173-8 (contains English abstract within the article).
Gaertner, "Cyclization of 1-Alkylamino-3-halo-2-alkanolst o 1-Alkyl-3-azetidinols," J. Org. Chem., 1967, 32, 2972-76.
Ghelardi, et al., "A Mucoadhesive Polymer Extracted from Tamarind Seed Improves the Intraocular Penetration and Efficacy of Rufloxacin in Topical Treatment of Experimental Bacterial Keratitis", Antimicrob. Agents Chemother. 48:3396-3401 (2004).

(56) References Cited

OTHER PUBLICATIONS

Glasson et al., "Differences in clinical parameters and tear film of tolerant and intolerant contact lens wearers", Invest Ophthalmol Vis Sci, 2003;44:5116-5124.
Glattfeld, "Improvements in the Preparation of DL-Threonic and DL-Erythronic Acids", J. Am. Chem. Soc. 62:974-977 (1940).
Gobbels et al., Tear secretion in dry eyes as assessed by objective fluorophotometry. Ger J Ophthalmol, 1992; 1:350-353.
Golding et al., "X-ray and scanning electron microscopic analysis of the structural composition of tear ferns", Cornea Jan. 1994;13(1):58-66.
Gomtsyan, et al, "Design, synthesis, and structure-activity relationship of 6-alkynylpyrimidines as potent adenosine kinase inhibitors", J. Med. Chem. 45(17):3639-3648 (2002).
Gooseman, et al., "The intramolecular b-fluorine . . . ammonium interaction in 4- and 8-membered rings", Chem. Commun, vol. 30, pp. 3190-3192 (2006).
Gone, M.E. et al., "Clinical Resistance to STI-571 Cancer Therapy Caused by BCR-ABL Gene Mutation or Amplification." Science, 293:876, 2001.
Gotlieb, Alice, Presentation at the 2008 American Academy of Dermatology, 66th Annual Meeting, San Antonio, TX. Feb. 1, 2008, symposium-303 (12 pp.).
Goto et al., Color mapping of tear lipid layer thickness distribution from the image analysis in DR-1 tear lipid layer interference images (ARVO abstract). ARVO 2004.
Goto et al., "Computer-synthesis of an interference color chart of human tear lipid layer by a colorimetric approach",Invest Ophthalmol Vis Sci, 2003;44:4693-7.
Goto et al., "Differentiation of lipid tear deficiency dry eye by kinetic analysis of tear interference images", Arch Ophthalmol, 2003;121:173-80.
Goto et al., "Evaluation of the tear film stability after laser in situ keratomileusis using the tear film stability analysis system", Am J Ophthalmol, Jan. 2004b;137(1):116-20.
Goto et al., "Tear Film Stability Analysis System: Introducing a new application for videokeratography", Cornea, Nov. 2004a;23(8):S65-S70.
Goto, et al., Kinetic analysis of tear interference images in aqueous tear deficiency dry eye before and after punctal occlusion. Invest Ophthalmol Vis Sci, 2003;44:1897-905.
Gottlieb, A.B., et al, "Psoriasis: Emerging Therapeutic Strategies", Nat Rev Drug Disc., 4:19-34 (2005).
Grabbe, et al., "Immunoregulatory mechanisms involved in elicitation of allergic-contact hypersensitivity", Immunol Today, Jan; 19(1):37-44 (1998) (only 1 page provide and marked).
Green, T.W. and Wuts, P.G.M.. Protective Groups in Organic Synthesis, 3rd. Ed., Wiley & Sons, Inc., New York (1999)* too voluminous to provide.
Gregory, et al., "Clinical and laboratory features of myelofibrosis and limitations of current therapies", Clinical Advances in Hematology and Oncology, (Sep. 2011) vol. 9, No. 9, pp. 1-3.
Grivennikov, et al., "IL-6 and STAT3 are required for survival of intestinal epithelial cells and the development of colitis-associated cancer", Cancer Cell, 15:103-111 (2009).
Groneberg et al., "Animal models of allergic and inflammatory conjunctivitis," Allergy, 2003, 58, 1101-1113.
Guillon, Jean-Pierre, "Tear film photography and contact lens wear", J Br Contact Lens Assoc, 1982;5:84-7.
Gura, Science, vol. 278, No. 5340, pp. 1041-1042 (1997).
Guschin, et al, "A major role for the protein tyrosine kinase JAK1 in the JAKISTAT signal transduction pathway in response to interleukin-6", Embo J 14:1421-1429 (1995).
Hamze' et al., "Synthesis of Various 3-Substituted 1,2,4-Oxadiazole-Containing Chiral β3- and r-Amino Acids from Fmoc-Protected Aspartic Acid," J. Org. Chem., 2003, 68(19), pp. 7316-7321.
Hardwicke, et al., "GSK1070916, a potent Aurora B/C kinase inhibitor with broad antitumor activity in tissue culture cells and human tumor xenograft models", Molecular Cancer Therapeutics 8(7), 1808-1817 (2009).
Helal et al., "Stereoselective Synthesis of cis-1,3-Disubstituted Cyclobutyl Kinase Inhibitors," Organic Letters, (2004), 6(11), pp. 1853-1856.
Higuchi, et al., "Pro-drugs as Novel Delivery Systems," vol. 14 of the A.C.S. Symposium Series (1975)* too voluminous to provide.
Holly et al., "Lacrimation kinetics in Humans as determined by a novel technique", in Holly FJ (ed). The preocular tear film. Lubbock TX, Lubbock Dry Eye Institute, 1986, pp. 76-88).
Hong, et al., "Total Synthesis of Onnamide A", J. Am. Chem. Soc., 113:9693-94 (1991).
Huang, "Inhibition of STAT3 activity with AG490 decreases the invasion of human pancreatic cancer cells in vitro", Cancer Sci. 97(12):1417-23 (2006).
Huttel, et al., "Lithium pyrazole compounds", Liebigs Ann. Chem. Bd., 625:55-65 (1959) (abstract provided).
International Preliminary Report on Patentability (with Written Opinion) dated Jun. 18, 2008 for International Appln. No. PCT/US2006/047369 (10 pgs.)
International Preliminary Report on Patentability (with Written Opinion) dated Mar. 6, 2012 for International Appln. No. PCT/US2010/047252 (7 pgs.)
International Preliminary Report on Patentability (with Written Opinion) dated Nov. 22, 2011 for International Appln. No. PCT/US2010/035728 (8 pgs.)
International Preliminary Report on Patentability (with Written Opinion) dated Nov. 22, 2011 for International Appln. No. PCT/US2010/035783 (5 pgs.)
International Preliminary Report on Patentability for International Appln. No. PCT/US2008/066662 dated Dec. 17, 2009 (7 pgs.)
International Preliminary Report on Patentability for PCT/US2008/66658 mailed Dec. 17, 2009 (7 pages).
International Preliminary Report on Patentability for PCT/US2009/036635 mailed Sep. 14, 2010 (6 pages).
International Preliminary Report on Patentability for PCT/US2009/059203 mailed Apr. 5, 2011 (6 pages).
International Preliminary Report on Patentability for PCT/US2010/021003 mailed Jul. 19, 2011(11 pages).
International Preliminary Report on Patentability for PCT/US2010/052011 mailed Apr. 11, 2012 (4 pages).
International Preliminary Report on Patentability for PCT/US2011/025433 mailed Aug. 21, 2012 (7 pages).
International Preliminary Report on Patentability for PCT/US2011/027665 mailed Sep. 11, 2012 (7 pages).
International Preliminary Report on Patentability for PCT/US2011/037291 mailed Nov. 27, 2012 (7 pages).
International Preliminary Report on Patentability for PCT/US2011/061351 mailed May 30, 2013 (7 pages).
International Preliminary Report on Patentability for PCT/US2011/061374 mailed May 30, 2013 (5 pages).
International Preliminary Report on Patentability for PCT/US2012/043099 mailed Dec. 23, 2013, 6 pages.
International Preliminary Report on Patentability for PCT/US2012/050210 mailed Feb. 11, 2014, 8 pages.
International Preliminary Report on Patentability for PCT/US2012/051439 mailed Feb. 27, 2014, 7 pages.
International Preliminary Report on Patentability for PCT/US2012/053921 mailed Mar. 20, 2014, 8 pages.
International Search Report and the Written Opinion, PCT/US2012/051439, mailed Nov. 30, 2012 (15 pages).
International Search Report and the Written Opinion, PCT/US2012/053921, mailed Nov. 7, 2012 (19 pages).
International Search Report and Written Opinion dated Feb. 9, 2010 for International Appln. No. PCT/US2009/059203 (10 pages).
International Search Report and Written Opinion for International Appln. No. PCT/US2005/046207 dated May 15, 2007 (6 pages).
International Search Report and Written Opinion for International Appln. No. PCT/US2008/066662 dated Dec. 23, 2008 (11 pgs.)
International Search Report and Written Opinion for International Appln. No. PCT/US2009/036635 dated Jun. 3, 2009 14 pages.
International Search Report and Written Opinion for PCT/US2006/047369, 16 pages (Apr. 24, 2007).
International Search Report and Written Opinion for PCT/US2008/083319, 29 pages mailed Mar. 13, 2009.

(56) References Cited

OTHER PUBLICATIONS

International Search Report and Written Opinion for PCT/US2011/025433, 12 pages (mailed Jul. 20, 2011).
International Search Report and Written Opinion for PCT/US2011/027665 mailed Jun. 27, 2011 (14 pages).
International Search Report and Written Opinion for PCT/US2011/037291, 11 pages (Apr. 19, 2012).
International Search Report and Written Opinion for PCT/US2011/061351 mailed Feb. 17, 2012 (12 pages).
International Search Report and Written Opinion for PCT/US2011/061374 mailed Mar. 27, 2012 (10 pages).
International Search Report and Written Opinion for PCT/US2012/025581, 16 pages (mailed Apr. 26, 2011).
International Search Report and Written Opinion for PCT/US2012/043099, 11 pages (Sep. 13, 2012).
International Search Report and Written Opinion for PCT/US2012/050252 mailed Jan. 2, 2013, 17 pages.
International Search Report for PCT/US2008/66658 mailed Dec. 23, 2008 (4 pages).
International Search Report for PCT/US2010/021003 mailed Aug. 16, 2010 (8 pages).
International Search Report for PCT/US2010/035728 mailed Jul. 8, 2010 (3 pages).
International Search Report for PCT/US2010/035783 mailed Aug. 23, 2010 (4 pages).
International Search Report for PCT/US2010/047252 mailed Nov. 17, 2010 (4 pages).
International Search Report for PCT/US2010/052011 mailed Nov. 30, 2010 (3 pages).
International Search Report and Written Opinion in International Application No. PCT/US2014/020554, dated Jul. 16, 2014, 17 pages.
Iranpoor, N.; Firouzabadi, H.; Aghapour, "A Rapid and Facile Conversion of Primary Amides and Aldoximes to Nitriles and Ketoximes to Amides with Triphenylphosphine and N-Chlorosuccinimide", G Syn. Commun 32:2535-41 (2002).
Ishizaki, et al., "Pharmacological Properties of Y-27632, a Specific Inhibitor of Rho-Associated Kinases", Molecular Pharmacology, 2000, 57, 976-983.
Itagaki, et al, "Expedient Synthesis of Potent Cannabinoid Receptor Agonist (−)-CP55,940", Organic Letters, 2005; 7(19); 4181-4183.
James, et al., "A unique clonal JAK2 mutation leading to constitutive signalling causes polycythaemia vera", Nature, 434 (7037):1144-8 (2005).
Janes, M. et al., "Effective and selective targeting of leukemia cells using a TORC1/2 kinase inhibitor.", Nature Medicine (2010) LNKD-PUBMED:20072130, vol. 16, No. 2, pp. 205-213 XP002673719.
Jee, et al "Overview: animal models of osteopenia and osteoporosis", J Musculoskel. Neuron, Interact., 1(3):193-207 (2001).
Jester, et al., "In vivo biomcroscopy and photography of meibomian glands in a rabbit model of meibomian gland dysfunction", Invest Ophthalmol Vis Sci, 1982;22:660-7.
Johnson, et al., "The effect of instilled fluorescein solution volume on the values and repeatability of TBUT measurements", Cornea, 2005;24:811-7.
Kaercher, T., "Ocular symptoms and signs in patients with ectodermal dysplasia symdromes", Grafes Arch Clin Exp Ophthalmol, 2004;495-500.
Kamb, Nature Reviews Drug Discovery 4, pp. 161-165 (2005).
Kaushansky, K., "Lineage-Specific Hematopoietic Growth Factors", NEJM 354:2034-45 (2006).
Kawamura, et al. (1994). "Molecular cloning of L-JAK, a Janus family protein-tyrosine kinase expressed in natural killer cells and activated leukocytes.", Proc Natl Acad Sci U S A, 91(14): 6374-8).
Kharas, et al., "ABL Oncogenes and Phosphoinositide 3-Kinase: Mechanism of Activation and Downstream Effectors.", Cancer Res., 65(6):2047-2053, Mar. 15, 2005.
Kim, et al., "Zinc-Modified Cyanoborohydride as a Selective Reducing Agent", J. Org. Chem. 50: 1927-1932 (1985).
King-Smith et al., "Three interferometric methods for measuring the thickness of layers of the tear film", Optom Vis Sci, 1999; 76:19-32.
Kiss, Robert, "Recent developments on JAK2 inhibitors: A patent review", Expert Opinion on Therapeutic Patents, (Apr. 2010) vol. 20, No. 4, pp. 471-495.
Kojima et al., "A new noninvasive tear stability analysis system for the assessment of dry eyes", Invest Ophthalmol Vis Sci, May 2004;45(5):1369-74).
Kola, Nature Reviews Drug Discovery 3, pp. 711-715 (2004).
Komuro et al., "Assessment of meibomian gland function by a newly developed laser meibometer", Adv Exp Med Biol, 2002; 506:517-520.
Korb et al., "The effect of two novel lubricant eye drops on tear film lipid layer thickness in subjects with dry eye symptoms", Optom Vis Sci, 2005; 82: 594-601.
Korb, et al., "Increase in tear film lipid layer thickness following treatment of meibomian gland dysfunction", Adv Exp Med Biol, 1994;350:293-8.
Korolev, et al., "Pd-EDTA as an efficient catalyst for Suzuki-Miyaura reactions in water", Tet. Lett. 46: 5751-5754 (2005).
Kortylewski, et al., "Regulation of the IL-23 and IL-12 balance by Stat3 signaling in the tumor microenvironment", Cancer Cell, 15:114-123 (2009).
Kruh et al., "The complete coding sequence of arg defines the Abelson subfamily of cytoplasmic tyrosine kinases.", Proc. Natl. Acad. Sci., 87:5802-5806, Aug. 1990.
Kubinyi, H. "QSAR: Hansch Analysis and Related Approaches," Methods and Principles in Medicinal Chemistry, Manhold, R. ed. Weinhein, NY, 1993.
Kudelacz, et al. "The JAK-3 inhibitor CP-690550 is a potent anti-inflammatory agent in a murine model of pulmonary eosinophilia", European Journal of Pharmacology 582 (2008) 154-161.
Kumar, C., "Kinase drug discovery approaches in chronic myeloproliferative disorders", Oncogene, (Jun. 18, 2009) vol. 28, No. 24, pp. 2305-2323.
Kuo, et al., "Pd-EDTA as an efficient catalyst for Suzuki-Miyaura reactions in water", Chem Commun 301-3 (2007).
Kuppens et al., "Basal tear turnover and topical timolol in glaucoma patients and healthy controls by Fluorophotometry", Invest Ophthalmol Vis Sci, 1992; 33:3442-3448.
Lai, et al., "Mechanistic Study on the Inactivation of General Acyl-CoA Dehydrogenase by a Metabolite of Hypoglycin A", J. Am. Chem. Soc. 113: 7388-7397 (1991).
Lam, et al, "Tear Cytokine Profiles in Dysfunctional Tear Syndrome", Am J Ophthalmol., 147(2):198-205 (2009).
Larock, R., "Comprehensive Organic Transformations", Wiley-VCH, 2nd Ed. (1999) pp. 1949-1950, 1958-1959, 1976, and 1983-1985.
Leaf, Clifton, Health Administrator vol. XVII, No. 1:172-183 (2005).
Lemp "Report of National Eye Institute/Industry Workshop on clinical trials in dry eyes", CLAO J, 1995;21:221-232.
Lemp et al., "Corneal desiccation despite normal tear volume", Ann Ophthalmol, 1970 (2) pp. 258-261 & 284.
Lemp et al., "The Definition and Classification of Dry Eye Disease: Report of the Definition and Classification Subcommittee of the International Dry Eye WorkShop", The Ocular Surface, 5(2), 75-92 Apr. 2007.
Letter translation of Office Action, Chilean Application No. 3496-2006 as received from the foreign associate (Jul. 5, 2010) (4 pages).
Levine, et al., "Activating mutation in the tyrosine kinase JAK2 in polycythemia vera, essential thrombocythemia, and myeloid metaplasia with myelofibrosis", Cancer Cell, vol. 7, 2005: 387-397.
Levitzki, "Tyrosine kinases as targets for cancer therapy", Eur. J. Cancer 38(suppl. 5):S11-S18 (2002).
Levy, et al. "INCB018424 A Selective Janus Kinase 1/2 Inhibitor" Presentation at the 50th American Society of Hematology Annual Meeting (ASH), Dec. 8, 2008.
Levy, et al., INCB18424 Discussion presentation at the American Society of Hematology, 49th Annual Meeting and Exposition, Atlanta, GA. Abstract #558, Dec. 10, 2007 (25 pages).
Li, et al., "Pim-3, a proto-oncogene with serine/threonine kinase activity, is aberrantly expressed in human pancreatic cancer and phosphorylates Bad-mediated apoptosis in human pancreatic cell lines" Cancer Research 66(13): 6741-7 (2006).

(56) References Cited

OTHER PUBLICATIONS

Lin, "Constitutive Activation of JAK3/STAT3 in Colon Carcinoma Tumors and Cell Lines", Am J Pathol. 167(4):969-80 (2005).
Lin, et al., "Enantioselective synthesis of Janus kinase inhibitor INCB018424 via an organocatalytic aza-Michael reaction," Organic Letters, (2009), 11(9), 1999-2002.
Liu, et al., "Combined Inhibition of Janus Kinase 1/2 for the Treatment of JAK2V617F-Driven Neoplasms: Selective Effects on Mutant Cells and Improvements in Measures of Disease Severity", Clin Cancer Res 2009;15(22) pp. 6891-6900; Nov. 15, 2009; Published Online First on Nov. 3, 2009 as 10.1158/1078-0432.CCR-09-1298.
Lucet et al., "The structural basis of Janus kinas 2 inhibition by a potent and specific pan-Janus kinase inhibitor," Blood, 2006, 107(1):176-183.
Macchi, et al., "Mutations of Jak-3 gene in patients with autosomal severe combined immune deficiency (SCID)", Nature 377:65-8 (1995).
Madden et al. Comparative study of two non-invasive tear film stability techniques. Curr Eye Res, 1994; 13(4):263-9.
Madhusudan et al., "Tyrosine kinase inhibitors in cancer therapy", Clin Biochem., 2004, 37(7):618-35.
Maffioli, et al., "Mild and Reversible Dehydration of Primary Amides with PdC12 in Aqueous Acetonitrile", Organic Letters vol. 7 No. 23, 5237-39 (2005).
Main et al, "High throughput synthesis of diverse 2,5-disubstituted indoles using titanium carbenoids bearing boronate functionality", Tetrahedron, 64(5):901-914 (2007).
Mainstone et al., "Tear meniscus measurement in the diagnosis of dry eye", Curr Eye Res, 1996; 15:653-661.
Mancini, M. et al., "RAD 001 (everolimus) prevents mTOR and Akt late re-activation in response to imatinib in chronic myeloid leukemia.", J. Cellular Biochemistry (2010) LNKD-PUBMED:20014066, XP-002673720 vol. 109, No. 2 (2010) pp. 320-328.
Mandal, "Cancer Classification," 2014. Available from: <http://www.news-medical.net/health/Cancer-Classification.aspx, 6 pages.
Manjula, et al., "Rapid Method of Converting Primary Amides to Nitriles and Nitriles to Primary Amides by ZnC12 using Microwaves under Different Reaction Conditions", Syn. Commun 37:1545-50 (2007).
Manning, et al., "The Protein Kinase Complement of the Human Genome", Science. 2002, 298(5600):1912-16 and 1933-34.
March, Jerry, Advanced Organic Chemistry: Reactions, Mechanisms, and Structure, 3rd ed., John Wiley & Sons:New York, pp. 845-855 (1985).
Marquardt et al., "Modification of tear film break-up time test for increased reliability" in Holly ed. The Preocular Tear Film inHealth, Disease and Contact Lens Wear. Lubbock, Texas: Dry Eye Institute, 1986:57-63.
Maruyama et al., "Effect of environmental conditions on tear dynamics in soft contact lens wearers", Invest Ophthalmol Vis Sci, 2004;45(8):2563-8.
Mathers et al., "Assessment of the tear film with tandem scanning confocal microscopy", Cornea, 1997;16:162-8.
Mathers et al., "Tear film changes associated with normal aging", Cornea, 1996; 15:229-334.
Mathers et al., "Tear flow and evaporation in patients with and without dry eye", Ophthalmology, 1996; 103:664-669.
Mathers et al., "Video imaging of the meibomian gland", Arch Ophthalmol, 1994;112:448-9.
Mathers, "Evaporation from the ocular surface", Exp Eye Res, 2004; 78:389-394.
Mayo Clinic. Available at: < http://www.mayoclinic.com/health/pancreatic-cancer/DS00357 >. 2 pages, retrieved from the Internet Apr. 3, 2013.
Mayo Clinic. Available at: < http://www.mayoclinic.com/health/prostate-cancer-prevention/MC00027 >. 3 pages, retrieved from the Internet Apr. 3, 2013.
Mayo Clinic. Available at: <http://www.mayoclinic.com/health/crohns-disease/DS00104/DSECTION=treatments-and-drugs> 6 pages, retrieved from the Internet May 27, 2013.
Mayo Clinic. Available at: <http://www.mayoclinic.com/health/multiple-sclerosis/DS00188/DSECTION=treatments-and-drugs>. 3 pages, retrieved from the Internet May 27, 2013.
Mayo Clinic. Available at: <http://www.mayoclinic.com/health/myasthenia-gravis/DS00375> 2 pages, retrieved from the Internet May 27, 2013.
Mayo Clinic. Available at: <http://www.mayoclinic.com/health/rheumatoid-arthritis/DS00020/DSECTION=treatments-and-drugs> 3 pages, retrieved from the Internet Jun. 26, 2013.
Mayo Clinic. Available at: <http://www.mayoclinic.org/diseases-conditions/type-1-diabetes/basics/prevention> 2014, 19 pages.
McNamara et al., "Fluorometry in contact lens research: The next step", Optom Vis Sci, 1998; 75:316-322.
MD Anderson Cancer Center. "Leukemia Prevention and Screening," 2014, 2 pages.
MD Anderson Cancer Center. "Myeloproliferative Disease Prevention and Screening," 2014, 2 pages.
Mengher et al., "Non-invasive tear film break-up time: sensitivity and specificity", Acta Ophthalmol (Copenh), 1986; 64(4):441-4.
Mesa, et al. "INCB018424, a Selective JAK 1/2 Inhibitor, Significantly Improves the Compromised Nutritional Status and Frank Cachexia in Patients with Myelofibrosis (MF)" Poster #1760 at the American Society of Hematology Annual Meeting (ASH), Dec. 6, 2008 (19 pages).
Mesa, et al., "Evaluating the serial use of the myelofibrosis symptom assessment form for measuring symptomatic improvement: Performance in 87 myelofibrosis patients on a JAK1 and JAK2 inhibitor (INCB018424) clinical trial", Cancer, (Nov. 1, 2011) vol. 117, No. 21, pp. 4869-4877.
Mesa, R. et al., "Emerging drugs for the therapy of primary and post essential thrombocythemia, post polycythemia vera myelofibrosis", Expert Opinion on Emerging Drugs England, vol. 14, No. 3 (2009) pp. 471-479.
Methods in Molecular Biology: vol. 225, Inflammation Protocols., Winyard, P.G. and Willoughby, D.A., Humana Press, 2003* too voluminous to provide.
Meydan et al., "Inhibition of acute lymphoblastic leukaemia by a Jak-2 inhibitor", Nature. Feb. 15, 1996;379(6566):645-8.
Miethchen, "Micelle-activated reactions. I. Micelle-activated iodination and partial dehalogenation of pyrazoles and 1,2,4-triazoles", Journal F. prakt. Chemie, Band 331, Heft 5, S. 799-805 (1989) (1 page abstract also provided).
Milici, A.J., et al., "Cartilage preservation by inhibition of Janus kinase 3 in two rodent models of rheumatoid arthritis", Arthritis Research & Therapy, 2008, 10:R14 (http://arthritis-research.com/content/10/1/R14) (9 pages).
Minegishi, et al., "Human Tyrosine Kinase 2 Deficiency Reveals Its Requisite Roles in Multiple Cytokine Signals Involved in Innate and Acquired Immunity", Immunity 25:745-55 (2006).
Mishchenko et al., "Treatment options for hydroxyurea-refractory disease complications in myeloproliferative neoplasms: JAK2 inhibitors, radiotherapy, splenectomy and transjugular intrahepatic portosystemic shunt", Eur J Haematol. Sep. 2010;85(3):192-9. Epub Jun. 2, 2010.
Mishima, et al., "Determination of tear volume and tear flow", Invest Ophthalmol, 1966; 5:264-276.
Mishima, S., "Some physiological aspects of the precorneal tear film", Arch Ophthalmol, 1965;73:233-241.
Mitsunobu, O., "The Use of Diethyl Axodicarboxylate and Triphenylphosphine in Synthesis and Transformation of Natural Products." Synthesis (1): 1-28 (1981).
Miyata, et al., "Stereospecific nucleophilic addition reactions to olefins.", J. Org. Chem. 56:6556-6564 (1991).
Miyaura et al., "Palladium-Catalyzed Cross-Coupling Reactions of Organoboron Compounds," Chem. Rev., 1995, 95, 2457-2483.
Miyoshi et al., "Interleukin-8 concentrations in conjunctival epithelium brush cytology samples correlate with neutrophil, eosinophil infiltration, and corneal damage", Cornea, 2001;20:743-7.
Moreland, et al. "A Randomized Placebo-Controlled Study of INCB018424, a Selective Janus Kinase 1&2 (JAK 1&2) Inhibitor in

(56) References Cited

OTHER PUBLICATIONS

Rheumatoid Arthritis (RA)" Presentation at the American College of Rheumatology meeting, Oct. 26, 2008. (20 pages).
Moriarty, et al., "The synthesis and SAR of 2-amino-pyrrolo[2,3-d]pyrimidines: A new class of Aurora-A kinase inhibitors", Bioorganic and Medicinal Chemistry Letters, 16(22), 5778-5783 (2006).
Mosby's Dictionary of Medicine, Nursing, & Health Professions, sicca complex, 2009, Elsevier, printed from http://www.credoreference.com/entry/ehsmosbymed/sicca_complex, 2 pages.
Mullighan, et al, "JAK mutations in high-risk childhood acute lymphoblastic leukemia", Proc Natl Acad Sci USA. 106:9414-8 (2009).
Naka T., "The paradigm of IL-6: from basic science to medicine", Arthritis Res. 2002;4 Suppl 3:S233-42. Epub May 9, 2002.
Nakagawara, Akira, "Trk receptor tyrosine kinases: A bridge between cancer and neural development." Cancer Letters, 169:107-114, 2001.
Nally et al., "Ocular discomfort and tear film break-up time in dry eye patients: A correlation", Invest Ophthalmol Vis Sci, 2000;41:4:1436 (Poster Presentation).
Naqvi, et al., "A potential role of ruxolitinib in leukemia", Expert Opinion on Investigational Drugs, (Aug. 2011) vol. 20, No. 8, pp. 1159-1166.
National Cancer Institute, "FDA Approval for Ruxolitinib Phosphate", http://www.cancer.gov/cancertopics/druginfo/fda-ruxolitinibphosphate posted Nov. 18, 2011 (3 pages).
Naus, et al., "6-(Het)ary1-7-Deazapurine Ribonucleosides as Novel Potent Cytostatic Agents", J. Med. Chem., 53(1):460-470 (2010).
Neidle, Stephen, Cancer Drug Design and Discovery, (Elsevier/Academic Press, 2008) pp. 427-431.
Nelson et al., "Tear film osmolality determination: an evaluation of potential errors in measurement" Curr Eye Res, Sep;5(9):677-81, 1986.
Neubauer, H., et al., "Jak2 Deficiency Defines an Essential Developmental Checkpoint in Definitive Hematopoiesis", Cell, 93(3): 397-409 (1998).
Nicholoff et al., "Recent Insights into the immunopathogenesis of psoriasis provide new therapeutic opportunities", J. Clin. Invest., 113; 1664-1675 (2004).
Nichols et al., "The lack of association between signs and symptoms in patients with dry eye disease", Cornea, vol. 23(8):762-770 (2004).
Nichols et al., "The repeatability of clinical measurements of dry eye", Cornea, vol. 23(3):272-85 (2004).
Nishio, et al., "Tyrosine kinase-dependent modulation by interferon-$\alpha$ of the ATP-sensitive K+ current in rabbit ventricular myocytes", FEBS Letters, (1999), 445, 87-91.
Nitta, et al., "Peptide-Titanium Complex as Catalyst for Asymmetric Addition of Hydrogen Cyanide to Aldehyde", J. Am. Chem. Soc., 1992, 114, 7969-75 (1992).
Norman, "Selective JAK1 inhibitor and selective Tyk2 inhibitor patents," *Expert Opinion*, Informa Healthcare. 2012, available at: <http://informahealthcare.com/dol/pdfplus/10.1517/13543776.2012.723693>.
Norn, M., "Quantitative tear ferning. Clinical investigations", Acta Ophthalmol (Copenh), Jun. 1994;72(3):369-72.
Notice of Allowance and Fee(s) Due dated Sep. 21, 2007 in connection with U.S. Appl. No. 11/313,394 (6 pages).
Notice of Hearing and Preliminary Report for EP Patent 1966202, dated Mar. 18, 2013 (7 pages).
Office Action (Non-final) dated Aug. 22, 2007 in connection with U.S. Appl. No. 11/115,702 (9 pages).
Office Action (Non-final) dated Dec. 3, 2007 in connection with U.S. Appl. No. 11/524,641 (13 pages).
Office Action (Non-final) dated Feb. 25, 2009 for U.S. Appl. No. 12/137,892 (13 pgs.)
Office Action (Final) dated Feb. 7, 2008 for U.S. Appl. No. 11/115,702 (5 pages).
Office Action (Final) dated Jan. 29, 2014 in U.S. Appl. No. 13/043,986, 10 pages.
Office Action (Final) dated Nov. 30, 2009 for U.S. Appl. No. 12/137,892 (9 pgs.).
Office Action (Non-final) dated Apr. 20, 2007 in connection with U.S. Appl. No. 11/313,394 (16 pages).
Office Action in U.S. Appl. No. 14/186,338, mailed May 5, 2014, 18 pages.
Office Action received for European Application No. 06 839 328.9 (Jan. 22, 2009) (5 pages).
Office Action received for Japanese Application No. 2008-545733 dated Oct. 11, 2011 (5 pages).
Office Action received for New Zealand Application No. 569015 dated Feb. 24, 2010 (2 pages).
Office Action received for Singapore Application No. 2008-04386-1 (Aug. 24, 2010).
Office Action received for Vietnamese Patent Application No. 01-2011-03188 dated Mar. 8, 2012 as translated by foreign associate (10 pages).
Office Action, Canadian Patent Office, Application No. 2,632,466, dated May 8, 2012 (3 pages).
Office Action, China, Patent Application No. 201080033308.6 dated Aug. 2, 2013, 10 pages.
Office Action, Eurasian Patent Office, prepared Feb. 5, 2010.
Office Action, European Patent Office, Application No. 06 839 328.9 mailed Oct. 21, 2010.
Office Action, European Patent Office, mailed Nov. 6, 2009.
Office Action, Mexico, Patent Appl. No. Mx/a/2008/007635 as received from foreign associate dated Jun. 15, 2010 (1 page).
Office Action, Mexico, Patent Appl. No. Mx/a/2008/007635 as received from foreign associate dated Nov. 13, 2009 (4 pages).
Office Action/Examination Report received for Pakistan Application No. 211/2009 dated Jan. 18, 2010 (1 page)
Oguz, et al., "The height and radius of the tear meniscus and methods for examining these parameters", Cornea, 2000;19:497-500.
Opposition for EP Patent 1966202, filed on Jun. 21, 2012 (30 pages).
Opposition for India Patent Application No. 2365/KOLNP/2008 dated Nov. 12, 2012 (received by Applicants from Indian associate on Apr. 17, 2013) 37 pages.
Opposition, Costa Rica, translation from Foreign Associate Dated Jun. 13, 2012, 6 pages.
Opposition, Costa Rica, translation from Foreign Associate Dated Nov. 20, 2013, 9 pages.
Opposition, Ecuador Patent Office, mailed Nov. 18, 2008 1 page letter from Foreign Associate enclosing the translation (5 pages) of the Opposition.
Ortmann, et al., "Janus kinases and signal transducers and activators of transcription: their roles in cytokine signaling, development and immunoregulation." Arthritis Res, 2(1): 16-32 (2000).
Ostojic et al., "Ruxolitinib for the treatment of myelofibrosis", Drugs of Today, (Nov. 2011) vol. 47, No. 11, pp. 817-827.
Ousler, et al., "Factors that influence the inter-blink interval (IBI) as measured by the ocular protection index (OPI)", Invest Ophthalmol Vis Sci 2001; 43: E-abstract 56 (Poster presentation) ARVO (2002) 2 pages, downloaded from http://abstracts.iov.s.org/cgi/content/abstract/43/12/56?maxtoshow on Aug. 14, 2009.
Palmer, et al., "Multiple roles of ephrins in morphogenesis, neuronal networking, and brain function." Genes & Dev., 17:1429-1450, 2003.
Pardanani A., "JAK2 inhibitor therapy in myeloproliferative disorders: rationale, preclinical studies and ongoing clinical trialsJAK2 inhibitor therapy in MPD", Leukemia 22, 23-30 (Jan. 2008).
Parganas, E., D. Wang, et al., "Jak2 is Essential for Signaling through a Variety of Cytokine Receptors", (1998). Cell, 93(3): 385-95.
Park et al., "Homogeneous Proximity Tyrosine Kinase Assays: Scintillation Proximity Assay versus Homogeneous Time-Resolved Fluorescense", Analytical Biochemistry, 1999, 269, 94-104.
Parks, "Tofacitinib and Other Kinase Inhibitors Offer New Approach to Treating Rheumatoid Arthritis," Rheumatologist, Jun. 2013, pp. 1-12 Available from: <http://www.the-rheumatologist.org/details/article/4871781/Tofacitinib_and_Other_Kinase_Inhibitors_Offer_New_Approach_to_Treating_Rheumatoi.html>, 12 pages.
Patani, et al., "Bioisosterism: A Rational Approach in Drug Design", Chem. Rev., 1996, 96, 3147-3176.

(56) References Cited

OTHER PUBLICATIONS

Patrick, Graham L., "An Introduction to medicinal chemistry" Oxford University Press Inc., New York, 1995 (31 pages) (cited in Opposition from India dated Nov. 12, 2012).
Pearce et al., "Spatial location studies on the chemical composition of human tear ferns", Ophthalmic Physiol Opt, (2000) vol. 20(4):306-13.
Pearce, et al., "An improved fluorophotometric method for tear turnover assessment", Optom Vis Sci, (2001) 78(1):30-36).
Pensyl et al., "The repeatability of tear mucus ferning grading", Optom Vis Sci, Aug. 1998;75(8):600-4.
Pernis, et al., "JAK-STAT signaling in asthma." J Clin Invest, 109(10): 1279-83 (2002).
Peters, K. G. et al., "Functional Significance of Tie2 Signaling in the Adult Vasculature", 2004, © The Endocrine Society (21 pages).
Pflugfelder, et al., "Evaluation of subjective assessments and objective diagnostic tests for diagnosing tear-film disorders known to cause ocular irritation", Cornea, 1998;17(1):38-56.
Pillonel, Christian, "Evaluation of phenylaminopyrimidines as antifungal protein kinase inhibitors", Pest Management Science, Wiley & Sons, vol. 61, Jun. 13, 2005 pp. 1069-1076.
Pirard, B. et al., "Classification of Kinase Inhibitors Using BCUT Descriptors", J. Chem. Inf. Comput. Sci., 2000, 40, 1431-1440.
Pisella et al., Flow cytometric analysis of conjunctival epithelium in ocular rosacea and keratoconjunctivitis sicca. Ophthalmology, 2000;107:1841-1849.
Pisella, et al., Conjunctival proinflammatory and proapoptotic effects of latanoprost, preserved timolol and unpreserved timolol: an ex vivo and in vitro study. Invest Ophthalmol Vis Sci, 2004;45:1360-1368).
Portnaya, et. al., "Azomethine dyes. IV. Indoaniline dyes derived from heterocyclic N-substituted 1-hydroxy-2-naphthamid", Ts Vses Nauchn Issled Kinofotoinst, Issue 40, (1960) pp. 106-108 (with English abstract 20 pages total).
Press Release dated Sep. 18, 2008: "Incyte's Topical JAK Inhibitor Demonstrates Positive Proof-of-Concept Results in Patients with Mild to Moderate Psoriasis" (4 pages).
Prezent, et al., "Boron chelates as intermediates in the synthesis of new functionalized pyridines and pyrimidines from a, a-dioxoketene aminals", Proceedings of the International Conference on the Chemistry of Boron, vol. 11 (2003) (abstract only—1 page).
Punwani et al., Poster/presentation, "Initial Efficacy and Safety of Topical INCYB018424 Cream, a Selective Janus Kinase 1&2 (JAK 1&2) Inhibitor in Psoriasis" 17th Congress of the European Academy of Dermatology and Venereology, Paris, France, Sep. 17, 2008 (15 pages).
Quesada et al, "One-pot conversion of activated alcohols into 1,1-dibromoalkenes and terminal alkynes using tandem oxidation processes with manganese dioxide", Tetrahedron, 62 (2006) 6673-6680.
Quintas-Cardama et al., "Preclinical characterization of the selective JAK1/2 inhibitor INCB018424: therapeutic implications for the treatment of myeloproliferative neoplasms", Blood First Edition Paper, prepublished online Feb. 3, 2010, American Society of Hematology; DOI 10.1182/blood-2009-04-214957, 115(15):3109-3117.
Ravin, L., "Preformulation", Remington's Pharmaceutical Sciences, 17th ed., Mack Publishing Company, Easton, Pa., 1985, Chapter 76, pp. 1409-1423.
Ren et al., "Compounds and Compositions as Protein Kinase Inhibitors," U.S. Appl. No. 60/578,491, filed Jun. 10, 2004 (56 pages).
Response and Amendment dated Aug. 25, 2009 to non-final Office Action for U.S. Appl. No. 12/137,892 (34 pgs.)
Response and Amendment in Reply to Action of Apr. 20, 2007 filed Jul. 17, 2007 for U.S. Appl. No. 11/313,394 (39 pages).
Response to Action of Aug. 22, 2007 dated Nov. 19, 2007, U.S. Appl. No. 11/115,702 (7 pages).
Response to Restriction Requirement dated May 29, 2007, U.S. Appl. No. 11/115,702 (8 pages).
Restriction Requirement dated Mar. 6, 2007 in connection with U.S. Appl. No. 11/115,702 (8 pages).
Roberts, Jr., et al., JAMA 292(17):2130-2140 (2004).
Robin et al., In vivo transillumination biomicroscopy and photography of meibomian gland dysfunction. Ophthalmology, 1985;92:1423-6.
Rodig, et al., "Disruption of the Jakl gene demonstrates obligatory and nonredundant roles of the Jaks in cytokine-induced biologic responses." Cell, 93(3): 373-83 (1998).
Rolando et al., "Tear mucus crystallization in children with cystic fibrosis", Ophthalmologica, 1988;197(4):202-6).
Rolando et al., "Tear mucus ferning test in keratoconjunctivitis sicca", Holly FJ, Lamberts DW, MacKeen DL (eds.): The preocular tear film in health, disease, and contact lens wear,. 1st Intern Tear Film Symposium. Lubbok (Texas, USA), Dry Eye Institute, 1986, 203-210.
Rolando et al., "The effect of hyperosmolarity on tear mucus ferning", Fortschr Ophthalmol, 1986;83:644-646.
Rolando et al., The Ocular Surface and Tear Film and Their Dysfuntion in Dry Eye Disease, Survey of Ophthalmology, Mar. 2001, vol. 45, Supplement 2, S203-S210.
Rolando, M. "Tear mucus ferning test in normal and keratoconjunctivitis sicca eyes." Chibret Int J Ophthalmol, 1984;2(4):32-41.
Roudebush et al., "Pharmacologic manipulation of a four day marine delayed type hyper sensitivity model", Agents Actions, 1993, 38(1-2):116-21.
Rousvoal, G. et al. "Janus kinase 3 inhibition with CP-690,550 prevents allograft vasculopathy", Transpl Int., 2006 19(12):1014-21.
Saemann, et al., "Prevention of CD40-triggered dendritic cell maturation and induction of T-cell hyporeactivity by targeting of Janus kinase 3." Am J Transplant, 3(11): 1341-9 (2003).
Saettone et al. "Ocular inserts for topical delivery," Advanced Drug Delivery Reviews, 16: 95-106, 1995.
Samanta et al., "Janus kinase 2: a critical target in chronic myelogenous leukemia", Cancer Res. Jul. 1, 2006;66(13):6468-72.
Sawada et al, "Increased Lipophilicity and Subsequent Cell Partitioning Decrease Passive Transcellular Diffusion of Novel, Highly Lipophilic Antioxidents", The Journal of Pharmacology and Experimental Therapeutics, 1999, No. 288, vol. 3, pp. 1317-1326, p. 1321, compound 26.
Schindler et al., "Hormones and Signaling: Cytokines and STAT Signaling", Adv Pharmacol. 2000; 47:113-74.
Schrader et al., "Animal Models of Dry Eye," Developmental Opthalmology, Karger 2008, 41, 298-312.
Scott, et al., "Jaks, STATs, Cytokines, and Sepsis." Clin Diagn Lab Immunol, 9(6): 1153-9 (2002).
Seefeld, et al, "Discovery of 5-pyrrolopyridinyl-2-thiophenecarboxamides as potent AKT kinase", Bioorganic & Medicinal Chemistry Letters, 19(8):2244-2248 (2009).
Seela, et al., "Synthesis of Pyrrolo[2,3-d]pyrimidine 2',3 '-Dideoxyribenucleosides Related to 2',3 '-Dideoxyadenosine and 2',3'-Dideoxgtuanosine and Inhibitory Activity of 5'-Triphosphates on HIV-1 Reverse Transcriptase", Helvetica Chimica, Acta, 1991, 74(3), 554-64.
Seki, "STAT3 and MAPK in human lung cancer tissues and suppression of oncogenic growth by JAB and dominant negative STAT3", Int J Oncol. 24(4):931-4 (2004).
Seto, et al. (2003). "Enhanced Th2 cell-mediated allergic inflammation in Tyk2-deficient mice." J Immunol, 170(2): 1077-83.
Shah et al., "Multiple BCR-ABL kinase domain mutations confer polyclonal resistance to the tyrosine kinase inhibitor imatinib (STI571) in chronic phase and blast crisis chronic myeloid leukemia." Cancer Cell, 2:117-125, Aug. 2002.
Shi, et al., "The pharmacokinetics, pharmacodynamics, and safety of orally dosed INCB018424 phosphate in healthy volunteers", Journal of Clinical Pharmacology, (Dec. 2011) vol. 51, No. 12, pp. 1644-1654.
Shimazaki et al., "Meibomian gland dysfunction in patients with Sjogren syndrome", Ophthalmology, 1998;105(8):1485-8.
Smith et al, "Basic pathogenic mechanisms operating in experimental model acute anterior uveitis," Immunology and Cell Biology, 1998, 76, 497-512.

(56) References Cited

OTHER PUBLICATIONS

Smolen, et al, "Effect of interleukin-6 receptor inhibition with tocilizumab in patients with rheumatoid arthritis (OPTION study): a double-blind, placebo-controlled, randomized trial", Lancet 371:987, 2008.

Sriram, K. et al., "Induction of gp130-related Cytokines and Activation of JAK2/STAT3 Pathway in Astrocytes Precedes Up-regulation of Glial Fibrillary Acidic Protein in the 1-Methyl-4-phenyl-1,2,3,6-tetrahydropyridine Model of Neurodengeneration", J. Biol. Chem., 2004, 279(19):19936-47. Epub Mar. 2, 2004.

Staerk, J., et. al., "JAK1 and Tyk2 activation by the homologous polycythemia vera JAK2 V617F mutation: cross-talk with IGF1 receptor", J Biol Chem., 280:41893-41899 (2005).

State Intellectual Property Office, PR China, Office Action, dated Sep. 3, 2010 Pat. Appl. No. 200680052750.7 (8 pages).

Stirewalt et al., "Predictors of relapse and overall survival in Philadelphia chromosome-positive acute lymphoblastic leukemia after transplantation", Biol Blood Marrow Transplant. Mar. 2003;9(3):206-12.

STN Search conducted Aug. 30, 2010 (17 pages).

STN Search conducted Jun. 24, 2011 (24 pages).

STN Search conducted Nov. 5, 2010 (5 pages).

STN Search conducted Nov. 9, 2010 (43 pages).

STN Search, Nov. 12, 2009 (180 pages).

STN Search, Oct. 20, 2009 (601 pages).

STN Search, Sep. 20, 2009 (864 pages).

Sullivan et al., "4th International Conference on the Lacrimal Gland, Tear Film & Ocular Surface and Dry Eye Syndromes, Nov. 20, 2004" (2 pages).

Takahashi, et al., "Solvent-Free Reaction Using Pmospwonium Salts: Chlorination of Hydroxyheteroaromatics and dehydration of Primary Amides", Heterocycles 68: 1973-1979 (2006).

Takano et al., "Inflammatory cells in brush cytology samples correlate with the severity of corneal lesions in atopic keratoconjunctivitis", Br J Ophthalmol, 2004;88:1504-5.

Takemoto, et al. (1997). "Proliferation of adult T cell leukemia/lymphoma cells is associated with the constitutive activation of JAK/STAT proteins." Proc. Natl Acad Sci U S A, 94(25): 13897-902.

Tan, et al, "Racemization processes at a quaternary carbon center in the context of the asymmetric Michael reaction", Tetrahedron Lett., 42(30):5021-5023 (2001).

Tang et al., "Knowledge-based design of 7-azaindoles as selective B-Raf inhibitors", Bioorganic & Medicinal Chemistry Letters (2008), 18(16):4610-4614.

Tasian et al., "Understanding the biology of CRLF2-overexpressing acute lymphoblastic leukemia", Critical Reviews in Oncogenesis, (2011) vol. 16, No. 1-2, pp. 13-24.

Tefferi, A. et al. "The Clinical Phenotype of Myelofibrosis Encompasses a Chronic Inflammatory State that is Favorably Altered by INCB018424, A Selective Inhibitor of JAK1/2" Poster #2804 at the American Society of Hematology Annual Meeting (ASH), Dec. 7, 2008, (18 pages).

Tefferi, Ayalew, "Primary myelofibrosis: 2012 update on diagnosis, risk stratification, and management", American Journal of Hematology, (Dec. 2011) vol. 86, No. 12, pp. 1017-1026.

Tefferi, et al., "Serious adverse events during ruxolitinib treatment discontinuation in patients with myelofibrosis", Mayo Clinic Proceedings, (Dec. 2011) vol. 86, No. 12, pp. 1188-1191.

Thompson, J., et al., "Photochemical Preparation of a Pyridone Containing Tetracycle: A Jak Protein Kinase Inhibitor", Bioorganic & Medicinal Chemistry Letters, 12 (2002) 1219-1223.

Tiffany et al., Meniscometry using the Tearscope-plus (ARVO abstract). Invest Ophthalmol Vis Sci, (2001);42, s37 (1 page).

Tiffany, J., "Refractive index of meibomian and other lipids", Curr Eye Res, (1986);5:887-9.

Ting, et al., "The Synthesis of substituted bipiperidine amide compounds as CCR3 antagonists", Bioorg. Med. Chem. Lett., vol. 15, No. 5, 1 (2005) pp. 1375-1378.

Toyonaga, "Blockade of constitutively activated Janus kinase/signal transducer and activator of transcription-3 pathway inhibits growth of human pancreatic cancer", Cancer Lett. 201(1):107-16 (2003).

Tsubota et al., "Brush cytology for the evaluation of dry-eye", Nippon Ganka Gakkai Zasshi, 1990a;94:224-30; in Japanese with English abstract.

Tsubota et al., "Conjunctival brush cytology", Acta Cytol, (1990) vol. 34(2):233-5.

Tsubota et al., "Detection by brush cytology of mast cells and eosinophils in allergic and vernal conjunctivitis"; Cornea, (1991) vol. 10(6):525-31.

Ueda et al., "1,2-Benzisoxazol-3-yl Diphenyl Phosphate: A New, Reactive Activating Agent for the Synthesis of Amides, Esters, and Peptides via Condensation", J. Org. Chem. 50:760-763 (1985).

van Best et al., "Measurement of basal tear turnover using a standardized protocol", Graefe's Arch Clin Exp Ophthalmol, 1995; 233:1-7.

van Bijsterveld, O., "Diagnostic tests in the sicca syndrome", Arch Ophthalmol, 1969;82:10-14.

Vannucchi A. et al., "The mTOR Inhibitor, RAD001, Inhibits the Growth of Cells From Patients with Myeloproliferative Neoplasms", Blood: ASH Annual Meeting Absracts, $51^{st}$ Annual Meeting of the American Society of Hematology, vol. 114, No. 22 (2009) 2 pages.

Vannucchi, A. et al, "InhibitorsofPI3K/Akt and/or mTOR Inhibit the Growth of Cells of Myeloproliferative Neoplasms and Synergize with JAK2 Inhibitor and Interferon", Blood, vol. 118, No. 21, pp. 1638-1639, XP008150742ASH Annual Meeting Abstract 3835 American Society of Hematology (2011).

Vannucchi, A. et al., "RAD001, an Inhibitor of mTOR, Shows Clinical Activity in a Phase I/II Study in Patients with Primary Myelofibrosis (PMF) and Post Polycythemia Vera/Essential Thrombocythemia Myelofibrosis (PPV/PET MF)", Blood, ASH Annual Meeting Abstracts 307, vol. 114, No. 22 (2009) 2 pages.

Vasilevsky, et al., "Ethyl Vinyl Ether—an Agent for Protection of the Pyrazole NH-Fragment. A Convenient Method for the Preparation of N-Unsubstituted 6Alkynylpyrazoles", Heterocycles, 60(4):879-886 (2003).

Verma, et al., "Jak family of kinases in cancer", Cancer and Metastasis Reviews, vol. 22, No. 4, 423-434, DOI: 10.1023/A:1023805715476 (2003).

Verstovsek, "Therapeutic Potential of JAK2 Inhibitors", Hematology Am Soc Hematol Educ Program, 2009:636-42.

Verstovsek, S. et al. "The JAK Inhibitor INCB018424 Demonstrates Durable and Marked Clinical Responses in Primary Myelofibrosis (PMF) and Post-Polycythemia/Essential Thrombocythemia Myelofibrosis (Post-PV/ET-MF)" Poster #1762 at the American Society of Hematology Annual Meeting (ASH), Dec. 6, 2008 (19 pages).

Verstovsek, S. et al. "The selective Janus kinase (JAK) inhibitor, INCB018424, shows efficacy in phase I/II trial in patients with primary myelofibrosis (PMF) and post polycythemia vera/essential thrombocythemia myelofibrosis (Post-PV/ET MF)" Abstract #0444, presented Saturday, Jun. 14, 2008 at the European Hematology Association, 13th Congress, Jun. 12-15, Copenhagen, Denmark (2 pages).

Verstovsek, S. et al. INCB18424, an Oral, Selective JAK2 Inhibitor, Shows Significant Clinical Activity in a Phase I/II Study in Patient with Primary Myelofibrosis (PMF) and Post Polycythemia Vera/Essential Thrombocythemia Myelofibrosis (Post-PV/ET MF), presentation at the American Society of Hematology 49th Annual Meeting and Exposition, Dec. 10, 2007 (16 pages).

Verstovsek, Srdan et al., "Characterization of JAKS V617F Allele Burden in Advanced Myelofibrosis (MF) Patients: No Change in V617F:Wt JAK2 Ratio in Patients with High Allele Burdens despite Profound Clinical Improvement Following Treatment with the JAKL Inhibitor, INCB018424," 50th ASH Annual Meeting and Exposition, Abstract No. 2802 (2008).

Vitali et al. "The European Community Study Group on diagnostic criteria for Sjogren's syndrome. Sensitivity and specificity of tests for ocular and oral involvement in Sjogren's syndrome." 1994; Ann Rheum Dis, 53(10): 637-47.

Wagh, et al., "Polymers used in ocular dosage form and drug delivery systems", Asian J. Pharm., pp. 12-17 (Jan. 2008).

(56) References Cited

OTHER PUBLICATIONS

WebMD. "Diabetes Health Center." Available at: < http://diabetes.webmd.com/guide/diabetestreatmen_care >. 3 pages, retrieved from the Internet May 28, 2013.
Webster's New World Medical Dictionary, Sjogren's syndrome, 2003, Wiley Publishing, printed fro http://www.credoreference.com/entry/webstermed/sjogren_s_syndrome, 2 pages.
Weiss, et al., "Evaluation of a Series of Naphthamides as Potent, Orally Active Vascular Endothelial Growth Factor Receptor-2 Tyrosine Kinase Inhibitors", J. Med Chem., 51:1668-1680 (2008).
Welch et al., "An approach to a more standardized method of evaluating tear film break-up time", Invest Ophthalmol Vis Sci, 2003; 2485/B324 (abstract only—2 pages).
White et al., "Human basic tear fluid osmolality. I. Importance of sample collection strategy", Acta Ophthalmol (Copenh), Aug;71(4):524-9, 1993.
Williams et al., "Carbohydrate Chemistry: Recent Advances", Chem. Rev. 81:589-636 (1981).
Williams, et al. "Initial Efficacy of INCB018424, a selective Janus Kinase1& 2 (JAK1&2) Inhibitor in Rheumatoid Arthritis (RA)," European League Against Rheumatism (EULAR) meeting presentation and abstract (Jun. 11-14, 2008, Paris, France). Annals Rheum Dis 67SII:62, 2008.
Wolf, et al., "Burger's Medicinal Chemistry and Drug Discovery", 5th Ed. Part I, pp. 975-977 (1995).
Wu et al., One-Pot Two-Step Microwave-Assisted Reaction in Construction 4,5-Disubstituted Pyrazolopyrimidines Organic Letters, 2003, 5(20), 3587-3590.
Xiaoyang et al., "Knockdown of STAT3 Expression by RNA Interference Inhibits the Induction of Breast Tumors in Immunocompetent Mice", Cancer Res Apr. 1, 2005 65; 2532.
Yamaoka et al., "Janus kinase (JAK) inhibitors in rheumatoid arthritis", Current Rheumatology Reviews, (Nov. 2011) vol. 7, No. 4, pp. 306-312.
Yang et al., "Constitutive NF-kB activation confers interleukin 6 (IL6) independence and resistance to dexamethasone and Janus kinase inhibitor INCB018424 in murine plasmacytoma cells", Journal of Biological Chemistry, (Aug. 12, 2011) vol. 286, No. 32, pp. 27988-27997.
Yao, et al. "Glucocorticoid-Induced Bone Loss in Mice Can Be Reversed by the Actions of Parathyroid Hormone and Risedronate on Different Pathways for Bone Formation and Mineralization", Arthritis and Rheumatism, 58(11):3485-3497 (2008).
Yao, et al., "Glucocorticoid Excess in Mice Results in Early Activation of Osteoclastogenesis and Adipogenesis and Prolonged Suppression of Osteogenesis", Arthritis and Rheumatism, 58(6), 1674-1686 (2008).
Ye et al., "The synthesis and the antitumor activity of 5,7-disubstituted pyrazolo [1,5-a] pyrimidines," Chinese J Med Chem., Feb. 28, 2007, 17(1):18-22.
Yokoi et al., "A newly developed video-meibography system featuring a newly designed probe", Jpn J Ophthalmol, 2007; 51: 53-6).
Yokoi et al., "Assessment of meibomian gland function in dry eye using meibometry", Arch Ophthalmol, 1999;117:723-9).
Yokoi et al., "Correlation of tear lipid layer interference patterns with the diagnosis and severity of dry eye", Am J Ophthalmol, 1996;122:818-24.
Yokoi et al., "Non-invasive methods of assessing the tear film", Exp Eye Res, 2004;78:399-407).
Yongjun et al., "Advances in research of tyrosine kinases inhibitor of vascular endothelial growth factor receptor," Chinese J New Drugs, Dec. 31, 2008, 17(7):544-550.
Yu, et al., "Constitutive activation of the Janus kinase-STAT pathway in T lymphoma overexpressing the Lck protein tyrosine kinase", J Immunol. 159(11):5206-10 (1997).
Zheng, et al., "Discovery of INCB108201PF-4178903, a potent, selective, and orally bioavailable dual CCR2 and CCR5 antagonist", Bioorganic & Medicinal Chemistry Letters 21 (2011) 1442-45.
Zoppellaro, et al., "A Multifunctional High-Spin Biradical Pyrazolylbipyridine-bisnitronylnitroxide", Org. Lett. 6(26):4929-4932 (2004).
Zou, et al., "Signaling Pathways Activated by Oncogenic Forms of Abl Tyrosine Kinase." Journal of Biological Chemistry, 274(26):18141-18144, 1999.
Beck et al., "Brief Report: Alleviation of Systemic Manifestations of Castleman's Disease by Monoclonal Anti-Interleukin-6 Antibody," N. Engl. J. Med., 1994, 330(9):602-605.
Brett et al., "Structural chemistry of polycyclic heteroaromatic compound. Part 4. Electronic structures of angular dithienopyridines," J Chem Soc, Perkin Trans 2, Jan. 1, 1994, 9:2045.
Chari et al., "Complete Remission Achieved with Single Agent CNTO 328, an Anti-IL-6 Monoclonal Antibody, in Relapsed and Refractory Myeloma," Clinical Lymphoma, Myeloma & Leukemia, 2013, 13(3):333-337.
Chemical encyclopedia, vol. 1, pp. 242-243, publication "Soviet Encyclopedia," Moscow, 1988.
Choy et al., "Therapeutic Benefit of Blocking Interleukin-6 Activity With an Anti-Interleukin-6 Receptor Monoclonal Antibody in Rheumatoid Arthritis," Arthritis & Rheumatism, 2002, 46(12) 3143-3150.
Claridge; Bioorganic and Medicinal Chemistry Letters, 2008, 18,2793-2798.
Cottet and Schlosser, "Three Chloro(trifluoromethyl)pyridines as Model Substrates for Regioexhaustive Functionalization," Eur J Org Chem, 2004, 18:3793-3798.
Dorwald; "Side Reactions in Organic Synthesis: A Guide to Successful Synthesis Design" 2005 Wiley-VCH Verlag GmbH & Co. KGaA, Wienheim, chapter 1, 32 pages.
Fayad et al., "Interleukin-6 and interleukin-10 levels in chronic lymphocytic leukemia: correlation with phenotypic characteristics and outcome," Blood, Jan. 2001, 97(1): 256-263.
Forbes et al., "Synthesis and evaluation of a series of aryl [e] fused pyrazolo [4,3-c]pyridines with potential anxiolytic activity," J Medicinal Chem., Jan. 1, 1990, 33(9):2640-2645.
Gaestel et al., "Targeting innate immunity protein kinase signalling in inflammation," Nat Rev Drug Discov., Jun. 2009, 8(6):480-499.
Gilchrist et al., "5H-2-Pyrindines from 2-Bromocyclopentene-1-carboxaldehyde," Tetrahedron, Jan. 1, 1995, pp. 9119-9126.
Goodman, et al., "IL-6 Signaling in Psoriasis Prevents Immune Suppression by Regulatory T Cells," J. Immunol., Sep. 2009, 183: 3170-3176.
Grossman, et al., "Interleukin 6 is expressed in high levels in psoriatic skin and stimulates proliferation of cultured human keratinocytes," Proc. Natl. Acad., Sci. USA, Aug. 1989, 86: 6367-6371.
Hickenbottom "Reactions of organic compounds," State Scientific-Technical Publishing Association, Chemical Literature Section, Moscow, 1939, pp. 360-362.
International Preliminary Report on Patentability for PCT/US2013/041601, issued Nov. 18, 2014, 7 pages.
International Search Report in International Application No. PCT/US2013/041601, mailed Sep. 3, 2013, 3 pages.
International Search Report and Written Opinion in International Application No. PCT/US2013/067794, mailed Dec. 17, 2013, 14 pages.
Kurzrock et al., "A Phase I, Open-Label Study of Siltuximab, an Anti-IL-6 Monoclonal Antibody, in Patients with B-cell Non-Hodgkin Lymphoma, Multiple Myeloma, or Castleman Disease," Clin. Cancer Res., published online May 9, 2013, 39 pages.
Kurzrock et al., "Serum Interleukin 6 Levels Are Elevated in Lymphoma Patients and Correlate with Survival in Advanced Hodgkin's Disease and with B Symptoms," Cancer Res., May 1993, 52: 2118-2122.
Lima and Barreiro, "Bioisosterism: a useful strategy for molecular modification and drug design," Curr Med Chem. 2005;12(1):23-49.
Maxson et al., "Oncogenic CSF3R Mutations in Chronic Neutrophilic Leukemia and Atypical CML," N. Engl. J. Med., 2013, 368(19):1781-1790.
Neuner, et al., J. Invest. Dermatol. 1991, 97, 27-33.
Nishimoto et. al., "Improvement in Castleman's disease by humanized anti-interleukin-6 receptor antibody theraphy," Blood, 2000, 95(1):56-61.

(56) References Cited

OTHER PUBLICATIONS

Panteli et al., "Serum interleukin (IL)-1, IL-2, sIL-2Ra, IL-6 and thrombopoietin levels in patients with chronic myeloproliferative diseases," British Journal of Haematology, 2005, 130, 709-715.
Pedranzini, et al., Cancer Res., 66(19):9714-9721 (2006).
Punwani, Naresh, et al. "Efficacy and safety of topical INCB018424, a selective Janus kinase 1 & 2 (JAK1&2) inhibitor in psoriasis." Journal of the American Academy of Dermatology. vol. 60, No. 3, 360 Park Avenue South, New York, NY 10010-1710 USA: Mosby-Elsevier, 2009.
Search Report in TW Application No. 100117866, dated Dec. 2014, 1 page.
Sonbol et al., "Comprehensive review of JAK inhibitors in myeloproliferative neoplasms," Therapeutic Advances in Hematology, 2013, 4(1): 15-35.
Song et al. "JAK1 Activates STAT3 Activity in Non-Small-Cell Lung Cancer cells and IL-6 Neutralizing Antibodies can Suppress JAK1-STAT3 Signaling," Mol Cancer Ther., Mar. 2011, 10(3): 481-494.
Strassmann et al., "Suramin Interferes with Interleukin-6 Receptor Binding in Vitro and Inhibits Colon-26-mediated Experimental Cancer Cachexia in Vivo," J. Clin. Invest., Nov. 1993, 92: 2152-2159.
Tamura et al., "Involvement of Human Interleukin 6 in Experimental Cachexia Induced by a Human Uterine Cervical Carcinoma Xenograft," Clin. Cancer Res., Nov. 1995, 1: 1353-1358.
Trikha et al., "Targeted anti-interleukin-6 monoclonal antibody therapy for cancer: a review of the rationale and clinical evidence," Clinical Cancer Research, 2003, 9: 4653-4665.
van Rhee et al., "Anti-Interleukin-6 Monoclonal man's Disease," J. Clin. Oncol., 2010, 28(23):3701-3708.
Vaillant et al., "Turbidity of pulpy fruit juice: A key factor for predicting cross-flow microfiltration performance," J Membrane Sci., 2008, 325:404-412.
Vanhoutte, Arthritis Rheum 64.10 (2012): S1051-1.
Verstovsek, et al., Blood (ASH Annual Meeting Abstracts) 2007 110: Abstract 558.
Verstovsek, et al., Blood (ASH Annual Meeting Abstracts) 2009 114: Abstract 311.
Verstovsek, et al., Blood (ASH Annual Meeting Abstracts) 2010 116: Abstract 313.
Xiong, "Inhibition of JAK1, 2/STAT3 Signaling Induces Apoptosis, Cell Cycle Arrest, and Reduces Tumor Cell Invasion in Colorectal Cancer Cells," Neoplasia, Mar. 2008, 10(3): 287-297.
Yamamura et al., "Circulating interleukin-6 levels are elevated in adult T-cell leukaemia/lymphoma patients and correlate with adverse clinical features and survival," Br. J. Haematol., 1998, 100: 129-134.
Younes, J. Clin. Oncol., 30(33):1461-1467 (2012).

PROCESSES AND INTERMEDIATES FOR MAKING A JAK INHIBITOR

CROSS-REFERENCE TO RELATED APPLICATIONS

This application is a divisional of U.S. application Ser. No. 14/197,701, filed Mar. 5, 2014, which claims the benefit of U.S. Provisional Appl. No. 61/773,659, filed Mar. 6, 2013, each of which is incorporated herein by reference in its entirety.

TECHNICAL FIELD

This invention relates to processes and intermediates for making {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, useful in the treatment of diseases related to the activity of Janus kinases (JAK) including inflammatory disorders, autoimmune disorders, cancer, and other diseases.

BACKGROUND

Protein kinases (PKs) regulate diverse biological processes including cell growth, survival, differentiation, organ formation, morphogenesis, neovascularization, tissue repair, and regeneration, among others. Protein kinases also play specialized roles in a host of human diseases including cancer. Cytokines, low-molecular weight polypeptides or glycoproteins, regulate many pathways involved in the host inflammatory response to sepsis. Cytokines influence cell differentiation, proliferation and activation, and can modulate both pro-inflammatory and anti-inflammatory responses to allow the host to react appropriately to pathogens. Signaling of a wide range of cytokines involves the Janus kinase family (JAKs) of protein tyrosine kinases and Signal Transducers and Activators of Transcription (STATs). There are four known mammalian JAKs: JAK1 (Janus kinase-1), JAK2, JAK3 (also known as Janus kinase, leukocyte; JAKL; and L-JAK), and TYK2 (protein-tyrosine kinase 2).

Cytokine-stimulated immune and inflammatory responses contribute to pathogenesis of diseases: pathologies such as severe combined immunodeficiency (SCID) arise from suppression of the immune system, while a hyperactive or inappropriate immune/inflammatory response contributes to the pathology of autoimmune diseases (e.g., asthma, systemic lupus erythematosus, thyroiditis, myocarditis), and illnesses such as scleroderma and osteoarthritis (Ortmann, R. A., T. Cheng, et al. (2000) *Arthritis Res* 2(1): 16-32).

Deficiencies in expression of JAKs are associated with many disease states. For example, Jak1−/− mice are runted at birth, fail to nurse, and die perinatally (Rodig, S. J., M. A. Meraz, et al. (1998) *Cell* 93(3): 373-83). Jak2−/− mouse embryos are anemic and die around day 12.5 postcoitum due to the absence of definitive erythropoiesis.

The JAK/STAT pathway, and in particular all four JAKs, are believed to play a role in the pathogenesis of asthmatic response, chronic obstructive pulmonary disease, bronchitis, and other related inflammatory diseases of the lower respiratory tract. Multiple cytokines that signal through JAKs have been linked to inflammatory diseases/conditions of the upper respiratory tract, such as those affecting the nose and sinuses (e.g., rhinitis and sinusitis) whether classically allergic reactions or not. The JAK/STAT pathway has also been implicated in inflammatory diseases/conditions of the eye and chronic allergic responses.

Activation of JAK/STAT in cancers may occur by cytokine stimulation (e.g. IL-6 or GM-CSF) or by a reduction in the endogenous suppressors of JAK signaling such as SOCS (suppressor or cytokine signaling) or PIAS (protein inhibitor of activated STAT) (Boudny, V., and Kovarik, J., *Neoplasm.* 49:349-355, 2002). Activation of STAT signaling, as well as other pathways downstream of JAKs (e.g., Akt), has been correlated with poor prognosis in many cancer types (Bowman, T., et al. *Oncogene* 19:2474-2488, 2000). Elevated levels of circulating cytokines that signal through JAK/STAT play a causal role in cachexia and/or chronic fatigue. As such, JAK inhibition may be beneficial to cancer patients for reasons that extend beyond potential anti-tumor activity.

JAK2 tyrosine kinase can be beneficial for patients with myeloproliferative disorders, e.g., polycythemia vera (PV), essential thrombocythemia (ET), myeloid metaplasia with myelofibrosis (MMM) (Levin, et al., *Cancer Cell, vol.* 7, 2005: 387-397). Inhibition of the JAK2V617F kinase decreases proliferation of hematopoietic cells, suggesting JAK2 as a potential target for pharmacologic inhibition in patients with PV, ET, and MMM.

Inhibition of the JAKs may benefit patients suffering from skin immune disorders such as psoriasis, and skin sensitization. The maintenance of psoriasis is believed to depend on a number of inflammatory cytokines in addition to various chemokines and growth factors (JCI, 113:1664-1675), many of which signal through JAKs (*Adv Pharmacol.* 2000; 47:113-74).

JAK1 plays a central role in a number of cytokine and growth factor signaling pathways that, when dysregulated, can result in or contribute to disease states. For example, IL-6 levels are elevated in rheumatoid arthritis, a disease in which it has been suggested to have detrimental effects (Fonesca, J. E. et al., Autoimmunity Reviews, 8:538-42, 2009). Because IL-6 signals, at least in part, through JAK1, antagonizing IL-6 directly or indirectly through JAK1 inhibition is expected to provide clinical benefit (Guschin, D., N., et al Embo J 14:1421, 1995; Smolen, J. S., et al. Lancet 371:987, 2008). Moreover, in some cancers JAK1 is mutated resulting in constitutive undesirable tumor cell growth and survival (Mullighan C G, Proc Natl Acad Sci USA. 106:9414-8, 2009; Flex E., et al. J Exp Med. 205:751-8, 2008). In other autoimmune diseases and cancers elevated systemic levels of inflammatory cytokines that activate JAK1 may also contribute to the disease and/or associated symptoms. Therefore, patients with such diseases may benefit from JAK1 inhibition. Selective inhibitors of JAK1 may be efficacious while avoiding unnecessary and potentially undesirable effects of inhibiting other JAK kinases.

Selective inhibitors of JAK1, relative to other JAK kinases, may have multiple therapeutic advantages over less selective inhibitors. With respect to selectivity against JAK2, a number of important cytokines and growth factors signal through JAK2 including, for example, erythropoietin (Epo) and thrombopoietin (Tpo) (Parganas E, et al. Cell. 93:385-95, 1998). Epo is a key growth factor for red blood cells production; hence a paucity of Epo-dependent signaling can result in reduced numbers of red blood cells and anemia (Kaushansky K, NEJM 354:2034-45, 2006). Tpo, another example of a JAK2-dependent growth factor, plays a central role in controlling the proliferation and maturation of megakaryocytes—the cells from which platelets are produced (Kaushansky K, NEJM 354:2034-45, 2006). As such, reduced Tpo signaling would decrease megakaryocyte numbers (megakaryocytopenia) and lower circulating platelet counts (thrombocytopenia). This can result in undesirable and/or uncontrollable bleeding. Reduced inhibition of other JAKs, such as JAK3 and Tyk2, may also be desirable as humans lacking functional version of these kinases have been shown to suffer from numerous maladies such as severe-combined immunodeficiency or hyperimmunoglobulin E syndrome (Minegishi, Y, et al. Immunity 25:745-55, 2006; Macchi P, et al. Nature. 377:65-8, 1995). Therefore a JAK1 inhibitor with reduced affinity for other JAKs would have significant advantages over a less-selective inhibitor with respect to reduced side effects involving immune suppression, anemia and thrombocytopenia.

Due to the usefulness of JAK inhibitors, there is a need for development of new processes for making JAK inhibitors. This invention is directed towards this need and others.

SUMMARY

JAK inhibitors are described in US 2011/0224190, which is incorporated herein by reference in its entirety, including {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, which is depicted below as Formula I.

I

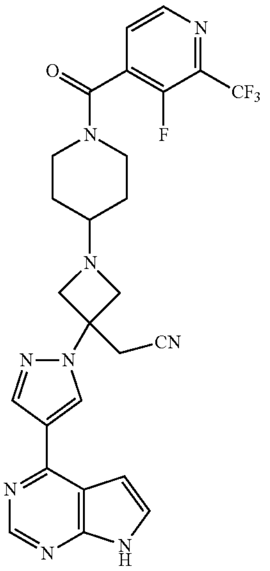

The present invention provides, inter alia, processes and intermediates for making the compound of Formula I. In particular, the present invention provides processes of making a compound of Formula II:

II

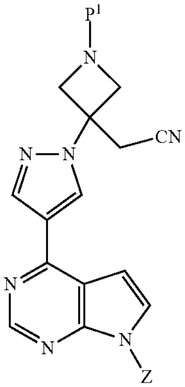

comprising reacting a compound of Formula III:

III

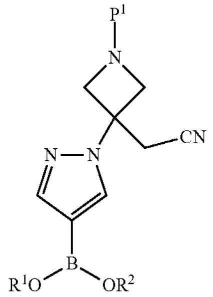

with a compound of Formula IV:

IV

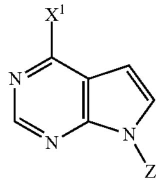

under Suzuki coupling conditions to form a compound of Formula II, wherein:

Z is H or a protecting group;

$P^1$ is a protecting group;

$X^1$ is halo; and $R^1$ and $R^2$ are each independently H or $C_{1-6}$ alkyl; or $R^1$ and $R^2$, together with the two oxygen atoms to which they are attached and the boron atom to which the oxygen atoms are attached, form a 5- to 6-membered heterocycloalkyl ring, which is optionally substituted with 1, 2, 3, or 4 $C_{1-4}$ alkyl groups.

The present invention further provides processes for making a compound of Formula IIa:

IIa

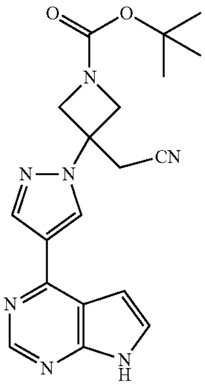

comprising reacting a compound of Formula IIIa:

IIIa

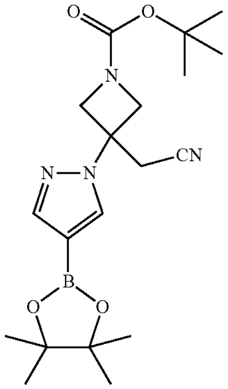

with a compound of Formula IVa:

IVa

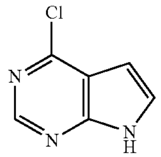

under Suzuki coupling conditions to form a compound of Formula IIa, wherein the Suzuki coupling conditions comprise heating a reaction mixture comprising the compound of Formula IIIa, the compound of Formula IVa, [1,1'-bis(dicyclohexylphosphino)ferrocene]dichloropalladium (II), cesium fluoride, and a solvent component, wherein the solvent component comprises water and tert-butanol.

The process further comprises a process for deprotecting a compound of Formula II or IIa to form a compound of Formula V:

V

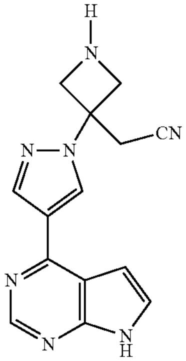

or salt thereof.

The present invention also provides a process further comprising reacting a compound of Formula V, or a salt thereof, with a compound of Formula VI:

VI

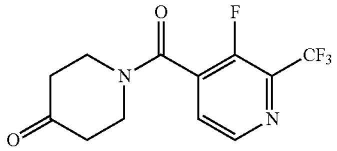

in the presence of a reducing agent to form a compound of Formula I:

I

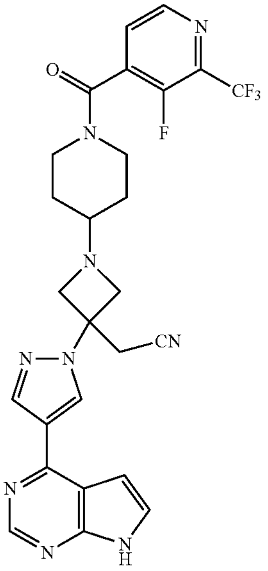

or a salt thereof.

The present invention further provides compounds of Formula VII:

VII

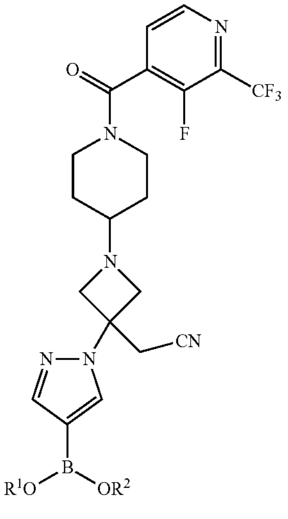

or salts thereof; wherein:

$R^1$ and $R^2$ are each independently H or $C_{1-6}$ alkyl; or $R^1$ and $R^2$, together with the two oxygen atoms to which they are attached and the boron atom to which the oxygen atoms are attached, form a 5- to 6-membered heterocycloalkyl ring, which is optionally substituted with 1, 2, 3, or 4 $C_{1-4}$ alkyl groups.

The present invention further provides processes for making a compound of Formula VII, comprising reacting a compound of Formula VIII:

VIII

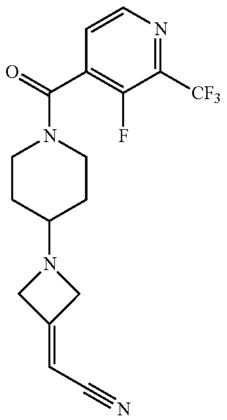

with a compound of Formula IX:

IX

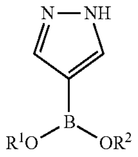

in the presence of a coupling agent to form a compound of Formula VII; wherein:

$R^1$ and $R^2$ are each independently H or $C_{1-6}$ alkyl; or $R^1$ and $R^2$, together with the two oxygen atoms to which they are attached and the boron atom to which the oxygen atoms are attached, form a 5- to 6-membered heterocycloalkyl ring, which is optionally substituted with 1, 2, 3, or 4 $C_{1-4}$ alkyl groups.

The present invention further provides processes of making a compound of Formula VIIa, comprising reacting a compound of Formula VIII, or a salt thereof:

VIII

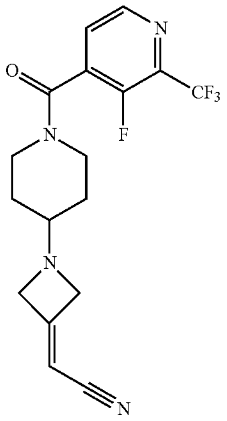

with a compound of Formula IXa:

IXa

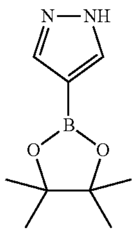

in the presence of a coupling agent to form a compound of Formula VIIa:

VIIa

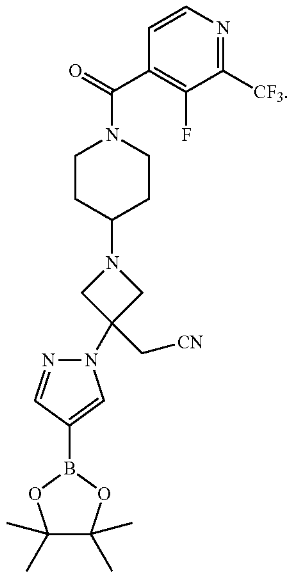

The present invention further provides processes for making a compound of Formula I, comprising reacting the compound of Formula VII or VIIa with a compound of Formula IVa:

IVa

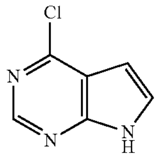

under Suzuki coupling conditions to form a compound of Formula I:

I

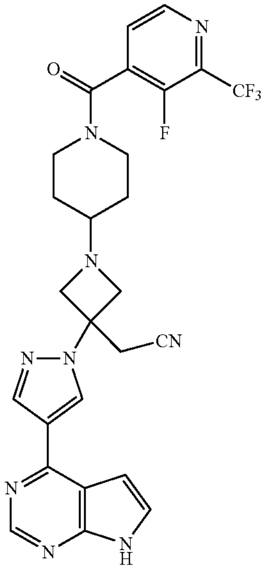

wherein the Suzuki coupling conditions comprise heating a reaction mixture comprising the compound of Formula VII or VIIa, the compound of Formula IVa, a Suzuki coupling catalyst, a base and a solvent component.

The present invention further provides a compound of Formula VIII:

VIII

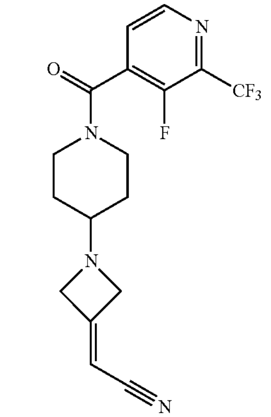

or a salt thereof.

The present invention further provides processes of preparing a compound of Formula VIII, or a salt thereof, comprising reacting a compound of Formula VI:

VI

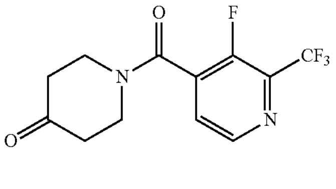

with a compound of Formula X:

X

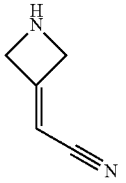

or a salt thereof, in the presence of a reducing agent.

The present invention further provides processes of preparing a compound of Formula III, comprising reacting a compound of Formula X:

X

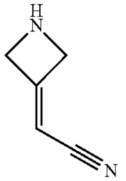

or salt thereof, with a compound of Formula IX:

IX

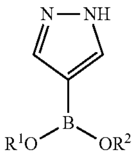

in the presence of a coupling agent to form a compound of Formula III, or salt thereof; wherein:

$R^1$ and $R^2$ are each independently H or $C_{1-6}$ alkyl; or $R^1$ and $R^2$, together with the two oxygen atoms to which they are attached and the boron atom to which the oxygen atoms are attached, form a 5- to 6-membered heterocycloalkyl ring, which is optionally substituted with 1, 2, 3, or 4 $C_{1-4}$ alkyl groups.

DETAILED DESCRIPTION

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "n-membered" where n is an integer typically describes the number of ring-forming atoms in a moiety where the number of ring-forming atoms is n. For example, piperidinyl is an example of a 6-membered heterocycloalkyl ring and 1,2,3,4-tetrahydro-naphthalene is an example of a 10-membered cycloalkyl group.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R.

As used herein, the phrase "optionally substituted" means unsubstituted or substituted. As used herein, the term "substituted" means that a hydrogen atom is removed and replaced by a substituent. It is understood that substitution at a given atom is limited by valency.

As used herein, the term "alkyl", employed alone or in combination with other terms, refers to a saturated hydrocarbon group that may be straight-chain or branched. In some embodiments, the alkyl group contains 1 to 12, 1 to 8, or 1 to 6 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, n-heptyl, n-octyl, and the like. In some embodiments, the alkyl moiety is methyl, ethyl, n-propyl, isopropyl, n-butyl, isobutyl, tert-butyl, n-pentyl, isopentyl, neopentyl, n-hexyl, or 2,4,4-trimethylpentyl. In some embodiments, the alkyl moiety is methyl.

As used herein, the terms "halo" and "halogen", employed alone or in combination with other terms, refer to fluoro, chloro, bromo, and iodo. In some embodiments, halo is chloro, bromo, or iodo. In some embodiments, halo is chloro.

As used herein, "heterocycloalkyl" refers to an non-aromatic monocyclic ring including cyclized alkyl or alkenyl groups where one or more of the ring-forming carbon atoms is replaced by a heteroatom such as an O, N, S, or B atom.

The processes described herein can be monitored according to any suitable method known in the art. For example, product formation can be monitored by spectroscopic means, such as nuclear magnetic resonance spectroscopy (e.g., $^1H$ or $^{13}C$), infrared spectroscopy, or spectrophotometry (e.g., UV-visible); or by chromatography such as high performance liquid chromatography (HPLC) or thin layer chromatography (TLC) or other related techniques.

As used herein, the term "reacting" is used as known in the art and generally refers to the bringing together of chemical reagents in such a manner so as to allow their interaction at the molecular level to achieve a chemical or physical transformation. In some embodiments, the reacting involves two reagents, wherein one or more equivalents of second reagent are used with respect to the first reagent. The reacting steps of the processes described herein can be conducted for a time and under conditions suitable for preparing the identified product.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., Protective Groups in Organic Synthesis, 4d. Ed., Wiley & Sons, 2007, which is incorporated herein by reference in its entirety. Adjustments to the protecting groups and formation and cleavage methods described herein may be adjusted as necessary in light of the various substituents.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

Suitable solvents can include halogenated solvents such as carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, α,α,α-trifluorotoluene, 1,2-dichloroethane, 1,2-dibromoethane, hexafluorobenzene, 1,2,4-trichlorobenzene, 1,2-dichlorobenzene, chlorobenzene, fluorobenzene, mixtures thereof and the like.

Suitable ether solvents include: dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, t-butyl methyl ether, mixtures thereof and the like.

Suitable protic solvents can include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol.

Suitable aprotic solvents can include, by way of example and without limitation, tetrahydrofuran (THF), N,N-dimethylformamide (DMF), N,N-dimethylacetamide (DMA), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable hydrocarbon solvents include benzene, cyclohexane, pentane, hexane, toluene, cycloheptane, methylcyclohexane, heptane, ethylbenzene, m-, o-, or p-xylene, octane, indane, nonane, or naphthalene.

The reactions of the processes described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures). "Elevated temperature" refers to temperatures above room temperature (about 22° C.).

The reactions of the processes described herein can be carried out in air or under an inert atmosphere. Typically, reactions containing reagents or products that are substantially reactive with air can be carried out using air-sensitive synthetic techniques that are well known to the skilled artisan.

In some embodiments, preparation of compounds can involve the addition of acids or bases to affect, for example, catalysis of a desired reaction or formation of salt forms such as acid addition salts.

Example acids can be inorganic or organic acids. Inorganic acids include hydrochloric acid, hydrobromic acid, sulfuric acid, phosphoric acid, and nitric acid. Organic acids include formic acid, acetic acid, propionic acid, butanoic acid, benzoic acid, 4-nitrobenzoic acid, methanesulfonic acid, p-toluenesulfonic acid, benzenesulfonic acid, tartaric acid, trifluoroacetic acid, propiolic acid, butyric acid, 2-butynoic acid, vinyl acetic acid, pentanoic acid, hexanoic acid, heptanoic acid, octanoic acid, nonanoic acid and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include sodium and potassium salts of methyl, ethyl, n-propyl, i-propyl, n-butyl, t-butyl, trimethylsilyl and cyclohexyl substituted amides.

The intermediates and products may also include salts of the compounds disclosed herein. As used herein, the term "salt" refers to a salt formed by the addition of an acceptable acid or base to a compound disclosed herein. In some embodiments, the salts are pharmaceutically acceptable salts. As used herein, the phrase "pharmaceutically acceptable" refers to a substance that is acceptable for use in pharmaceutical applications from a toxicological perspective and does not adversely interact with the active ingredient. Pharmaceutically acceptable salts, including mono- and bi-salts, include, but are not limited to, those derived from organic and inorganic acids such as, but not limited to, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in their entireties.

Upon carrying out preparation of compounds according to the processes described herein, the usual isolation and purification operations such as concentration, filtration, extraction, solid-phase extraction, recrystallization, chromatography, and the like may be used, to isolate the desired products.

In some embodiments, the compounds described herein and salts thereof, are substantially isolated. By "substantially isolated" is meant that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or a salt thereof. Methods for isolating compounds and their salts are routine in the art.

Processes for preparing some of the intermediates can be found in U.S. Provisional Patent Appl. No. 61/531,896, filed Sep. 7, 2011, U.S. patent application Ser. No. 12/687,623, filed Jan. 14, 2010, and U.S. patent application Ser. No. 13/043,986, filed Mar. 9, 2011, each of which is incorporated herein by reference in its entirety.

Processes and Intermediates

The present invention provides, inter alia, processes and intermediates for making the compound of Formula I. Accordingly, in one aspect, the present invention provides a process, comprising:

reacting a compound of Formula III:

III

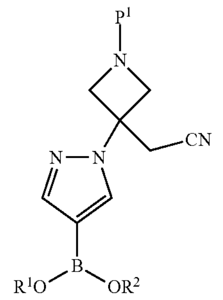

with a compound of Formula IV:

IV

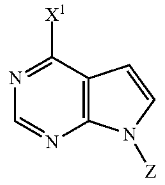

under Suzuki coupling conditions to form a compound of Formula II:

II

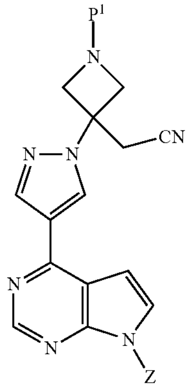

wherein:

Z is H or a protecting group;

$P^1$ is a protecting group;

$X^1$ is halo; and $R^1$ and $R^2$ are each independently H or $C_{1-6}$ alkyl; or $R^1$ and $R^2$, together with the two oxygen atoms to which they are attached and the boron atom to which the oxygen atoms are attached, form a 5- to 6-membered heterocycloalkyl ring, which is optionally substituted with 1, 2, 3, or 4 $C_{1-4}$ alkyl groups.

In some embodiments, $P^1$ is tert-butoxycarbonyl. Appropriate $P_1$ protecting groups include, but are not limited to the protecting groups for amines delineated in Wuts and Greene, Protective Groups in Organic Synthesis, 4th ed., John Wiley & Sons: New Jersey, pages 696-887 (and, in particular, pages 872-887) (2007), which is incorporated herein by reference in its entirety. In some embodiments, $P_1$ is benzyloxycarbonyl (Cbz), 2,2,2-trichloroethoxycarbonyl (Troc), 2-(trimethylsilyl)ethoxycarbonyl (Teoc), 2-(4-trifluoromethylphenylsulfonyl)ethoxycarbonyl (Tsc), t-butoxycarbonyl (BOC), 1-adamantyloxycarbonyl (Adoc), 2-adamantylcarbonyl (2-Adoc), 2,4-dimethylpent-3-yloxycarbonyl (Doc), cyclohexyloxycarbonyl (Hoc), 1,1-dimethyl-2,2,2-trichloroethoxycarbonyl (TcBOC), vinyl, 2-chloroethyl, 2-phenylsulfonylethyl, allyl, benzyl, 2-nitrobenzyl, 4-nitrobenzyl, diphenyl-4-pyridylmethyl, N',N'-dimethylhydrazinyl, methoxymethyl, t-butoxymethyl (Bum), benzyloxymethyl (BOM), or 2-tetrahydropyranyl (THP). In some embodiments, $P_1$ is tri($C_{1-4}$ alkyl) silyl (e.g., tri(isopropyl)silyl). In some embodiments, $P_1$ is 1,1-diethoxymethyl. In some embodiments, $P_1$ is 2-(trimethylsilyl)ethoxymethyl (SEM). In some embodiments, $P_1$ is N-pivaloyloxymethyl (POM).

In some embodiments,

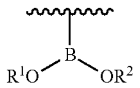

is

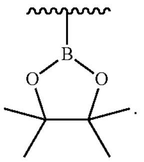

In some embodiments, $R^1$ and $R^2$ are each independently methyl or ethyl. In some embodiments, $R^1$ and $R^2$ are each methyl. In some embodiments, $R^1$ and $R^2$ are each ethyl.

In some embodiments, $X^1$ is chloro.

In some embodiments, Z is H.

In some embodiments, the compound of Formula III has Formula IIIa:

IIIa

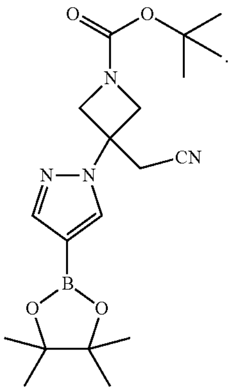

In some embodiments, the compound of Formula IV has Formula IVa:

IVa

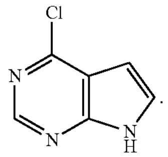

In some embodiments, the Suzuki coupling conditions comprise heating a reaction mixture comprising the compound of Formula III, the compound of Formula IV, a Suzuki coupling catalyst, a base and a solvent component.

The Suzuki coupling reaction in the processes described herein can be initiated using a number of different known Suzuki catalysts, including palladium(0) and palladium(II) catalysts and performed under conditions known in the art (see, e.g., Miyaura and Suzuki, *Chem. Rev.* 1995, 95, 2457-2483, which is hereby incorporated in its entirety). In some embodiments, "in the presence of a catalyst" may refer to the addition of a catalyst precursor, which is present in some other form during the reaction cycle. In some embodiments, the palladium catalyst is $Pd(PPh_3)_4$ and $Pd(dppf)_2Cl_2$. In some embodiments, the catalyst is [1,1'-bis(dicyclohexylphosphino)ferrocene]dichloropalladium (II). In some embodiments, the palladium catalyst is [1,1'-bis(dicyclohexylphosphino)ferrocene]dichloropalladium (II) ("Pd-127"), tetrakis(triphenylphosphine)palladium(0), or tetrakis (tri(o-tolyl)phosphine)palladium(0). In some embodiments, the palladium catalyst is tetrakis(triphenylphosphine) palladium(0). In some embodiments, the palladium catalyst loading is from about $1\times10^{-4}$ to about 0.1 equivalents. In some embodiments, the palladium catalyst loading is from about 0.0010 to about 0.0015 equivalents.

In some embodiments, the base is cesium fluoride. In some embodiments, the cesium fluoride is present in 3 equivalents or more (e.g., 3.5 equivalents) based on the compound of Formula IV. In some embodiments, the solvent component can include tert-butanol and water. In some embodiments, the tert-butanol and water are present in a 1:1 volume ratio.

In some embodiments, compounds of Formula III and IV are present in about a 1:1 molar ratio.

In some embodiments, the solvent component comprises water and an organic solvent. In some embodiments, the organic solvent is 1,4-dioxane, 1-butanol, t-butanol, 1,2-dimethoxyethane (DME), DMF, 2-propanol, toluene or ethanol, or a combination thereof.

In some embodiments, the base is an inorganic base. In some embodiments, the base is an organic base. In some embodiments, the base is an alkali metal carbonate (e.g., $K_2CO_3$ or $Na_2CO_3$). In some embodiments, the base is potassium carbonate ($K_2CO_3$) or CsF. In some embodiments, two to five equivalents of base (e.g., $K_2CO_3$, CsF) are used.

In some embodiments, the Suzuki coupling reaction is conducted at a temperature of about 80° C. to about 100° C. In some embodiments, the reaction is carried out for two to twelve hours. In some embodiments, the compound of Formula II or IIa can be optionally isolated from aqueous work-up of the Suzuki coupling reaction mixture or directly used.

In another aspect, the present invention provides processes for making a compound of Formula IIa, comprising reacting a compound of Formula IIIa:

IIIa

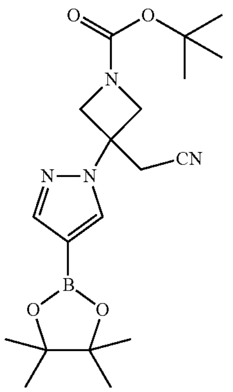

with a compound of Formula IVa:

IVa

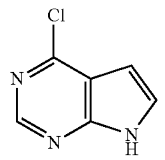

under Suzuki coupling conditions to form a compound of Formula IIa:

IIa

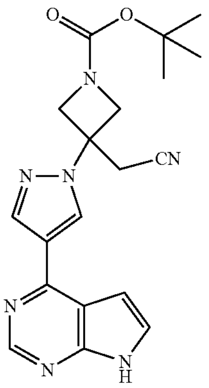

wherein the Suzuki coupling conditions comprise heating a reaction mixture comprising the compound of Formula IIIa, the compound of Formula IVa, [1,1'-bis(dicyclohexylphosphino)ferrocene]dichloropalladium (II), cesium fluoride, and a solvent component, wherein the solvent component comprises water and tert-butanol.

The processes for making a compound of Formula II or IIa further can comprise deprotecting the compound of Formula II to form a compound of Formula V:

V

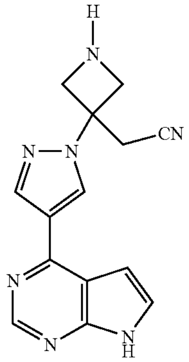

or salt thereof. The deprotecting can include reacting the compound of Formula II or Formula IIa with hydrochloric acid (e.g., about 5 M hydrochloric acid) in a second solvent component (e.g., water and dichloromethane). In some embodiments, the hydrochloric acid is used in an amount of 5 to 8 equivalents based on the compound of Formula II. As used herein, "second" in the phrase "second solvent component" is used to differentiate the solvent component from other solvent components used in earlier or later steps of the process and does not indicate that two solvents must be present.

In some embodiments, the compound of Formula V, or a salt thereof, is further reacted with a compound of Formula VI:

VI

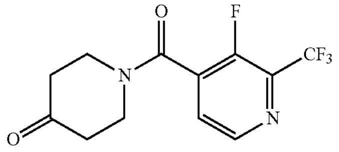

in the presence of a reducing agent to form a compound of Formula I:

I

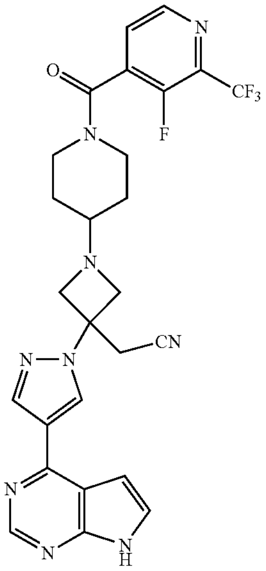

or a salt thereof.

In some embodiments, the reducing agent is sodium cyanoborohydride or sodium triacetoxyborohydride. In some embodiments, the reducing agent is sodium triacetoxyborohydride. In some embodiments, greater than 1 equivalent (e.g., 2 equivalents) of sodium triacetoxyborohydride is used based on the compound of Formula V.

The reducing agent can be any reducing agent suitable for use in reductive amination, including various borohydride and borane reducing agents, such as those in Ellen W. Baxter and Allen B. Reitz, Reductive Aminations of Carbonyl Compounds with Borohydride and Borane Reducing Agents, Organic Reactions, Chapter 1, pages 1-57 (Wiley, 2002), which is incorporated herein by reference in its entirety. Non-limiting classes of appropriate reducing agents include borohydride, cyanoborohydride, tri($C_{1-4}$ acyl)oxyborohydride (e.g., triacetoxyborohydride derivatives), 9-borobicyclo[3.3.1]nonane hydride, tri($C_{1-4}$ alkyl)borohydride, and disopinocampteylcyanoborohydride derivatives, amino boranes, borane-pyridine complex, and alkylamine boranes. Non-limiting examples of appropriate reducing agents include sodium cyanoborohydride, sodium triacetoxyborohydride, sodium cyano-9-borobicyclo[3.3.1]nonane hydride, tetrabutylammonium cyanoborohydride, cyanoborohydride on a solid support, tetramethylammonium triacetoxyborohydride, sodium triacetoxyborohydride, lithium triethylborohydride, lithium tri(sec-butyl)borohydride, sodium disopinocampteylcyanoborohydride, catechol borane, borane tetrahydrofuran, sodium borohydride, potassium borohydride, lithium borohydride, palladium in the presence of hydrogen gas, 5-ethyl-2-methylpyridine borane (PEMB), 2-picoline borane or polymer-supported triacetoxyborohydride. In some embodiments, any of the aforementioned, and preferably sodium cyanoborohydride, is used in combination with a titanium (IV) additive, dehydrating agent, or a zinc halide additive. In some embodiments, the reducing agent is a tetra ($C_{1-4}$ alkyl)ammonium cyanoborohydride or triacetoxyborohydride, an alkali metal cyanoborohydride or triacetoxyborohydride, or an alkaline earth cyanoborohydride or triacetoxyborohydride. In some embodiments, the reducing agent is an alkali metal cyanoborohydride. In some embodiments, the reducing agent is selected from sodium cyanoborohydride and sodium triacetoxyborohydride. In some embodiments, the reducing agent is sodium triacetoxyborohydride. As used herein, a titanium (IV) additive is a Lewis acid containing a titanium (IV) metal (e.g., titanium tetrachloride, titanium isopropoxide, titanium ethoxide, and the like).

In some embodiments, the compound of Formula V, or salt thereof, is 2-(3-(4-(7H-pyrrolo[2,3-d]pyrimidin-4-yl)-1H-pyrazol-1-yl)azetidin-3-yl)acetonitrile dihydrochloride salt. In some embodiments, the reacting is carried out in the presence of at least two equivalents of a second base. In some embodiments, the second base is a tertiary amine (e.g., triethylamine). As used herein, "second" in the phrase "second base" is used to differentiate the base from other bases used in earlier or later steps of the process and does not indicate that two bases must be present.

In some embodiments, greater than 1 equivalent of the compound of Formula VI is used based on the compound of Formula V, or salt thereof.

In some embodiments, reaction of a compound of Formula V, or salt thereof, with a compound of Formula VI is performed in dichloromethane solvent.

In some embodiments, the process further comprises reacting the compound of Formula I with adipic acid to form the adipate salt of the compound of Formula I In another aspect, the present invention provides a compound of Formula VII:

VII

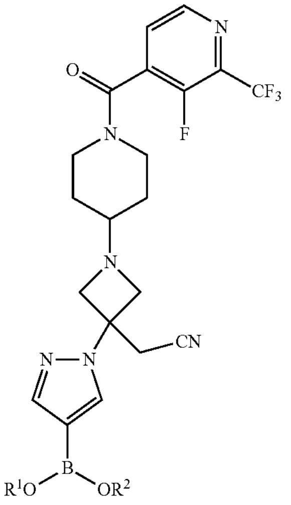

or a salt thereof; wherein:

$R^1$ and $R^2$ are each independently H or $C_{1-6}$ alkyl; or $R^1$ and $R^2$, together with the two oxygen atoms to which they are attached and the boron atom to which the oxygen atoms are attached, form a 5- to 6-membered heterocycloalkyl ring, which is optionally substituted with 1, 2, 3, or 4 $C_{1-4}$ alkyl groups.

In some embodiments, the compound of Formula VII is a compound having Formula VIIa:

VIIa

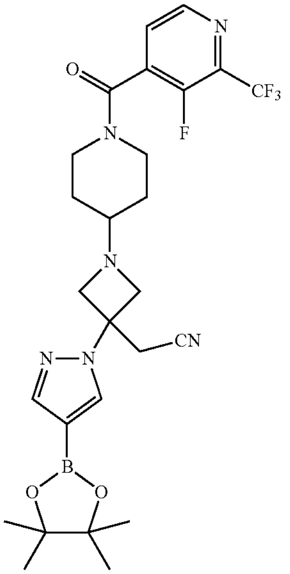

or a salt thereof.

The present invention further provides a process for making a compound of Formula VII, comprising reacting a compound of Formula VIII:

VIII

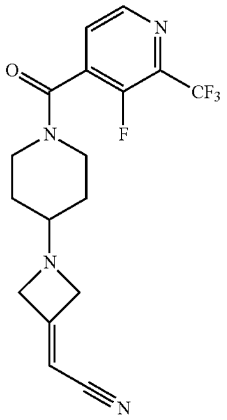

with a compound of Formula IX:

IX

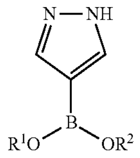

in the presence of a coupling agent to form a compound of Formula VII; wherein:

$R^1$ and $R^2$ are each independently H or $C_{1-6}$ alkyl; or $R^1$ and $R^2$, together with the two oxygen atoms to which they are attached and the boron atom to which the oxygen atoms are attached, form a 5- to 6-membered heterocycloalkyl ring, which is optionally substituted with 1, 2, 3, or 4 $C_{1-4}$ alkyl groups.

In some embodiments, the process includes a process of making a compound of Formula VIIa comprise reacting a compound of Formula VIII:

VIII

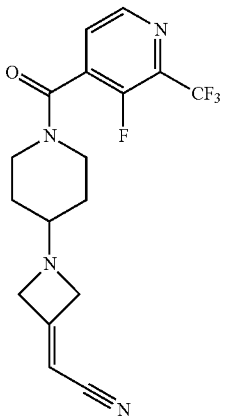

with a compound of Formula IXa:

IXa

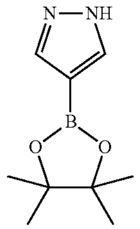

in the presence of a coupling agent to form a compound of Formula VIIa:

VIIa

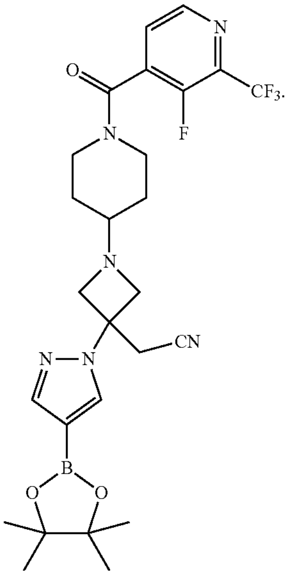

In some embodiments, the coupling agent for the reaction of a compound of Formula VIII, with a compound of Formula IX or a compound of Formula IXa, is 1,8-diazabicyclo[5,4,0]undecene. In some embodiments, about 1.05 to about 1.2 equivalents (e.g., 1.12 equivalents) of coupling agent is used based on the compound of Formula VIII.

In some embodiments, reacting of the compound of Formula VIII with the compound of Formula IX or IXa is conducted in a solvent component comprising acetonitrile, at a temperature of about 40° C. to about 60° C. In some embodiments, 1 to 1.2 equivalents of the compound of Formula IX or IXa are used based on the compound of Formula VIII.

In some embodiments, the compound of Formula VIIa is reacted with a compound of Formula IVa:

IVa

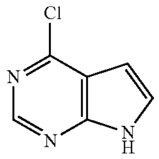

under Suzuki coupling conditions to form a compound of Formula I:

I

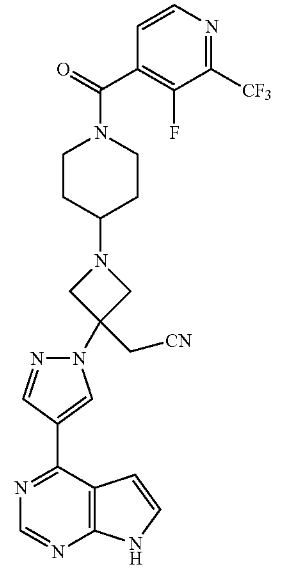

wherein the Suzuki coupling conditions comprise heating a reaction mixture comprising the compound of Formula VIIa, the compound of Formula IVa, a Suzuki coupling catalyst, a base and a second solvent component.

In some embodiments, the Suzuki catalyst is tetrakis(triphenylphosphine)palladium(0). In some embodiments, the base (e.g., sodium bicarbonate) is present in 4 equivalents or more (e.g., 5 equivalents) based on the compound of Formula VII or VIIa.

In some embodiments, the second solvent component comprises 1,4-dioxane and water, e.g., a 1:1 volume ratio.

In some embodiments, the compounds of Formula VII or VIIa, and IVa, are present in about a 1:1 molar ratio.

In some embodiments, the compound of Formula VIIa is reacted with a compound of Formula IVa:

IVa

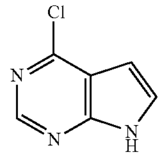

under Suzuki coupling conditions to form a compound of Formula I:

I

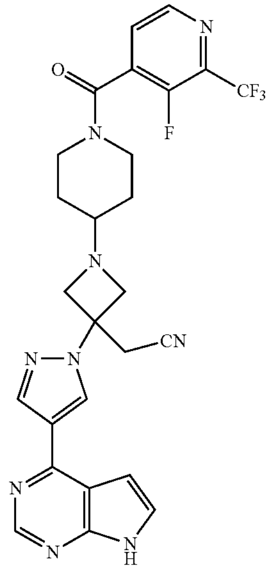

wherein the Suzuki coupling conditions comprise heating a reaction mixture comprising the compound of Formula VIIa, the compound of Formula IVa, tetrakis(triphenylphosphine) palladium(0), sodium bicarbonate, and a second solvent component, wherein the second solvent component comprises water and 1,4-dioxane.

In another aspect, the present invention further provides a compound of Formula VIII:

VIII

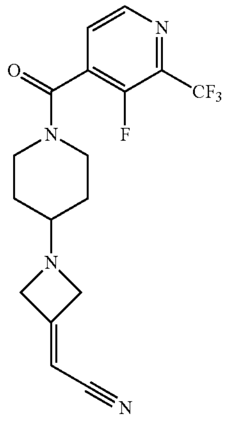

or a salt thereof.

In yet another aspect, the present invention provides a process of preparing a compound of Formula VIII, or a salt thereof, comprising reacting a compound of Formula VI:

VI

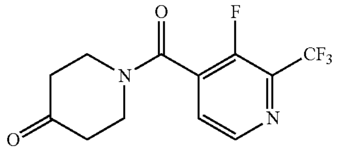

with a compound of Formula X:

X

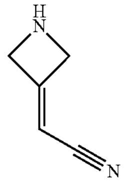

or a salt thereof, in the presence of a reducing agent.

In some embodiments, the compound of Formula X, or salt thereof, is 2-(azetidin-3-ylidene)acetonitrile hydrochloride.

In some embodiments, reacting a compound of Formula VI and a compound of Formula X, or salt thereof, is in the presence of a reducing agent such as sodium cyanoborohydride or sodium triacetoxyborohydride (e.g., sodium triacetoxyborohydride). About 1.5 to about 2.5 equivalents (e.g., 2 equivalents) of the reducing agent can be used based on the compound of Formula X, or salt thereof.

In some embodiments, reacting the compound of Formula VI and the compound of Formula X, or salt thereof, is conducted in a solvent component comprising dichloromethane.

In yet another aspect, the present invention features a compound of Formula III:

III

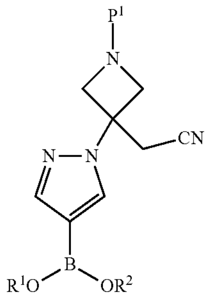

or a salt thereof; wherein:

$R^1$ and $R^2$ are each independently H or $C_{1-6}$ alkyl; or $R^1$ and $R^2$, together with the two oxygen atoms to which they are attached and the boron atom to which the oxygen atoms are attached, form a 5- to 6-membered heterocycloalkyl ring, which is optionally substituted with 1, 2, 3, or 4 $C_{1-4}$ alkyl groups.

In some embodiments, the compound of Formula III is compound having Formula IIIa:

IIIa

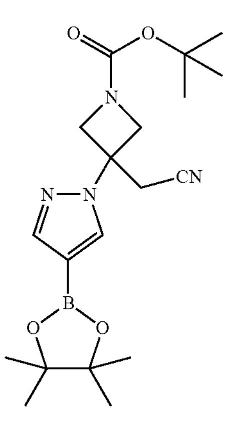

or a salt thereof.

In another aspect, the present invention features a process of preparing a compound of Formula III, comprising reacting a compound of Formula X:

X

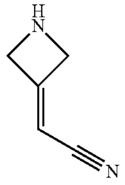

or a salt thereof, with a compound of Formula IX:

IX

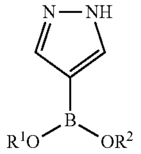

in the presence of a coupling agent to form a compound of Formula III, or a salt thereof; wherein:

$R^1$ and $R^2$ are each independently H or $C_{1-6}$ alkyl; or $R^1$ and $R^2$, together with the two oxygen atoms to which they are attached and the boron atom to which the oxygen atoms are attached, form a 5- to 6-membered heterocycloalkyl ring, which is optionally substituted with 1, 2, 3, or 4 $C_{1-4}$ alkyl groups.

In some embodiments, the coupling agent used in reacting a compound of Formula X, or salt thereof, with a compound of Formula IX is 1,8-diazabicyclo[5,4,0]undecene. In some embodiments, 0.1 to 0.2 equivalent of coupling agent is used based on the compound of Formula X, or salt thereof.

In some embodiments, the reacting of the compound of Formula X, or salt thereof, with the compound of Formula IX is conducted in a solvent component comprising isopropyl alcohol, for example, at a temperature of about 70° C. to about 90° C.

In some embodiments, 1 to 1.1 equivalents of the compound of Formula IX are used based on the compound of Formula X, or salt thereof.

In yet another aspect, the present invention features a process of preparing a compound of Formula IIIa, comprising reacting a compound of Formula X:

X

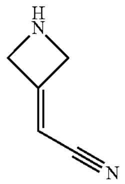

with a compound of Formula IXa:

IXa

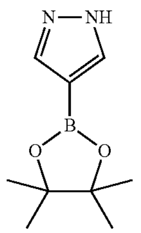

in the presence of a coupling agent to form a compound of Formula III.

In some embodiments, the coupling agent used in reacting a compound of Formula X with a compound of Formula IXa is 1,8-diazabicyclo[5,4,0]undecene. In some embodiments, 0.1 to 0.2 equivalent of coupling agent is used based on the compound of Formula X.

In some embodiments, the reacting of the compound of Formula X with the compound of Formula IXa is conducted in a solvent component comprising isopropyl alcohol, for example, at a temperature of about 70° C. to about 90° C.

In some embodiments, 1 to 1.1 equivalents of the compound of Formula IXa are used based on the compound of Formula X.

Uses

The compound of Formula I, {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, is an inhibitor of JAK (e.g., JAK1, JAK2). JAK inhibitors are useful in treating various JAK-associated diseases or disorders. Examples of JAK-associated diseases include diseases involving the immune system including, for example, organ transplant rejection (e.g., allograft rejection and graft versus host disease). Further examples of JAK-associated diseases include autoimmune diseases such as multiple sclerosis, rheumatoid arthritis, juvenile arthritis, psoriatic arthritis, type I diabetes, lupus, psoriasis, inflammatory bowel disease, ulcerative colitis, Crohn's disease, myasthenia gravis, immunoglobulin nephropathies, myocarditis, autoimmune thyroid disorders, chronic obstructive pulmonary disease (COPD), and the like. In some embodiments, the autoimmune disease is an autoimmune bullous skin disorder such as pemphigus vulgaris (PV) or bullous pemphigoid (BP).

Further examples of JAK-associated diseases include allergic conditions such as asthma, food allergies, eszematous dermatitis, contact dermatitis, atopic dermatitis (atopic eczema), and rhinitis. Further examples of JAK-associated diseases include viral diseases such as Epstein Barr Virus (EBV), Hepatitis B, Hepatitis C, HIV, HTLV 1, Varicella-Zoster Virus (VZV) and Human Papilloma Virus (HPV).

Further examples of JAK-associated disease include diseases associated with cartilage turnover, for example, gouty arthritis, septic or infectious arthritis, reactive arthritis, reflex sympathetic dystrophy, algodystrophy, Tietze syndrome, costal athropathy, osteoarthritis deformans endemica, Mseleni disease, Handigodu disease, degeneration resulting from fibromyalgia, systemic lupus erythematosus, scleroderma, or ankylosing spondylitis.

Further examples of JAK-associated disease include congenital cartilage malformations, including hereditary chrondrolysis, chrondrodysplasias, and pseudochrondrodysplasias (e.g., microtia, enotia, and metaphyseal chrondrodysplasia). Further examples of JAK-associated diseases or conditions include skin disorders such as psoriasis (for example, psoriasis vulgaris), atopic dermatitis, skin rash, skin irritation, skin sensitization (e.g., contact dermatitis or allergic contact dermatitis). For example, certain substances including some pharmaceuticals when topically applied can cause skin sensitization. In some embodiments, co-administration or sequential administration of at least one JAK inhibitor of the invention together with the agent causing unwanted sensitization can be helpful in treating such unwanted sensitization or dermatitis. In some embodiments, the skin disorder is treated by topical administration of at least one JAK inhibitor of the invention.

Further examples of JAK-associated diseases or conditions include those characterized by solid tumors (e.g., prostate cancer, renal cancer, hepatic cancer, pancreatic cancer, gastric cancer, breast cancer, lung cancer, cancers of the head and neck, thyroid cancer, glioblastoma, Kaposi's sarcoma, Castleman's disease, uterine leiomyosarcoma, melanoma etc.), hematological cancers (e.g., lymphoma, leukemia such as acute lymphoblastic leukemia (ALL), acute myelogenous leukemia (AML) or multiple myeloma), and skin cancer such as cutaneous T-cell lymphoma (CTCL) and cutaneous B-cell lymphoma. Example CTCLs include Sezary syndrome and mycosis fungoides. Other examples of JAK-associated diseases or conditions include pulmonary arterial hypertension.

Other examples of JAK-associated diseases or conditions include inflammation-associated cancers. In some embodiments, the cancer is associated with inflammatory bowel disease. In some embodiments, the inflammatory bowel disease is ulcerative colitis. In some embodiments, the inflammatory bowel disease is Crohn's disease. In some embodiments, the inflammation-associated cancer is colitis-associated cancer. In some embodiments, the inflammation-associated cancer is colon cancer or colorectal cancer. In some embodiments, the cancer is gastric cancer, gastrointestinal carcinoid tumor, gastrointestinal stromal tumor (GIST), adenocarcinoma, small intestine cancer, or rectal cancer.

JAK-associated diseases can further include those characterized by expression of: JAK2 mutants such as those having at least one mutation in the pseudo-kinase domain (e.g., JAK2V617F); JAK2 mutants having at least one mutation outside of the pseudo-kinase domain; JAK1 mutants; JAK3 mutants; erythropoietin receptor (EPOR) mutants; or deregulated expression of CRLF2.

JAK-associated diseases can further include myeloproliferative disorders (MPDs) such as polycythemia vera (PV), essential thrombocythemia (ET), myelofibrosis with myeloid metaplasia (MMM), primary myelofibrosis (PMF), chronic myelogenous leukemia (CML), chronic myelomonocytic leukemia (CMML), hypereosinophilic syndrome (HES), systemic mast cell disease (SMCD), and the like. In some embodiments, the myeloproliferative disorder is myelofibrosis (e.g., primary myelofibrosis (PMF) or post polycythemia vera/essential thrombocythemia myelofibrosis (Post-PV/Post-ET MF)). In some embodiments, the myeloproliferative disorder is post-essential thrombocythemia myelofibrosis (Post-ET MF). In some embodiments, the myeloproliferative disorder is post polycythemia vera myelofibrosis (Post-PV MF). Other examples of JAK-associated diseases or conditions include ameliorating the dermatological side effects of other pharmaceuticals by administration of the compound of the invention. For example, numerous pharmaceutical agents result in unwanted allergic reactions which can manifest as acneiform rash or related dermatitis. Example pharmaceutical agents that have such undesirable side effects include anti-cancer drugs such as gefitinib, cetuximab, erlotinib, and the like. The compounds of the invention can be administered systemically or topically (e.g., localized to the vicinity of the dermatitis) in combination with (e.g., simultaneously or sequentially) the pharmaceutical agent having the undesirable dermatological side effect. In some embodiments, the compound of the invention can be administered topically together with one or more other pharmaceuticals, where the other pharmaceuticals when topically applied in the absence of a compound of the invention cause contact dermatitis, allergic contact sensitization, or similar skin disorder. Accordingly, compositions of the invention include topical formulations containing the compound of the invention and a further pharmaceutical agent which can cause dermatitis, skin disorders, or related side effects. Further JAK-associated diseases include inflammation and inflammatory diseases. Example inflammatory diseases include sarcoidosis, inflammatory diseases of the eye (e.g., iritis, uveitis, scleritis, conjunctivitis, or related disease), inflammatory diseases of the respiratory tract (e.g., the upper respiratory tract including the nose and sinuses such as rhinitis or sinusitis or the lower respiratory tract including bronchitis, chronic obstructive pulmonary disease, and the like), inflammatory myopathy such as myocarditis, and other inflammatory diseases. In some embodiments, the inflammation disease of the eye is blepharitis.

Further JAK-associated diseases include ischemia reperfusion injuries or a disease or condition related to an inflammatory ischemic event such as stroke or cardiac arrest, endotoxin-driven disease state (e.g., complications after bypass surgery or chronic endotoxin states contributing to chronic cardiac failure), anorexia, cachexia, fatigue such as that resulting from or associated with cancer, restenosis, sclerodermitis, fibrosis, conditions associated with hypoxia or astrogliosis such as, for example, diabetic retinopathy, cancer, or neurodegeneration, and other inflammatory diseases such as systemic inflammatory response syndrome (SIRS) and septic shock.

Other JAK-associated diseases include gout and increased prostate size due to, e.g., benign prostatic hypertrophy or benign prostatic hyperplasia, as well as bone resorption diseases such as osteoporosis or osteoarthritis, bone resorption diseases associated with: hormonal imbalance and/or hormonal therapy, autoimmune disease (e.g. osseous sarcoidosis), or cancer (e.g. myeloma).

Further JAK-associated diseases include a dry eye disorder. As used herein, "dry eye disorder" is intended to encompass the disease states summarized in a recent official report of the Dry Eye Workshop (DEWS), which defined dry eye as "a multifactorial disease of the tears and ocular surface that results in symptoms of discomfort, visual disturbance, and tear film instability with potential damage to the ocular surface. It is accompanied by increased osmolarity of the tear film and inflammation of the ocular surface." Lemp, "The Definition and Classification of Dry Eye Disease: Report of the Definition and Classification Subcommittee of the International Dry Eye Workshop", *The Ocular Surface,* 5(2), 75-92 April 2007, which is incorporated herein by reference in its entirety. In some embodiments, the dry eye disorder is selected from aqueous tear-deficient dry eye (ADDE) or evaporative dry eye disorder, or appropriate combinations thereof. In some embodiments, the dry eye disorder is Sjogren syndrome dry eye (SSDE). In some embodiments, the dry eye disorder is non-Sjogren syndrome dry eye (NSSDE).

Further JAK-associated diseases include conjunctivitis, uveitis (including chronic uveitis), chorioditis, retinitis, cyclitis, sclieritis, episcleritis, or iritis. Other JAK-associated diseases include respiratory dysfunction or failure associated with viral infection, such as influenza and SARS.

EXAMPLES

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1

Synthesis of 2-(3-(4-(7H-Pyrrolo[2,3-d]pyrimidin-4-yl)-1H-pyrazol-1-yl)-1-(1-(3-fluoro-2-(trifluoromethyl)isonicotinoyl)piperidin-4-yl)azetidin-3-yl)acetonitrile Adipate (9)

Scheme I

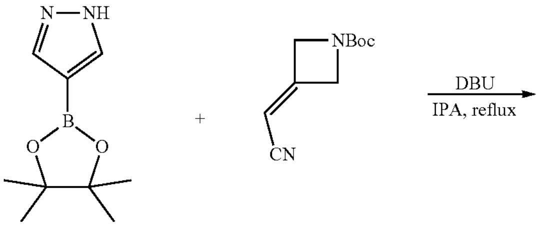

1 2

$C_9H_{15}BN_2O_2$
Mol. Wt: 194.04

$C_{10}H_{14}N_2O_2$
Mol. Wt: 194.23

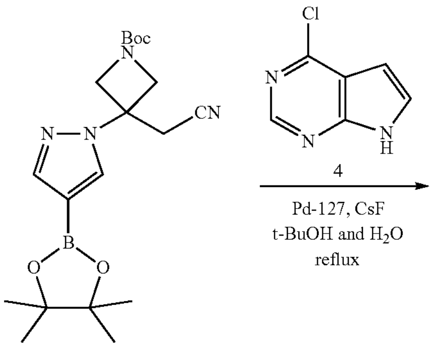

3

$C_{19}H_{29}BN_4O_4$
Mol. Wt: 388.27

-continued

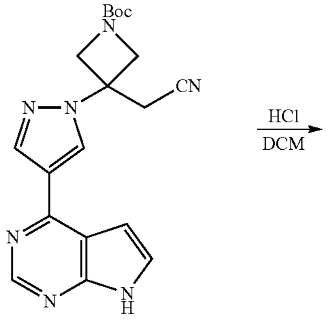

5

$C_{19}H_{21}N_7O_2$
Mol. Wt: 379.42

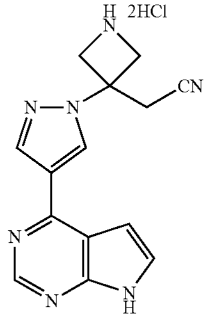

6

$C_{14}H_{15}Cl_2N_7$
Mol. Wt: 352.22

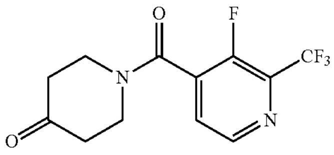

7

NaBH(OAc)3, Et3N
DCM

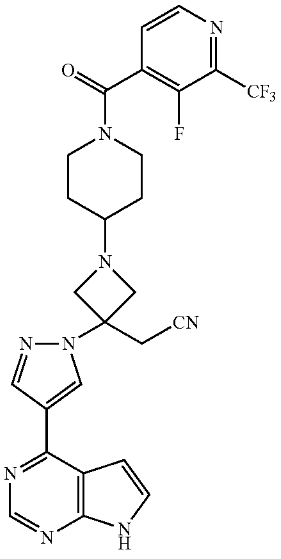

8

$C_{26}H_{23}F_4N_8O$
Mol. Wt: 553.51

Adipic acid
acetone and n-heptane

-continued

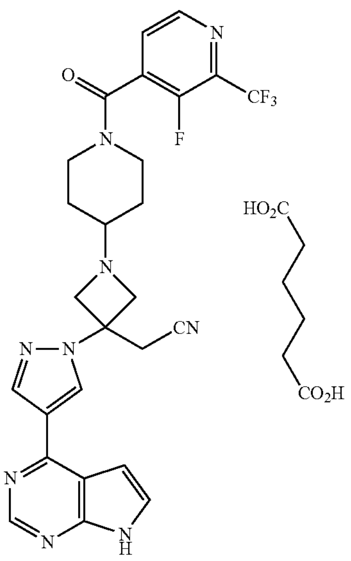

9

$C_{32}H_{33}F_4N_9O_5$
Mol. Wt: 699.66 tert-Butyl 3-(cyanomethyl)-3-(4-(4,4,5,5-tetramethyl-1,3,2-dioxaborolan-2-yl)-1H-pyrazol-1-yl) azetidine-1-carboxylate (3)

To a 1-L flask equipped with a nitrogen inlet, a thermocouple, and a mechanical stirrer were sequentially added isopropanol (IPA, 200 mL), 1,8-diazabicyclo[5,4,0]undecene (DBU, 9.8 g, 64.4 mmol, 0.125 equiv), 4-(4,4,5,5-tetramethyl-1,3,2-dioxaborolan-2-yl)-1H-pyrazole (1, 101 g, 520.51 mmol, 1.01 equiv) and tert-butyl 3-(cyanomethylene) azetidine-1-carboxylate (2, 100 g, 514.85 mmol) at ambient temperature to generate a reaction mixture as a suspension. The resulting reaction mixture was heated to reflux in 30 minutes to provide a homogenous solution and the mixture was maintained at reflux for an additional 2-3 hours. After the reaction was complete as monitored by HPLC, n-heptane (400 mL) was gradually added to the reaction mixture in 45 minutes while maintaining the mixture at reflux. Solids were precipitated out during the n-heptane addition. Once n-heptane addition was complete, the mixture was gradually cooled to ambient temperature and stirred at ambient temperature for an additional 1 hour. The solids were collected by filtration, washed with n-heptane (200 mL), and dried under vacuum at 50° C. with nitrogen sweeping to constant weight to afford tert-butyl 3-(cyanomethyl)-3-(4-(4,4,5,5-tetramethyl-1,3,2-dioxaborolan-2-yl)-1H-pyrazol-1-yl)azetidine-1-carboxylate (3, 181 g, 199.9 g theoretical, 90.5%) as a white to pale yellow solid. For 3: $^1$H NMR (400 MHz, DMSO-$d_6$) δ 8.31 (s, 1H), 7.74 (s, 1H), 4.45-4.23 (m, 2H), 4.23-4.03 (m, 2H), 3.56 (s, 2H), 1.38 (s, 9H), 1.25 (s, 12H) ppm; $^{13}$C NMR (101 MHz, DMSO-$d_6$) δ 155.34, 145.50, 135.88, 116.88, 107.08 (br), 83.15, 79.36, 158.74 (br), 56.28, 27.96, 26.59, 24.63 ppm; $C_{19}H_{29}BN_4O_4$ (MW 388.27), LCMS (EI) m/e 389 ($M^+$+H).

tert-Butyl 3-(4-(7H-pyrrolo[2,3-d]pyrimidin-4-yl)-1H-pyrazol-1-yl)-3-(cyanomethyl)-azetidine-1-carboxylate (5)

To a 1-L flask equipped with a nitrogen inlet, a thermocouple, and a mechanical stirrer were added 4-chloro-7H-pyrrolo[2,3-d]pyrimidine (4, 39.6 g, 257.6 mmol), tert-butyl 3-(cyanomethyl)-3-(4-(4,4,5,5-tetramethyl-1,3,2-dioxaborolan-2-yl)-1H-pyrazol-1-yl)azetidine-1-carboxylate (3, 100 g, 257.6 mmol, 1.0 equiv), cesium fluoride (136.9 g, 901.4 mmol, 3.5 equiv), tert-butanol (250 mL), water (250 mL), and [1,1'-bis(di-cyclohexylphosphino)ferrocene]dichloropalladium(II) (Pd-127, 351.4 mg, 0.46 mmol, 0.0018 equiv) at ambient temperature. The resulting reaction mixture was degassed and refilled with nitrogen for 3 times before being heated to reflux and maintained at reflux under nitrogen for 20-24 hours. When HPLC showed the reaction was complete, the reaction mixture was cooled to 45-55° C. in 30 minutes, the two phases were separated, and the aqueous phase was discarded. To the organic phase was added n-heptane (125 mL) in 30 minutes at 45-55° C. The resulting mixture was slowly cooled to ambient temperature in one hour and stirred at ambient temperature for an additional 2 hours. The solids were collected by filtration, washed with n-heptane (100 mL), and dried under vacuum at 50° C. with nitrogen sweeping to constant weight to afford tert-butyl 3-(4-(7H-pyrrolo[2,3-d]pyrimidin-4-yl)-1H-pyrazol-1-yl)-3-(cyanomethyl)-azetidine-1-carboxylate (5, 96.8 g, 97.7 g theoretical, 99%) as a pale yellow solid. For 5: $^{1}$H NMR (400 MHz, DMSO-$d_6$) δ 8.89 (s, 1H), 8.68 (s, 1H), 8.44 (s, 1H), 7.60 (d, J=3.5 Hz, 1H), 7.06 (d, J=3.6 Hz, 1H), 4.62-4.41 (m, 2H), 4.31-4.12 (m, 2H), 3.67 (s, 2H), 1.39 (s, 9H) ppm; $^{13}$C NMR (101 MHz, DMSO-$d_6$) δ 155.40, 152.60, 150.63, 149.15, 139.76, 129.53, 127.65, 122.25, 116.92, 113.21, 99.71, 79.45, 58.34 (br), 56.80, 27.99, 26.83 ppm; $C_{19}H_{21}N_7O_2$ (MW 379.4), LCMS (EI) m/e 380 ($M^+$+H).

2-(3-(4-(7H-Pyrrolo[2,3-d]pyrimidin-4-yl)-1H-pyrazol-1-yl)azetidin-3-yl)acetonitrile dihydrochloride salt (6)

To a 0.5-L flask equipped with a nitrogen inlet, a thermocouple, an additional funnel, and a mechanical stirrer were added tert-butyl 3-(4-(7H-pyrrolo[2,3-d]pyrimidin-4-yl)-1H-pyrazol-1-yl)-3-(cyanomethyl)azetidine-1-carboxylate (5, 15 g, 39.5 mmol), water (7.5 mL, 416 mmol) and dichloromethane (75 mL) at room temperature. The mixture was stirred at room temperature to generate a suspension. To the suspension was added a solution of 5 M hydrogen chloride (HCl) in isopropanol (55 mL, 275 mmol, 7.0 equiv) in 5 minutes. The resulting reaction mixture was then heated to gentle reflux and maintained at reflux for 3-4 hours. After the reaction was completed as monitored by HPLC, tert-butyl methyl ether (TBME, 45 mL) was added to the reaction suspension. The mixture was gradually cooled to room temperature, and stirred for an additional one hour. The solids were collected by filtration, washed with tert-butyl methyl ether (TBME, 45 mL) and dried under vacuum at 50° C. with nitrogen sweeping to constant weight to afford 2-(3-(4-(7H-pyrrolo[2,3-d]pyrimidin-4-yl)-1H-pyrazol-1-yl)azetidin-3-yl)acetonitrile dihydrochloride salt (6, 13.6 g, 13.9 g theoretical, 98%) as an off-white to light yellow solid. For 6: $^{1}$H NMR (400 MHz, $D_2O$) δ 8.96 (s, 1H), 8.81 (s, 1H), 8.49 (s, 1H), 7.78 (d, J=3.8 Hz, 1H), 7.09 (d, J=3.7 Hz, 1H), 4.93 (d, J=12.8 Hz, 2H), 4.74 (d, J=12.5 Hz, 2H), 3.74 (s, 2H) ppm; $^{13}$C NMR (101 MHz, $D_2O$) δ 151.35, 143.75, 143.33, 141.33, 132.03, 131.97, 115.90, 114.54, 113.85, 103.18, 59.72, 54.45 (2C), 27.02 ppm; $C_{14}H_{15}Cl_2N_7$ ($C_{14}H_{13}N_7$ for free base, MW 279.30), LCMS (EI) m/e 280 ($M^+$+H).

2-(3-(4-(7H-Pyrrolo[2,3-d]pyrimidin-4-yl)-1H-pyrazol-1-yl)-1-(1-(3-fluoro-2-(trifluoromethyl)isonicotinoyl)piperidin-4-yl)azetidin-3-yl)acetonitrile (8, Free Base)

To a 0.5-L flask equipped with a nitrogen inlet, a thermocouple, an additional funnel, and a mechanical stirrer were added 2-(3-(4-(7H-pyrrolo[2,3-d]pyrimidin-4-yl)-1H-pyrazol-1-yl)azetidin-3-yl)acetonitrile dihydrochloride salt (6, 20 g, 56.78 mmol), dichloromethane (200 mL) and triethylamine (TEA, 16.62 mL, 119.2 mmol, 2.1 equiv) at ambient temperature. The mixture was stirred at ambient temperature for 30 minutes before 1-(3-fluoro-2-(trifluoromethyl)-isonicotinoyl)piperidin-4-one (7, 17.15 g, 57.91 mmol, 1.02 equiv) was added to the mixture. The mixture was then treated with sodium triacetoxyborohydride (25.34 g, 113.6 mmol, 2.0 equiv) in 5 minutes at ambient temperature (below 26° C.). The resulting reaction mixture was stirred at ambient temperature for 2 hours. After the reaction was complete as monitored by HPLC, the reaction mixture was quenched with saturated $NaHCO_3$ aqueous solution (200 mL). The two phases were separated and the aqueous phase was extracted with methylene chloride (200 mL). The combined organic phase was washed with 4% brine (100 mL) followed by solvent switch of methylene chloride to acetone by distillation. The resulting solution of the desired crude product (8) in acetone was directly used for the subsequent adipate salt formation. A small portion of solution was purified by column chromatography ($SiO_2$, 0-10% of MeOH in EtOAc gradient elution) to afford the analytically pure 2-(3-(4-(7H-pyrrolo[2,3-d]pyrimidin-4-yl)-1H-pyrazol-1-yl)-1-(1-(3-fluoro-2-(trifluoromethyl)isonicotinoyl)piperidin-4-yl)azetidin-3-yl)acetonitrile (8 free base) as an off-white solid. For 8: $^{1}$H NMR (400 MHz, DMSO-$d_6$) δ 12.17 (d, J=2.8 Hz, 1H), 8.85 (s, 1H), 8.70 (m, 2H), 8.45 (s, 1H), 7.93 (t, J=4.7 Hz, 1H), 7.63 (dd, J=3.6, 2.3 Hz, 1H), 7.09 (dd, J=3.6, 1.7 Hz, 1H), 4.10 (m, 1H), 3.78 (d, J=7.9 Hz, 2H), 3.61 (t, J=7.9 Hz, 1H), 3.58 (s, 2H), 3.46 (m, 1H), 3.28 (t, J=10.5 Hz, 1H), 3.09 (ddd, J=13.2, 9.5, 3.1 Hz, 1H), 2.58 (m, 1H), 1.83-1.75 (m, 1H), 1.70-1.63 (m, 1H), 1.35-1.21 (m, 2H) ppm; $^{13}$C NMR (101 MHz, DMSO-$d_6$) δ 160.28, (153.51, 150.86), 152.20, 150.94, 149.62, (146.30, 146.25), 139.48, (134.78, 134.61), (135.04, 134.92, 134.72, 134.60, 134.38, 134.26, 134.03, 133.92), 129.22, 127.62, 126.84, 121.99, 122.04, (124.77, 122.02, 119.19, 116.52), 117.39, 113.00, 99.99, 61.47, 60.49, 57.05, 44.23, 28.62, 27.88, 27.19 ppm; $C_{26}H_{23}F_4N_9O$ (MW, 553.51), LCMS (EI) m/e 554.1 ($M^+$+H).

2-(3-(4-(7H-Pyrrolo[2,3-d]pyrimidin-4-yl)-1H-pyrazol-1-yl)-1-(1-(3-fluoro-2-(trifluoromethyl)isonicotinoyl)piperidin-4-yl)azetidin-3-yl)acetonitrile Adipate (9)

To a 0.5-L flask equipped with a mechanical stirrer, a thermocouple, an addition funnel, and a nitrogen inlet was added a solution of crude 2-(3-(4-(7H-pyrrolo[2,3-d]pyrimidin-4-yl)-1H-pyrazol-1-yl)-1-(1-(3-fluoro-2-(trifluoromethyl)isonicotinoyl)piperidin-4-yl)azetidin-3-yl)acetonitrile (8 free base, 31.38 g, 56.7 mmol) in acetone (220 mL) and adipic acid (8.7 g, 59.53 mmol, 1.05 equiv) at ambient temperature. The reaction mixture was then heated to reflux to give a solution. n-Heptane (220 mL) was gradually added to the reaction mixture at 40-50° C. in one hour. The resulting mixture was gradually cooled to ambient temperature in one hour and stirred at ambient temperature for an additional 16 hours. The solids were collected by filtration, washed with n-heptane (2×60 mL), and dried under vacuum at 50° C. with nitrogen sweeping to constant weight to afford 2-(3-(4-(7H-Pyrrolo[2,3-d]pyrimidin-4-yl)-1H-pyrazol-1-yl)-1-(1-(3-fluoro-2-(trifluoromethyl)isonicotinoyl)piperidin-4-yl)azetidin-3-yl)acetonitrile adipate (9, 34.0 g, 39.7 g theoretical, 85.6% for two steps) as a white to off-white solid. 9: $^1$H NMR (400 MHz, DMSO-$d_6$) δ 12.16 (s, 1H), 12.05 (brs, 2H), 8.85 (s, 1H), 8.72 (s, 1H), 8.69 (d, J=4.7 Hz, 1H), 8.45 (s, 1H), 7.93 (t, J=4.7 Hz, 1H), 7.63 (dd, J=3.6, 2.3 Hz, 1H), 7.09 (dd, J=3.6, 1.7 Hz, 1H), δ 4.11 (dt, J=11.0, 4.4 Hz, 1H), 3.77 (d, J=7.8 Hz, 2H), 3.60 (t, J=7.8 Hz, 2H), 3.58 (s, 2H), 3.44 (dt, J=14.4, 4.6 Hz, 1H), 3.28 (t, J=10.4 Hz, 1H), 3.09 (ddd, J=13.2, 9.6, 3.2 Hz, 1H), 2.58 (tt, J=8.6, 3.5 Hz, 1H), 2.28-2.17 (m, 4H), 1.83-1.74 (m, 1H), 1.67 (d, J=11.0 Hz, 1H), 1.59-1.46 (m, 4H), 1.37-1.21 (m, 2H) ppm; $^{13}$C NMR (101 MHz, DMSO-$d_6$) δ 174.38, 160.29, (153.52, 150.87), 152.20, 150.94, 149.63, (146.30, 146.25), 139.48, (134.79, 134.62), (135.08, 134.97, 134.74, 134.62, 134.38, 134.28, 134.04, 133.93), 129.21, 127.62, 126.84, 122.05, (124.75, 122.02, 119.29, 116.54), 117.39, 113.01, 99.99, 61.47, 60.50, 57.06, 44.24, 33.42, 30.70, 28.63, 27.89, 27.20, 24.07 ppm; $C_{32}H_{33}F_4N_9O_5$ (MW 699.66; $C_{26}H_{23}F_4N_9O$ for free base, MW, 553.51), LCMS (EI) m/e 554.0 ($M^+$+H).

Example 2

Alternative Synthesis of 2-(3-(4-(7H-Pyrrolo[2,3-d]pyrimidin-4-yl)-1H-pyrazol-1-yl)-1-(1-(3-fluoro-2-(trifluoromethyl)isonicotinoyl)piperidin-4-yl)azetidin-3-yl)acetonitrile Scheme II

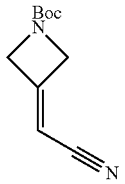

2

$C_{10}H_{14}N_2O_2$
Mol. Wt: 194.23

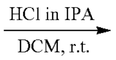

-continued

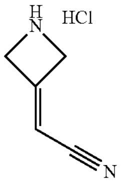

2a $C_5H_7ClN_2$
Mol. Wt: 130.58

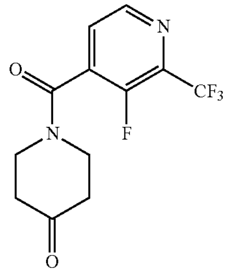

7

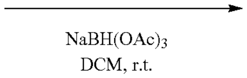

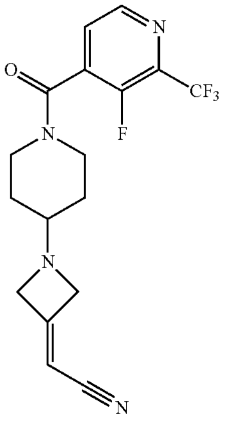

10

$C_{17}H_{16}F_4N_4O$
Mol. Wt: 368.33

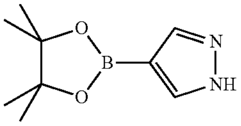

1

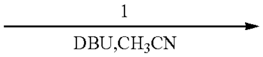

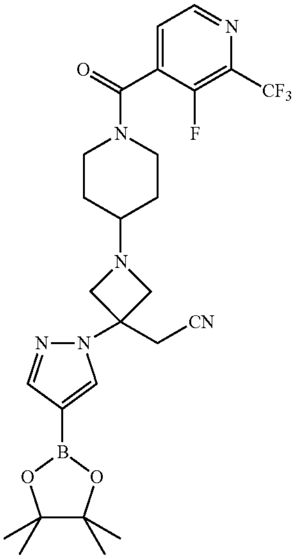

11

$C_{26}H_{31}BF_4N_6O_3$
Mol. Wt: 562.37

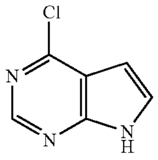

4

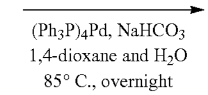

-continued

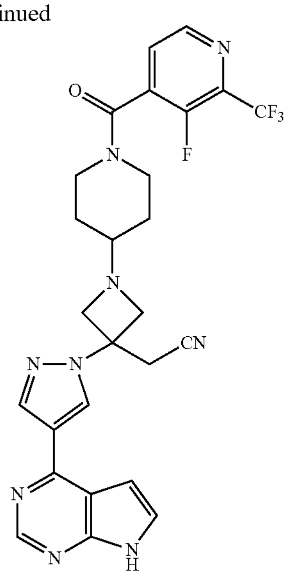

$C_{26}H_{23}F_4N_9O$
Mol. Wt: 553.51

2-(Azetidin-3-ylidene)acetonitrile hydrochloride (2a)

To a 0.5-L flask equipped with a nitrogen inlet, a thermocouple, and a mechanical stirrer were added tert-butyl 3-(cyanomethylene)azetidine-1-carboxylate (2, 30 g, 154.46 mmol) and methylenechloride (300 mL) at ambient temperature. The solution was then treated with a solution of 5 M hydrogen chloride (HCl) in isopropanol solution (294.2 mL, 1.54 mol, 10 equiv) at ambient temperature and the resulting reaction mixture was stirred at ambient temperature for 18 hours. After the reaction was complete as monitored by HPLC, the suspension was added tert-butyl methyl ether (TBME, 150 mL), and the mixture was stirred at ambient temperature for 2 hours. The solids was collected by filtration, washed with n-heptane (2×100 mL), and dried on the filtration funnel at ambient temperature for 3 hours to afford 2-(azetidin-3-ylidene)acetonitrile hydrochloride (2a, 13.7 g, 20.2 g theoretical, 67.8%) as a white solid. For 2a: $^1$H NMR (500 MHz, DMSO-$d_6$) δ 9.99 (s, 2H), 5.94 (p, J=2.5 Hz, 1H), 4.85-4.80 (m, 2H), 4.77-4.71 (m, 2H) ppm; $^{13}$C NMR (126 MHz, DMSO-$d_6$) δ 155.65, 114.54, 94.78, 55.26, 54.63 ppm; $C_5H_7ClN_2$ (MW 130.58; $C_5H_6N_2$ for free base, MW 94.11), LCMS (EI) m/e 95 ($M^+$+H).

2-(1-(1-(3-Fluoro-2-(trifluoromethyl)isonicotinoyl)piperidin-4-yl)azetidin-3-ylidene)acetonitrile (10)

To a 0.25-L flask equipped with a nitrogen inlet, a thermocouple, and a magnetic stirrer were added 2-(azetidin-3-ylidene)acetonitrile hydrochloride (2a, 4.5 g, 34.46 mmol), 1-(3-fluoro-2-(trifluoromethyl)isonicotinoyl)piperidin-4-one (7, 10 g, 34.46 mmol, 1.0 equiv), and methylenechloride (100 mL) at ambient temperature and the resulting mixture was then treated with sodium triacetoxyborohydride (14.6 g, 68.93 mmol, 2.0 equiv) at ambient temperature. The reaction mixture was stirred at ambient temperature for 2 hours before being quenched with saturated sodium bicarbonate ($NaHCO_3$) aqueous solution (50 mL). The two phases were separated and the aqueous phase was extracted with dichloromethane (200 mL). The combined organic phase was washed with water (50 mL) and brine (50 mL) and concentrated under reduced pressure to afford the crude desired product (10), which was purified by column chromatography ($SiO_2$, 0-10% of ethyl acetate in hexane gradient elution) to afford 2-(1-(1-(3-fluoro-2-(trifluoromethyl)isonicotinoyl)piperidin-4-yl)azetidin-3-ylidene)acetonitrile (10, 9.5 g, 12.7 g theoretical, 74.8%) as a white solid. For 10: $^1$H NMR (400 MHz, $CDCl_3$) δ 8.57 (d, J=4.7 Hz, 1H), 7.54 (t, J=4.6 Hz, 1H), 5.29 (p, J=2.4 Hz, 1H), 4.18-4.08 (m, 1H), 4.08-4.03 (m, 2H), 3.98-3.94 (m, 2H), 3.57-3.39 (m, 2H), 3.17-3.04 (m, 1H), 2.56 (tt, J=7.4, 3.5 Hz, 1H), 1.86-1.77 (m, 1H), 1.75-1.64 (m, 1H), 1.54-1.43 (m, 1H), 1.43-1.31 (m, 1H) ppm; $^{13}$C NMR (101 MHz, $CDCl_3$) δ 161.34, 160.73, 152.62 (d, J=269.1 Hz), 145.75 (d, J=6.1 Hz), 136.73 (qd, J=36.1, 12.0 Hz), 134.56 (d, J=16.9 Hz), 126.89, 120.58 (qd, J=275.0, 4.9 Hz), 115.11, 92.04, 62.05, 60.57 (2C), 44.47, 39.42, 29.38, 28.47 ppm; $C_{17}H_{16}F_4N_{40}$ (MW 368.33), LCMS (EI) m/e 369 ($M^+$+H).

2-(1-(1-(3-Fluoro-2-(trifluoromethyl)isonicotinoyl)piperidin-4-yl)-3-(4-(4,4,5,5-tetramethyl-1,3,2-dioxaborolan-2-yl)-1H-pyrazol-1-yl)azetidin-3-yl)acetonitrile (11)

To a 25 mL flask equipped with a nitrogen inlet, a thermocouple, and a magnetic stirrer were added 4-(4,4,5,5-tetramethyl-1,3,2-dioxaborolan-2-yl)-1H-pyrazole (1, 210 mg, 1.08 mmol, 1.08 equiv), 2-(1-(1-(3-fluoro-2-(trifluoromethyl)isonicotinoyl)piperidin-4-yl)azetidin-3-ylidene)acetonitrile (10, 370 mg, 1.0 mmol) and acetonitrile (3 mL) at ambient temperature. The solution was then treated with 1,8-diazabicyclo[5,4,0]undec-ene (DBU, 173 mg, 0.17 mL, 1.12 mmol, 1.12 equiv) at ambient temperature and the resulting reaction mixture was warmed to 50° C. and stirred at 50° C. for overnight. When the reaction was complete as monitored by HPLC, the reaction mixture was directly load on a solica gel ($SiO_2$) column for chromatographic purification (0-2.5% MeOH in ethyl acetate gradient elution) to afford 2-(1-(1-(3-fluoro-2-(trifluoromethyl)isonicotinoyl)piperidin-4-yl)-3-(4-(4,4,5,5-tetramethyl-1,3,2-dioxaborolan-2-yl)-1H-pyrazol-1-yl)azetidin-3-yl)acetonitrile (11, 263 mg, 562.4 mg theoretical, 46.7%) as a white solid. For 11: $^1$H NMR (400 MHz, DMSO-$d_6$) δ 8.64 (d, J=4.7 Hz, 1H), 8.22 (d, J=0.6 Hz, 1H), 7.88 (dd, J=4.7 Hz, 1H), 7.69 (s, 1H), 4.10-3.99 (m, 1H), 3.58 (d, J=7.8 Hz, 2H), 3.52-3.42 (m, 2H), 3.44 (s, 2H), 3.41-3.33 (m, 1H), 3.28-3.15 (m, 1H), 3.03 (ddd, J=12.9, 9.2, 3.2 Hz, 1H), 2.51-2.44 (m, 1H), 1.77-1.66 (m, 1H), 1.64-1.54 (m, 1H), 1.28-1.17 (m, 2H), 1.24 (s, 12H) ppm; $^{13}$C NMR (101 MHz, DMSO-$d_6$) δ 160.22, 152.13 (d, J=265.8 Hz), 146.23 (d, J=5.7 Hz), 145.12, 135.41, 134.66 (d, J=16.9 Hz), 134.43 (qd, J=35.0, 11.7 Hz), 127.58, 120.61 (qd, J=274.4, 4.6 Hz), 117.35, 106.59 (br), 83.10, 61.40, 60.53 (2C), 56.49, 44.17, 38.99, 28.55, 27.82, 27.02, 24.63 ppm; $C_{26}H_{31}BF_4N_6O_3$ (MW 562.37), LCMS (EI) m/e 563 ($M^+$+H).

2-(3-(4-(7H-Pyrrolo[2,3-d]pyrimidin-4-yl)-1H-pyrazol-1-yl)-1-(1-(3-fluoro-2-(trifluoromethyl)isonicotinoyl)piperidin-4-yl)azetidin-3-yl)acetonitrile (8)

To a 25-mL flask equipped with a nitrogen inlet, a thermocouple, an additional funnel, and a magnetic stirrer were added 2-(1-(1-(3-fluoro-2-(trifluoromethyl)-isonicotinoyl)piperidin-4-yl)-3-(4-(4,4,5,5-tetramethyl-1,3,2-dioxaborolan-2-yl)-1H-pyrazol-1-yl)azetidin-3-yl)acetonitrile (11, 307 mg, 0.546 mmol), 4-chloro-7H-pyrrolo[2,3-d]pyrimidine (4, 84.8 mg, 0.548 mmol, 1.0 equiv), sodium bicarbonate ($NaHCO_3$, 229 mg, 2.72 mmol, 5.0 equiv), water (1.6 mL), and 1,4-dioxane (1.6 mL) at ambient temperature. The mixture was then treated with tetrakis(triphenylphosphine)palladium(0) (12.8 mg, 0.011 mmol, 0.02 equiv) at ambient temperature and the resulting reaction mixture was de-gassed and refilled with nitrogen for 3 times before being heated to 85° C. The reaction mixture was stirred at 85° C. under nitrogen for overnight. When the reaction was complete as monitored by HPLC, the reaction mixture was concentrated to dryness under reduced pressure and the desired product, 2-(3-(4-(7H-pyrrolo[2,3-d]pyrimidin-4-yl)-1H-pyrazol-1-yl)-1-(1-(3-fluoro-2-(trifluoromethyl)isonicotinoyl)piperidin-4-yl)azetidin-3-yl)acetonitrile (8 free base, 135 mg, 302.2 mg theoretical, 44.6%), was obtained as off-white solids by direct silica gel ($SiO_2$) column chromatography (0-10% of ethyl acetate in hexane gradient elution) purification of the dried reaction mixture. The compound obtained by this synthetic approach is identical in every comparable aspect to the compound 8 manufactured by the synthetic method as described above in Example 1.

Example 3

Synthesis of (3-Fluoro-2-(trifluoromethyl)pyridin-4-yl)(1,4-dioxa-8-azaspiro[4,5]decan-8-yl)methanone Scheme III

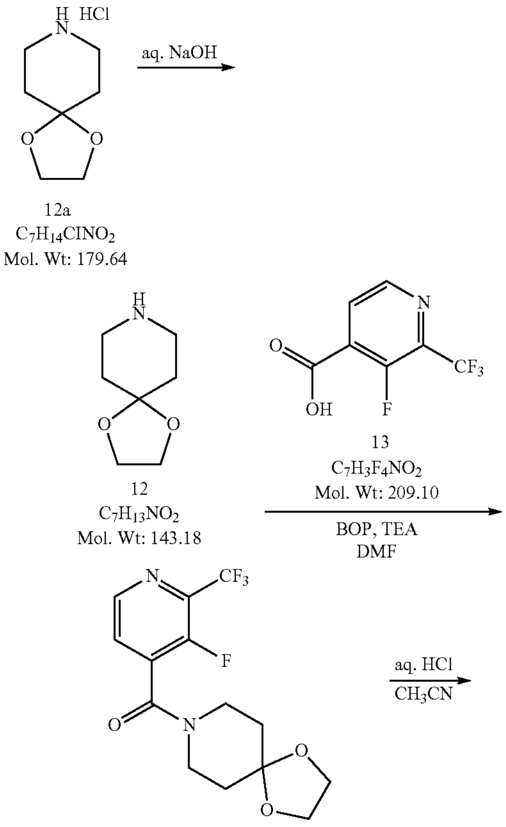

12a
$C_7H_{14}ClNO_2$
Mol. Wt: 179.64

12
$C_7H_{13}NO_2$
Mol. Wt: 143.18

13
$C_7H_3F_4NO_2$
Mol. Wt: 209.10

14
$C_{14}H_{14}F_4N_2O_3$
Mol. Wt: 334.27

-continued

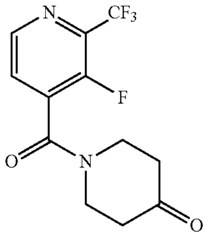

7
$C_{12}H_{10}F_4N_2O_2$
Mol. Wt: 290.21

(3-Fluoro-2-(trifluoromethyl)pyridin-4-yl)(1,4-dioxa-8-azaspiro[4,5]decan-8-yl)methanone (14)

To a 30 L reactor equipped with a mechanic stirrer, an addition funnel and a septum was charged sodium hydroxide (NaOH, 1.4 kg, 35 mol, 2.0 equiv) and water (7 L) and the resulting solution was treated with 1,4-dioxa-8-azaspiro[4.5]decane hydrochloride (3.13 kg, 17.43 mol) at ambient temperature. The resulting mixture was then stirred at ambient temperature for 30 minutes before being saturated with solid sodium chloride (1.3 kg) and extracted with 2-methyl-tetrahydrofuran (3×7 L). The combined organic phase was dried with anhydrous sodium sulfate ($Na_2SO_4$, 1.3 kg) and concentrated under reduced pressure (70 mmHg) at 50° C. after removal of the drying reagent, sodium sulfate ($Na_2SO_4$), by filtration. The yellow oil thus obtained was distilled under reduced pressure (80 mmHg, by 115 to 120° C.) to afford 1,4-dioxa-8-azaspiro[4.5]decane (2.34 kg, 2.496 kg theoretical, 93.8%) as a clear oil, which was used directly in the subsequent coupling reaction.

To a dried 100 L reactor equipped with a mechanic stirrer, an addition funnel, a thermometer and a vacuum outlet was charged 3-fluoro-2-(trifluoromethyl)isonicotinic acid (13, 3.0 kg, 14.35 mol), benzotriazol-1-yloxytris(dimethylamino)phosphonium hexafluorophosphate (BOP reagent, 7.6 kg, 17.2 mol, 1.2 equiv), 1,4-dioxa-8-azaspiro[4.5]decane (2.34 kg, 16.36 mol, 1.14 equiv) and N,N-dimethylformamide (DMF, 18 L) at ambient temperature. The resulting solution was then stirred at ambient temperature for 20 minutes before being cooled to 5 to 10° C. Triethylamine ($Et_3N$, 4 L, 28.67 mol, 2.0 equiv) was then added to the reaction mixture over 1 hour and the internal temperature was kept between 5° C. and 10° C. during the addition of triethylamine. The dark brown solution thus obtained was stirred for 12 h at ambient temperature (approximately 20° C.) and then chilled to around 10° C. With vigorous stirring, 18 L of the saturated sodium bicarbonate ($NaHCO_3$) aqueous solution and 36 L of water were sequentially added to the chilled reaction mixture and the internal temperature was kept under 15° C. The precipitation (filter cake) thus obtained was collected by filtration. The aqueous phase was then saturated with 12 kg of solid sodium chloride (NaCl) and extracted with EtOAc (2×18 L). The combined organic layer was washed with saturated sodium bicarbonate ($NaHCO_3$) aqueous solution (18 L), and water (2×18 L) in sequence. The filter cake collected was then dissolved back in the organic phase and the resulting dark brown solution was washed with water (2×18 L) before being concentrated under reduced pressure (40-50° C., 30 mm Hg) to afford approximately 5.0 kg of the crude desired product (14) as a viscous brown oil. The crude product obtained above was then dissolved in EtOH (8.15 L) at 50° C. and the resulting solution was treated with water (16.3 L) over 30 minutes at around 50° C. The brown solution was seeded before being gradually cooled to ambient temperature (approximately 20° C.) over 3 hours with stirring and stirred at ambient temperature for 12 h. The solids were collected by filtration, washed with a mixture of EtOH and water (EtOH:$H_2O$=1:20, 2 L) and dried under reduced pressure (50 mmHg) at approximately 60° C. for 24 h to afford (3-fluoro-2-(trifluoromethyl)pyridin-4-yl)(1,4-dioxa-8-azaspiro[4,5]decan-8-yl)methanone (14, 3.98 kg, 4.797 kg theoretical, 83.0%) as a white solid. For 14: $^1$H NMR (300 MHz, DMSO-$d_6$) δ 8.64 (d, $^3J_{HH}$=4.68 Hz, 1H, NCH in pyridine), 7.92 (dd, $^3J_{HH}$=4.68 Hz, $^4J_{HF}$=4.68 Hz, 1H, NCCH in pyridine), 3.87-3.91 (m, 4H, $OCH_2CH_2O$), 3.70 (br s, 2H, one of $NCH_2$ in piperidine ring, one of another $NCH_2$ in piperidine ring, both in axial position), 3.26 (t, $^3J_{HH}$=5.86 Hz, 2H, one of $NCH_2$ in piperidine ring, one of another $NCH_2$ in piperidine ring, both in equatorial position), 1.67 (d, $^3J_{HH}$=5.86 Hz, 2H, one of $NCCH_2$ in piperidine ring, one of another $NCCH_2$ in piperidine ring, both in equatorial position), 1.58 (br s, 2H, one of $NCCH_2$ in piperidine ring, one of another $NCCH_2$ in piperidine ring, both in axial position) ppm; $^{13}$C NMR (75 MHz, DMSO-$d_6$) δ 161.03 (N—C═O), 151.16 (d, $^1J_{CF}$=266.03 Hz, C—F), 146.85 (d, $^4J_{CF}$=4.32 Hz, NCH in pyridine), 135.24 (d, $^2J_{CF}$=11.51 Hz, $\underline{C}$—C═O), 135.02 (quartet, $^2J_{CF}$=34.57 Hz, N$\underline{C}$$CF_3$), 128.24 (d, $^4J_{CF}$=7.48 Hz, NC$\underline{C}$H in pyridine), 119.43 (d×quartet, $^1J_{CF}$=274.38 Hz, $^3J_{CF}$=4.89 Hz, $CF_3$), 106.74 (O$\underline{C}$O), 64.60 (O$\underline{CC}$O), 45.34 (NC in piperidine ring), 39.62 (NC in piperidine ring), 34.79 (NC$\underline{C}$ in piperidine ring), 34.10 (NC$\underline{C}$ in piperidine ring) ppm; $^{19}$F NMR (282 MHz, DMSO-$d_6$) δ −64.69 (d, $^4J_{FF}$=15.85 Hz, $F_3C$), −129.26 (d×quartet, $^4J_{FF}$=15.85 Hz, $^4J_{FH}$=3.96 Hz, FC) ppm; $C_{14}H_{14}F_4N_2O_3$ (MW, 334.27), LCMS (EI) m/e 335.1 ($M^+$+H).

(3-Fluoro-2-(trifluoromethyl)pyridin-4-yl)(1,4-dioxa-8-azaspiro[4,5]decan-8-yl)methanone (7)

In a 5 L 4-necked round bottom flask equipped with a mechanical stirrer, a thermocouple, an addition funnel and a nitrogen inlet was charged (3-fluoro-2-(trifluoromethyl)pyridin-4-yl)(1,4-dioxa-8-azaspiro[4,5]decan-8-yl)methanone (14, 100 g, 0.299 mol) in acetonitrile (ACN, 400 mL) at ambient temperature. The resultant solution was cooled to below 10° C. before being treated with 6.0 N aqueous hydrochloric acid (HCl) solution (450 mL, 2.70 mol, 9.0 equiv) while the internal temperature was kept at below 10° C. The resulting reaction mixture was then gradually warmed to room temperature and an additional amount of 6.0 N aqueous hydrochloric acid (HCl) solution (1050 mL, 6.30 mol, 21.0 equiv) was slowly introduced to the reaction mixture at ambient temperature over 8 hours via the addition funnel. When the reaction was complete as monitored by HPLC, the reaction mixture was then cooled to 0° C. before being treated with 30% aqueous sodium hydroxide (NaOH, 860 mL, 8.57 mmol, 28.6 equiv) while the internal temperature was kept at below 10° C. The resulting reaction mixture was subsequently warmed to ambient temperature prior to addition of solid sodium bicarbonate ($NaHCO_3$, 85.0 g, 1.01 mol, 3.37 equiv) over 1 hour. The mixture was then extracted with EtOAc (2×1.2 L), and the combined organic phase was washed with 16% aqueous sodium chloride solution (2×800 mL) and concentrated to approximately 1.0 L by vacuum distillation. n-Heptane (2.1 L) was added to the residue, and the resulting mixture was concentrated to 1.0 L by vacuum distillation. To the concentrated mixture was added n-heptane (2.1 L). The resulting white slurry was then concentrated to 1.0 L by vacuum distillation. To the white slurry was then added methyl tert-butyl ether (MTBE, 1.94 L). The white turbid was heated to 40° C. to obtain a clear solution. The resulting solution was concentrated to about 1.0 L by vacuum distillation. The mixture was stirred at room temperature for 1 hour. The white precipitate was collected by filtration, washed with n-heptane (400 mL) and dried on the filter under nitrogen with pulling vacuum to afford (3-fluoro-2-(trifluoromethyl)pyridin-4-yl)(1,4-dioxa-8-azaspiro[4,5]decan-8-yl)methanone (7, 78.3 g, 86.8 g theoretical, 90.2%) as an off-white solid. For 7: $^1$H NMR (300 MHz, DMSO-$d_6$) δ 8.68 (d, $^3J_{HH}$=4.69 Hz, 1H, NCH in pyridine), 7.97 (dd, $^3J_{HH}$=4.69 Hz, $^4J_{HF}$=4.69 Hz, 1H, NCCH in pyridine), 3.92 (br s, 2H, one of $NCH_2$ in piperidine ring, one of another $NCH_2$ in piperidine ring, both in axial position), 3.54 (t, $^3J_{HH}$=6.15 Hz, 2H, one of $NCH_2$ in piperidine ring, one of another $NCH_2$ in piperidine ring, both in equatorial position), 2.48 (t, $^3J_{HH}$=6.44 Hz, 2H, $NCCH_2$), 2.34 (t, $^3J_{HH}$=6.15 Hz, 2H, $NCCH_2$) ppm; $^{13}$C NMR (75 MHz, DMSO-$d_6$) δ 207.17 (C═O), 161.66 (N—C═O), 151.26 (d, $^1J_{CF}$=266.89 Hz, C—F), 146.90 (d, $^4J_{CF}$=6.05 Hz, NCH in pyridine), 135.56 ($\underline{C}$—C═O), 134.78-135.56 (m, N$\underline{C}$$CF_3$), 128.27 (d, $^3J_{CF}$=7.19 Hz, NC$\underline{C}$H in pyridine), 119.52 (d×quartet, $^1J_{CF}$=274.38 Hz, $^3J_{CF}$=4.89 Hz, $CF_3$), 45.10 (NC in piperidine ring) ppm, one carbon (NC$\underline{C}$ in piperidine ring) missing due to overlap with $(CD_3)_2SO$; $^{19}$F NMR (282 MHz, DMSO-$d_6$) δ −64.58 (d, $^4J_{FF}$=15.85 Hz, $F_3C$), −128.90 (d×quartet, $^4J_{FF}$=15.85 Hz, $^4J_{FH}$=4.05 Hz, FC) ppm; $C_{12}H_{10}F_4N_2O_2$ (MW, 290.21), LCMS (EI) m/e 291.1 ($M^+$+H).

Example 4

Synthesis of tert-Butyl 3-(cyanomethylene)azetidine-1-carboxylate

Example IV

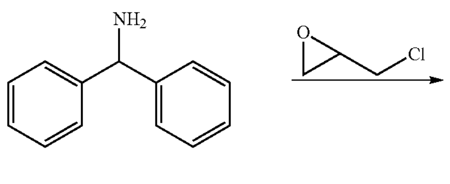

15

$C_{13}H_{13}N$
Mol. Wt: 183.25

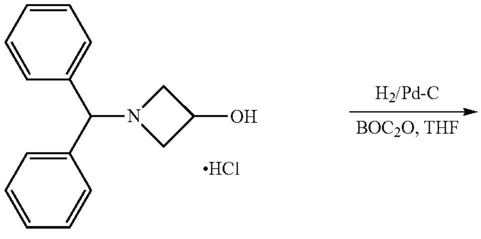

16

$C_{16}H_{18}ClNO$
Mol. Wt: 275.77

-continued

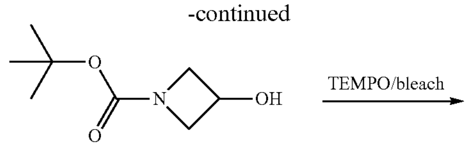

17

$C_8H_{15}NO_3$
Mol. Wt: 173.21

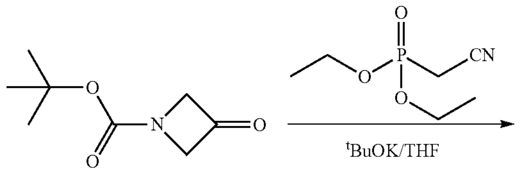

18

$C_8H_{13}NO_3$
Mol. Wt: 171.19

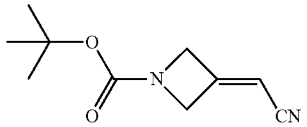

2

$C_{10}H_{14}N_2O_2$
Mol. Wt: 194.23

1-Benzhydrylazetidin-3-ol hydrochloride (16)

A solution of diphenylmethanamine (2737 g, 15.0 mol, 1.04 equiv) in methanol (MeOH, 6 L) was treated with 2-(chloromethyl)oxirane (1330 g, 14.5 mol) from an addition funnel at ambient temperature. During the initial addition a slight endotherm was noticed. The resulting reaction mixture was stirred at room temperature for 3 days before being warmed to reflux for an additional 3 days. When TLC showed that the reaction was deemed complete, the reaction mixture was first cooled down to room temperature and then to 0-5° C. in an ice bath. The solids were collected by filtration and washed with acetone (4 L) to give the first crop of the crude desired product (1516 g). The filtrate was concentrated under reduced pressure and the resulting semisolid was diluted with acetone (1 L). This solid was then collected by filtration to give the second crop of the crude desired product (221 g). The crude product, 1-benzhydrylazetidin-3-ol hydrochloride (1737 g, 3998.7 g theoretical, 43.4% yield), was found to be sufficiently pure to be used in the subsequent reaction without further purification. $^1$HNMR (300 MHz, DMSO-$d_6$) δ 12.28 (br. d, 1H), 7.7 (m, 5H), 7.49 (m, 5H), 6.38 (d, 1H), 4.72 (br. s, 1H), 4.46 (m, 1H), 4.12 (m, 2H), 3.85 (m, 2H) ppm; $C_{16}H_{18}ClNO$ (MW 275.77; $C_{16}H_{17}NO$ for free base, MW, 239.31), LCMS (EI) m/e 240 ($M^+$+H).

tert-Butyl 3-hydroxyazetidine-1-carboxylate (17)

A suspension of 1-benzhydrylazetidin-3-ol hydrochloride (625 g, 2.27 mol) in a 10% solution of aqueous sodium carbonate ($Na_2CO_3$, 5 L) and dichloromethane ($CH_2Cl_2$, 5 L) was stirred at room temperature until all solids were dissolved. The two layers were separated, and the aqueous layer was extracted with dichloromethane ($CH_2Cl_2$, 2 L). The combined organics extracts were dried over sodium sulfate ($Na_2SO_4$) and concentrated under reduced pressure. The resulting crude 1-benzhydrylazetidin-3-ol free base was then dissolved in THF (6 L) and the solution was placed into a large Parr bomb. Di-tert-butyl dicarbonate ($BOC_2O$, 545 g, 2.5 mol, 1.1 equiv) and 20% palladium (Pd) on carbon (125 g, 50% wet) were added to the Parr bomb. The vessel was charged to 30 psi with hydrogen gas ($H_2$) and stirred under steady hydrogen atmosphere (vessel was recharged three times to maintain the pressure at 30 psi) at room temperature for 18 h. When HPLC showed that the reaction was complete (no more hydrogen was taken up), the reaction mixture was filtered through a Celite pad and the Celite pad was washed with THF (4 L). The filtrates were concentrated under reduced pressure to remove the solvent and the residue was loaded onto a Biotage 150 column with a minimum amount of dichloromethane ($CH_2Cl_2$). The column was eluted with 20-50% ethyl acetate in n-heptane and the fractions containing the pure desired product, tert-butyl 3-hydroxyazetidine-1-carboxylate, were collected and combined. The solvents were removed under reduced pressure to afford tert-butyl 3-hydroxyazetidine-1-carboxylate (357 g, 393.2 g theoretical, 90.8% yield) as a colorless oil, which solidified upon standing at ambient temperature in vacuum. $^1$HNMR (300 MHz, $CDCl_3$), δ 4.56 (m 1H), 4.13 (m, 2H), 3.81 (m, 2H), 1.43 (s, 9H) ppm.

tert-Butyl 3-oxoazetidine-1-carboxylate (18)

A solution of tert-butyl 3-hydroxyazetidine-1-carboxylate (50 g, 289 mmol) in ethyl acetate (400 mL) was cooled to 0° C. The resulting solution was then treated with solid TEMPO (0.5 g, 3.2 mmol, 0.011 equiv) and a solution of potassium bromide (KBr, 3.9 g, 33.2 mmol, 0.115 equiv) in water (60 mL) at 0-5° C. While keeping the reaction temperature between 0-5° C., a solution of saturated aqueous sodium bicarbonate ($NaHCO_3$, 450 mL) and an aqueous sodium hypochlorite solution (NaClO, 10-13% available chlorine, 450 mL) were added. Once the solution of sodium hypochlorite was added, the color of the reaction mixture was changed immediately. When additional amount of sodium hypochlorite solution was added, the color of the reaction mixture was gradually faded. When TLC showed that all of the starting material was consumed, the color of the reaction mixture was no longer changed. The reaction mixture was then diluted with ethyl acetate (EtOAc, 500 mL) and two layers were separated. The organic layer was washed with water (500 mL) and the saturated aqueous sodium chloride solution (500 mL) and dried over sodium sulfate ($Na_2SO_4$). The solvent was then removed under reduced pressure to give the crude product, tert-butyl 3-oxoazetidine-1-carboxylate (48 g, 49.47 g theoretical, 97% yield), which was found to be sufficiently pure and was used directly in the subsequent reaction without further purification. $^1$HNMR ($CDCl_3$, 300 MHz) δ 4.65 (s, 4H), 1.42 (s, 9H) ppm.

tert-Butyl 3-(cyanomethylene)azetidine-1-carboxylate (2)

Diethyl cyanomethyl phosphate (745 g, 4.20 mol, 1.20 equiv) and anhydrous tetrahydrofuran (THF, 9 L) were added to a four-neck flask equipped with a thermowell, an addition funnel and the nitrogen protection tube at room temperature. The solution was cooled with an ice-methanol bath to −14° C. and a 1.0 M solution of potassium tert-butoxide (t-BuOK) in anhydrous tetrahydrofuran (THF, 3.85 L, 3.85 mol, 1.1 equiv) was added over 20 min keeping the reaction temperature below −5° C. The resulting reaction mixture was stirred for 3 h at −10° C. and a solution of 1-tert-butoxycarbonyl-3-azetidinone (600 g, 3.50 mol) in anhydrous tetrahydrofuran (THF, 2 L) was added over 2 h keeping the internal temperature below −5° C. The reaction mixture was stirred at −5 to −10° C. over 1 h and then slowly warmed up to room temperature and stirred at room temperature for overnight. The reaction mixture was then diluted with water (4.5 L) and saturated aqueous sodium chloride solution (NaCl, 4.5 L) and extracted with ethyl acetate (EtOAc, 2×9 L). The combined organic layers were washed with brine (6 L) and dried over anhydrous sodium sulfate ($Na_2SO_4$). The solvent was removed under reduced pressure and the residue was diluted with dichloromethane ($CH_2Cl_2$, 4 L) before being absorbed onto silica gel ($SiO_2$, 1.5 Kg). The crude product, which was absorbed on silica gel, was purified by flash column chromatography ($SiO_2$, 3.5 Kg, 0-25% EtOAc/hexanes gradient elution) to afford tert-butyl 3-(cyanomethylene)azetidine-1-carboxylate (2, 414.7 g, 679.8 g theoretical, 61% yield) as a white solid. For 2: $^1$H NMR (300 MHz, $CDCl_3$) δ 5.40 (m, 1H), 4.70 (m, 2H), 4.61 (m, 2H), 1.46 (s, 9H) ppm; $C_{10}H_{14}N_2O_2$ (MW, 194.23), LCMS (EI) m/e 217 ($M^+$+Na).

Example 5

Synthesis of 4-(4,4,5,5-Tetramethyl-1,3,2-dioxaborolan-2-yl)-1H-pyrazole

Example V

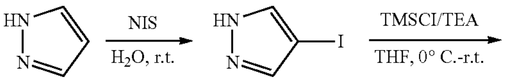

19 $C_3H_4N_2$ Mol. Wt: 68.08

20 $C_3H_3IN_2$ Mol. Wt: 193.97

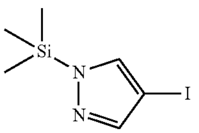

21 $C_6H_{11}IN_2Si$ Mol. Wt: 266.15

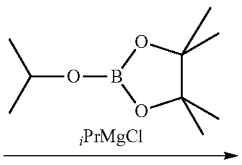

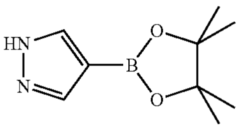

1 $C_9H_{15}BN_2O_2$ Mol. Wt.: 194.04

4-Iodopyrazole (20)

A flask equipped with a nitrogen inlet, an addition funnel, a thermowell, and a mechanical stirrer was charged with pyrazole (1, 450 g, 6.62 mol) and tetrahydrofuran (THF, 5 L) at ambient temperature. The mixture was then cooled to 10° C. and N-iodosuccinimide (NIS, 1490 g, 6.62 mol, 1.0 equiv) was added to the mixture in portions as a solid at approximately 10° C. The resulting reaction mixture was then stirred at ambient temperature for 1 hour (longer reaction times may be necessary depending on ambient temperature). The mixture was then filtered and the THF was removed under reduced pressure. The residue was suspended in ethyl acetate (6 L) and insoluble materials were filtered. The dark filtrate was sequentially washed with saturated aqueous sodium thiosulfate solution (2×3 L) (organic layer lightens to a pale yellow), water (2×3 L), and brine (2 L). The resulting organic layer was then dried over sodium sulfate, filtered, and concentrated under reduced pressure to afford 4-iodopyrazole (1138 g, 1284.1 g theoretical, 88.6%) as a white to pale yellow solid after being dried in a vacuum oven at approximately 30° C. overnight. $^1$H NMR (400 MHz, DMSO-$d_6$) δ 13.17 (bs, 1H), 7.93 (bs, 1H), 7.55 (bs, 1H) ppm; $C_3H_{31}N_2$ (MW, 193.97), LCMS (EI) m/e 195 ($M^+$+H).

1-Trimethylsilyl-4-iodopyrazole (21)

To a flask equipped with a reflux condenser, a nitrogen inlet, mechanical stirrer, and a thermowell was charged 4-iodopyrazole (200 g, 1.03 mol) and THF (2 L) at ambient temperature. To this solution was added triethylamine (TEA, 158 mL, 1.13 mol, 1.1 equiv) and the resulting solution was cooled to 0° C. in an ice-brine bath. To this solution was added chlorotrimethylsilane (TMS-Cl, 137 mL, 1.08 mol, 1.05 equiv) with vigorous stirring allowing the temperature to reach 18° C. (The reaction becomes very thick and difficult to stir, but becomes manageable after over time). When the exothermic process had subsided, the cold bath was removed and the reaction was warmed to room temperature. The reaction was followed by GC and was found to be deemed complete after about 1 hour (sampling of reaction must be done out of air and diluted with dry solvent to prevent TMS hydrolysis). The reaction mixture was then diluted with n-heptane (2 L) before being filtered under nitrogen. The solvent was removed from the filtrate under reduced pressure venting the rotovap with nitrogen. The residual oil was diluted with n-heptane (1 L) and re-concentrated. If the solids formed upon adding the n-heptane, a second filtration was necessary. The residue was then distilled under the reduced pressure (70-90° C. at about 0.5 Torr) using a Kugelohr to afford 1-trimethylsilyl-4-iodopyrazole (263 g, 274.1 g theoretical, 96%) as a colorless oil. This material must be kept under nitrogen at all times since the TMS group rapidly hydrolyzes. Subsequently, it was found that 1-trimethylsilyl-4-iodopyrazole can be prepared by heating the iodopyrazole with 2 equivalents of hexamethyldisilazane for 1 hr.

4-(4,4,5,5-Tetramethyl-1,3,2-dioxaborolan-2-yl)-1H-pyrazole (1)

A flask equipped with a mechanical stirrer, a nitrogen inlet, an addition funnel and a thermowell was charged with 1-trimethylsilyl-4-iodopyrazole (225.1 g, 0.85 mol) and THF (2200 mL) at ambient temperature. This mixture was cooled to approximately −6° C. in an ice/salt/brine bath before a solution of isopropyl magnesium chloride in THF (2 M solution in THF, 510 mL, 1.02 mol, 1.2 equiv) was added at a rate such that the internal temperature did not exceed 0° C. The extent of metal/halogen exchange was monitored by GC and was found complete after about 10 min. To the orange brown solution was then added 2-isopropoxy-4,4,5,5-tetramethyl-1,3,2-dioxaborolane (isopropylpinacolborate, 347 mL, 1.7 mol, 2.0 equiv) slowly at first keeping the temperature below 0° C. and then fairly rapidly after about half of the compound was added allowing the temperature to reach 5° C. (the reaction becomes quite thick and then thins out slowly). The reaction is then stirred at 0° C. for 10 min before being warmed to ambient temperature over 1 h and stirred at ambient temperature for an additional 1 h. The reaction mixture was cooled to approximately 6° C. and the saturated aqueous ammonium chloride solution ($NH_4Cl$, 2.2 L) was added with a temperature increase to 25° C. The mixture was stirred for 5 minutes before being diluted with toluene (10 L). The layers were separated (a large amount of solid is present in the aqueous layer) and the organic layer was sequentially washed with water (6×2.2 L) and brine (2×2.2 L) before being dried over sodium sulfate ($Na_2SO_4$). The drying reagent, sodium sulfate ($Na_2SO_4$), was removed by filtration and the solution was concentrated under reduced pressure. Residual toluene was co-evaporated with n-heptane to afford 4-(4,4,5,5-tetramethyl-1,3,2-dioxaborolan-2-yl)-1H-pyrazole (1, 90.3 g, 164.9 g theoretical, 54.8%) as a white solid. For 1: $^1H$ NMR (400 MHz, DMSO-$d_6$) δ 13.08 (bs, 1H), 7.94 (s, 1H), 7.62 (s, 1H), 1.23 (s, 12H) ppm; $C_9H_{15}BN_2O_2$ (MW, 194.04), LCMS (EI) m/e 195 ($M^+$+H).

Example 6

Alternative Synthesis of 4-(4,4,5,5-Tetramethyl-1,3,2-dioxaborolan-2-yl)-1H-pyrazole Scheme VI

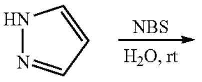

19

$C_3H_4N_2$
Mol. Wt: 68.08

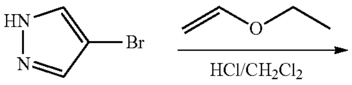

22

$C_3H_3BrN_2$
Mol. Wt: 146.97

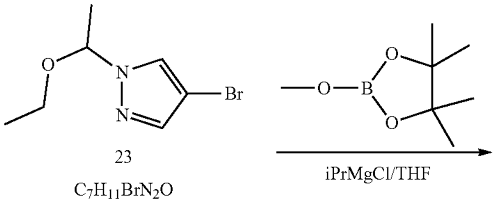

23

$C_7H_{11}BrN_2O$
Mol. Wt: 219.08

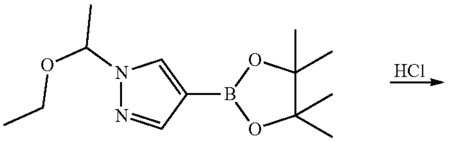

24

$C_{13}H_{23}BN_2O_3$
Mol. Wt: 266.14

-continued

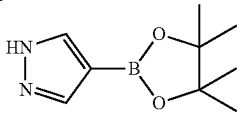

1

$C_9H_{15}BN_2O_2$
Mol. Wt: 194.04

4-Bromopyrazole (22)

Pyrazole (19, 34.0 g, 0.5 mol) and NBS (89.0 g, 0.5 mol, 1.0 equiv) were suspended in water (625 ml) at ambient temperature. The resulting suspension was stirred at ambient temperature for overnight. The reaction mixture was then extracted with EtOAc (2×100 mL). The combined EtOAc extracts were washed with aqueous $Na_2S_2O_3$ and brine, dried over $Na_2SO_4$, and concentrated under reduced pressure to afford crude 4-bromopyrazole (72.0 g, 73.5 g theoretical, 98% yield) as white solids (GC purity: >98%), which was directly used in the subsequent reaction without further purification.

4-Bromo-1-(ethoxyethyl)-1H-pyrazole (23)

To a solution of 4-bromopyrazole (70.0 g, 0.476 mol) in $CH_2Cl_2$ (600 mL) was added a solution of 3.1 M HCl in dioxane (4 mL) and ethyl vinyl ether (41 g, 0.569 mol, 1.2 equiv) at ambient temperature. The resulting reaction mixture was stirred at ambient temperature for 3 h. The reaction was quenched with aqueous $NaHCO_3$ and the two layers were separated. The organic layer was washed with water, dried over $Na_2SO_4$, and concentrated under reduced pressure to dryness to afford 4-bromo-1-(ethoxyethyl)-1H-pyrazole (113 g, 104.3 g theoretical, 97% yield) as an oil (GC purity: 89%), which was directly used in the subsequent reaction without further purification.

1-(Ethoxyethyl)-4-(4,4,5,5-tetramethyl[1,3,2]dioxaborolan-2-yl)-1H-pyrazole (24)

To a 100 ml solution of iPrMgCl.LiCl (50 mmol, 1.8 equiv) in THF was added 4-bromo-1-(ethoxyethyl)-1H-pyrazole (6.15 g, 28 mmol) at ambient temperature. The resulting reaction mixture was stirred at ambient temperature for 12 h and then cooled to −20° C. Methoxy pinacolborate (10.6 g, 67 mmol, 2.4 equiv) was then added to the reaction mixture at −20° C. The resulting mixture was stirred at 0-10° C. for 1 h. Aqueous $NH_4Cl$ was added to quench the reaction. The mixture was then extracted with petroleum ether (PE). The combined PE extracts were washed with saturated $NaHCO_3$, dried over $Na_2SO_4$ and concentrated under reduced pressure. The crude product was crystallized in PE to afford 1-(ethoxyethyl)-4-(4,4,5,5-tetramethyl[1,3,2]dioxaborolan-2-yl)-1H-pyrazole (24, 4.2 g, 7.45 g theoretical, 56.4% yield) as a white to off-white solid (GC purity: 99%). For 24: $^1H$ NMR (DMSO-$d_6$, 400 MHz) δ 8.09 (s, 1H), 8.58 (s, 1H), 7.62 (s, 1H), 5.55 (q, 1H, J=6.1 Hz), 3.37 (dq, 1H, J=7.1, 9.6 Hz), 3.12 (dq, 1H, J=7.0, 9.7 Hz), 1.56 (d, 3H, J=6.0 Hz), 1.24 (s, 12H), 1.00 (t, 3H, J=7.0 Hz) ppm; $C_{13}H_{23}BN_2O_3$ (MW, 266.14), LCMS (EI) m/e 267 ($M^+$+H).

4-(4,4,5,5-Tetramethyl-1,3,2-dioxaborolan-2-yl)-1H-pyrazole (1)

To a mixture of 2,3-dimethylbutane-2,3-diol (25.0 kg, 211.6 mol) and 1-(1-ethoxyethyl)-4-(4,4,5,5-tetramethyl-1, 3,2-dioxaborolan-2-yl)-1H-pyrazole (24, 55.0 kg, 206.7 mol) in 1,2-dichloroethane (750 kg) was slowly added a solution of HCl in MTBE (25.0 kg, 20-30% of HCl) at 0-5° C. The resulting reaction mixture was then stirred at 10-20° C. for 3-5 hours. After the selective deprotection reaction was complete as monitored by HPLC (1: below 1%), the reaction mixture was degassed and refilled with nitrogen before being cooled to −15° C. The cooled reaction mixture was then added triethylamine (TEA, 30.0 kg, 296.5 mol) to adjust pH to 7-8. The mixture was then gradually warmed to ambient temperature before being treated with water (150 kg). The two phases were separated and the organic layer was washed with brine (60 kg) and dried over sodium sulfate ($Na_2SO_4$). The drying reagent, sodium sulfate ($Na_2SO_4$), was removed by filtration and the resulting solution was concentrated under reduced pressure at 40-50° C. to a thick oil. The residue was warmed to 60-70° C. and diluted with petroleum ether (100 kg) at the same temperature. The resulting mixture was then gradually cooled to ambient temperature and subsequently to −5° C. and stirred at the same temperature for 3 hours. The solids was collected by centrifugation and dried at 50-60° C. under vacuum to afford the crude desired product (1, 33.75 kg, 40.11 kg theoretical, 84.1%). The crude desired product was then suspended in 1,2-dichloroethane (30 kg) and the resulting mixture was heated to reflux until a clear solution was formed. To the hot solution was then added petroleum ether (150 kg) at the same temperature. The resulting mixture was then gradually cooled to ambient temperature and subsequently to −5° C. and stirred and the same temperature for 3 hours. The solids were collected by centrifugation and dried under vacuum at 50-60° C. to afford 4-(4,4,5,5-tetramethyl-1,3,2-dioxaborolan-2-yl)-1H-pyrazole (1, 31.0 kg, 40.11 kg theoretical, 77.3%) as an off-white solid, which is identical in every comparable aspect to the material synthesized by the synthetic method as described above in Example 5.

Example 7

Synthesis of 4-Chloro-7H-[pyrrolo[2,3-d]pyrimidine

Scheme VII

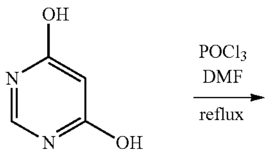

25

$C_4H_4N_2O_2$
Mol. Wt: 112.09

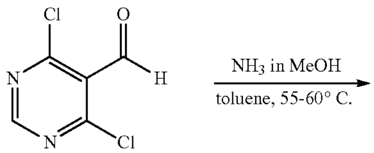

26

$C_5H_2Cl_2N_2O$
Mol. Wt: 176.99

-continued

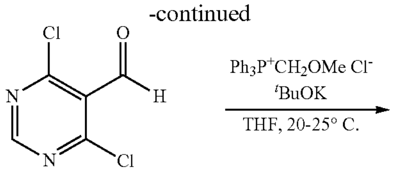

27

$C_5H_4ClN_3O$
Mol. Wt.: 153.57

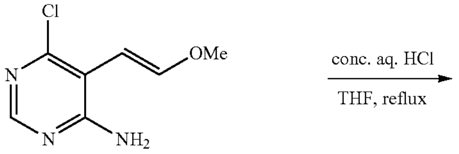

28

$C_7H_8ClN_3O$
Mol. Wt.: 185.61

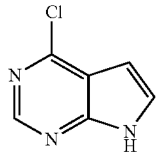

4

$C_6H_4ClN_3$
Mol. Wt.: 153.57

4,6-Dichloropyrimidine-5-carbaldehyde (26)

In a 5 L 4-neck flask equipped with a mechanical stirrer, an addition funnel, a condenser, a thermocouple, and a N2 sweep into an aqueous NaOH scrubbing solution, phosphorous oxychloride ($POCl_3$, 1 L, 10.572 mol, 4.82 equiv) was charged and cooled in an ice/salt bath. N,N-Dimethylformamide (DMF, 320 mL, 4.138 mol, 1.85 equiv) was then added dropwise to the flask at 0±2° C. After addition of approximately 100 mL of DMF over approximately 0.5 h, crystallization occurred and the reaction temperature was increased from 0 to 10° C. Addition was stopped and the mixture was allowed to re-cool to approximately 2° C. The remaining DMF was added over 2.5 h at below 8° C. The suspension became very thick making stirring difficult. When addition of DMF was complete, the mixture was stirred at 3-5° C. for 0.5 h. 4,6-Dihydroxypyrimidine (250 g, 2.232 mol) was added portion wise as a solid. After about one third of 4,6-dihydroxypyrimidine was added, the reaction mixture became more mobile, and a slow exothermic phenomena occurred with the reaction temperature increasing to approximately 12° C. over 0.5 h. The remaining 4,6-dihydroxypyrimidine was added portion wise over 0.25 h with the reaction temperature increasing from 12 to 27° C. The reaction temperature was maintained at 25-27° C. with intermittent cooling during which time the yellow suspension became thinner, then thicker once again. After the exothermic phenomenon subsided in about 1 h, the reaction mixture was heated slowly. At about 55° C. the reaction mixture became extremely thick and the second mild exothermic phenomenon was occurred. The heating mantle was removed while the reaction temperature continued to increase to about 63° C. and remained at this temperature for several minutes before dropping. Heating of the mixture was resumed until gentle reflux (about 100° C.) was attained. At about 95° C. a steady, fairly rapid evolution of HCl gas began and the reaction mixture gradually thinned and darkened. After about 0.5 h, a clear brown solution developed with the reflux temperature slowly increasing to 115° C. over 1.25 h. After a total of 2.5 h at reflux, the reaction mixture was cooled to ambient temperature and stirred overnight at ambient temperature. Excess amount of $POCl_3$ (as much as possible) was removed under reduced pressure (bath temperature 45-50° C.). The thick residual brown oil was poured very slowly into cold $H_2O$ (5 L) in a 20 L separation funnel, adding ice as needed to maintain the aqueous mixture near room temperature. The aqueous mixture was extracted with EtOAc (2×3 L followed by 1×2 L). The combined EtOAc extracts were washed with $H_2O$ (2×2.5 L), saturated $NaHCO_3$ aqueous solution (1 L), brine (1 L), dried over $Na_2SO_4$, filtered, and concentrated under reduced pressure (bath temperature at 35° C.) to afford the crude 4,6-dichloropyrimidine-5-carbaldehyde (270 g, 395 g theoretical, 68.4%) as yellow-orange solids. A 20 g portion of this crude material was purified by Kugelrohr distillation (oven temperature at 90-100° C., 225 mTorr) to give 15.3 g of pure 4,6-dichloropyrimidine-5-carbaldehyde as a white solid that turned yellow on standing at room temperature. $^1H$ NMR (300 MHz, $CDCl_3$) δ 10.46 (s, 1H), 8.89 (s, 1H) ppm.

4-Amino-6-chloropyrimidine-5-carbaldehyde (27)

A solution of 7 M $NH_3$ in MeOH (265 mL, 1.855 mol, 2.0 equiv) was added over 1.25 h to a solution of 4,6-dichloropyrimidine-5-carbaldehyde (163.7 g, 0.9301 mol) in toluene (3 L) at ambient temperature. The reaction temperature slowly increased from 20 to 26° C. and a yellow suspension formed. Mild cooling was applied to maintain the reaction temperature at below 26° C. The suspension was stirred at ambient temperature for 3.5 h before the solids were collected by filtration. The solids were washed with EtOAc (1 L). The filtrate was concentrated under reduced pressure, and the solids were triturated with toluene and n-heptane (2:1 v/v, 600 mL), filtered and dried to give 71.1 g of 4-amino-6-chloropyrimidine-5-carbaldehyde as a yellow solid. The original solid filtered from the reaction mixture contained additional amount of 4-amino-6-chloropyrimidine-5-carbaldehyde. The product was extracted from the filtered solid by stirring in EtOAc (1.25 L) for 1.5 h, filtering, then stirring in THF (750 mL) for 1 h and again filtering. Both EtOAc and THF filtrates were concentrated under reduced pressure, and the resulting solids were triturated with toluene and n-heptane (2:1 v/v, 450 mL), filtered and dried to give an additional 44.1 g of 4-amino-6-chloropyrimidine-5-carbaldehyde as a yellow solid. The combined yield of 4-amino-6-chloropyrimidine-5-carbaldehyde (115.2 g, 146.5 g theoretical) was 78.6%. $^1$HNMR (300 MHz, DMSO-$d_6$) δ 10.23 (s, 1H), 8.71 (bs, 1H), 8.55 (bs, 1H), 8.39 (s, 1H) ppm; $C_5H_4ClN_3O$ (MW, 157.56), LCMS (EI) m/e 158 ($M^+$+H).

6-Chloro-5-(2-methoxyvinyl)pyrimidin-4-ylamine (28)

A suspension of (methoxymethyl)triphenylphosphonium chloride (276.0 g, 0.807 mol, 1.1 equiv) in THF (1.5 L) was cooled in an ice/salt bath to −2° C. and 1 M potassium tert-butoxide (KOtBu) in THF (807 mL, 0.807 mol, 1.1 equiv) was added over 1.5 h at −2 to −3° C. The deep red-orange mixture was stirred at −2 to −3° C. for 1 h. 4-Amino-6-chloropyrimidine-5-carbaldehyde (115.2 g, 0.7338 mol, 1.0 equiv) was then added portion wise to the reaction mixture as a solid form using THF (200 mL) to rinse the container and funnel. During the addition the reaction temperature increased from −3 to 13° C. and a brown color developed. When the reaction temperature dropped to 10° C., the cooling bath was removed and the reaction mixture was allowed to warm to ambient temperature and stirred at ambient temperature for 42 h. The reaction mixture was cooled to −2° C. before being quenched by the slow addition of saturated $NH_4Cl$ aqueous solution (750 mL). The mixture was concentrated under reduced pressure to remove most of the THF. The residue was partitioned between EtOAc (3 L) and $H_2O$ (1 L). The organic phase was filtered to remove insoluble material at the interface, then extracted with 2 N HCl (4×250 mL) followed by 3 N HCl (2×250 mL). The combined HCl extracts were back-extracted with EtOAc (500 mL) then filtered through Celite to remove insoluble material. The filtrate was cooled in an ice/brine bath, adjusted to pH 8 with a 6 N aqueous NaOH solution and extracted with EtOAc (3×1 L). The combined EtOAc extracts were washed with brine (1 L), dried over $Na_2SO_4$, stirred with charcoal (10 g) and silica gel (10 g) for 1 h. The mixture was filtered through Celite, washing the Celite pad with EtOAc (1 L). The filtrate was concentrated, co-evaporating residual EtOAc with n-heptane (500 mL). The resulting tan solid was pumped under high vacuum for 2 h to afford crude 6-chloro-5-(2-methoxyvinyl)pyrimidin-4-ylamine (72.3 g, 136.2 g theoretical, 53.1%). The crude desired product was used in the following reaction without further purification. A sample of crude product (2.3 g) was purified by silica gel column chromatography on, eluting with 0-35% EtOAc/n-heptane to give 1.7 g of pure 6-chloro-5-(2-methoxyvinyl)pyrimidin-4-ylamine as a white solid, which was found to be a 1 to 2 mixture of E/Z isomers. $^1$H NMR (300 MHz, DMSO-$d_6$) for E-isomer: δ 8.02 (s, 1H), 7.08 (bs, 2H), 6.92 (d, 1H, J=13.1), 5.35 (d, 1H, J=13.0 Hz), 3.68 (s, 3H) ppm and for Z-isomer: δ 8.06 (s, 1H), 7.08 (bs, 2H), 6.37 (d, 1H, J=6.8 Hz), 5.02 (d, 1H, J=6.7 Hz), 3.69 (s, 3H) ppm; $C_7H_8ClN_3O$ (MW, 185.61), LCMS (EI) m/e 186/188 ($M^+$+H).

4-Chloro-7H-[pyrrolo[2,3-d]pyrimidine (4)

Concentrated HCl (5 mL) was added to a solution of crude 6-chloro-5-(2-methoxyvinyl)pyrimidin-4-ylamine (70.0 g, 0.3784 mol) in THF (700 mL) and the resulting reaction mixture was heated to reflux for 7.5 h. On warming a light suspension was formed that gradually re-dissolved. When the reaction was deemed complete as monitored by HPLC, the reaction mixture was cooled to ambient temperature and stirred at ambient temperature for overnight. Solid $NaHCO_3$ (15 g) was added to the reaction mixture and the resulting mixture was stirred at ambient temperature for 1 h. Charcoal (7 g), silica gel (7 g) and $Na_2SO_4$ (20 g) were added and the mixture was heated to 40° C. for 1 h. The mixture was then cooled to ambient temperature and filtered through Celite, washing the Celite pad with THF (1 L). The filtrate was concentrated under reduced pressure and the resulting solid was dried under reduced pressure to afford crude 4-chloro-7H-[pyrrolo[2,3-d]pyrimidine (4, 58.1 g, 58.1 g theoretical, 100%) as a yellow-brown solid. This crude desired product was dissolved in EtOAc (1 L) at 50-55° C. and treated with activated charcoal (3 g). The mixture was filtered while warm through Celite and the Celite pad was washed with warm EtOAc (250 mL). The filtrate was concentrated to about 500 mL and the suspension was allowed to stand at ambient temperature for overnight. The suspension was subsequently cooled to 0-5° C. for 2 h before the solids were collected by filtration. The solids were dried to afford pure 4-chloro-7H-[pyrrolo[2,3-d]pyrimidine (4, 54.5 g, 58.1 g theoretical, 94%) as yellow-brown crystals. $^1$H NMR (400 MHz, DMSO-$d_6$) δ

12.58 (bs, 1H), 8.58 (s, 1H), 7.69 (d, 1H, J=3.5 Hz), 6.59 (d, 1H, J=3.5 Hz) ppm; LCMS (EI) m/e 154/156 ($M^+$+H).

Example A

In Vitro JAK Kinase Assay

The compound of Formula I was tested for inhibitory activity of JAK targets according to the following in vitro assay described in Park et al., *Analytical Biochemistry* 1999, 269, 94-104. The catalytic domains of human JAK1 (a.a. 837-1142) and JAK2 (a.a. 828-1132) with an N-terminal His tag were expressed using baculovirus in insect cells and purified. The catalytic activity of JAK1 and JAK2 was assayed by measuring the phosphorylation of a biotinylated peptide. The phosphorylated peptide was detected by homogenous time resolved fluorescence (HTRF). $IC_{50}$s of compounds were measured for each kinase in the 40 microL reactions that contain the enzyme, ATP and 500 nM peptide in 50 mM Tris (pH 7.8) buffer with 100 mM NaCl, 5 mM DTT, and 0.1 mg/mL (0.01%) BSA. For the 1 mM $IC_{50}$ measurements, ATP concentration in the reactions was 1 mM. Reactions were carried out at room temperature for 1 hr and then stopped with 20 μL 45 mM EDTA, 300 nM SA-APC, 6 nM Eu-Py20 in assay buffer (Perkin Elmer, Boston, Mass.). Binding to the Europium labeled antibody took place for 40 minutes and HTRF signal was measured on a Fusion plate reader (Perkin Elmer, Boston, Mass.). The compound of Formula I and the adipic acid salt had an $IC_{50}$ at JAK1 of ≤5 nM (measured at 1 mM ATP) with a JAK2/JAK1 ratio of >10 (measured at 1 mM ATP).

Example B

Cellular Assays

Cancer cell lines dependent on cytokines and hence JAK/STAT signal transduction, for growth, can be plated at 6000 cells per well (96 well plate format) in RPMI 1640, 10% FBS, and 1 nG/mL of appropriate cytokine. Compounds can be added to the cells in DMSO/media (final concentration 0.2% DMSO) and incubated for 72 hours at 37° C., 5% $CO_2$. The effect of compound on cell viability is assessed using the CellTiter-Glo Luminescent Cell Viability Assay (Promega) followed by TopCount (Perkin Elmer, Boston, Mass.) quantitation. Potential off-target effects of compounds are measured in parallel using a non-JAK driven cell line with the same assay readout. All experiments are typically performed in duplicate.

The above cell lines can also be used to examine the effects of compounds on phosphorylation of JAK kinases or potential downstream substrates such as STAT proteins, Akt, Shp2, or Erk. These experiments can be performed following an overnight cytokine starvation, followed by a brief preincubation with compound (2 hours or less) and cytokine stimulation of approximately 1 hour or less. Proteins are then extracted from cells and analyzed by techniques familiar to those schooled in the art including Western blotting or ELISAs using antibodies that can differentiate between phosphorylated and total protein. These experiments can utilize normal or cancer cells to investigate the activity of compounds on tumor cell survival biology or on mediators of inflammatory disease. For example, with regards to the latter, cytokines such as IL-6, IL-12, IL-23, or IFN can be used to stimulate JAK activation resulting in phosphorylation of STAT protein(s) and potentially in transcriptional profiles (assessed by array or qPCR technology) or production and/or secretion of proteins, such as IL-17. The ability of compounds to inhibit these cytokine mediated effects can be measured using techniques common to those schooled in the art.

Compounds herein can also be tested in cellular models designed to evaluate their potency and activity against mutant JAKs, for example, the JAK2V617F mutation found in myeloid proliferative disorders. These experiments often utilize cytokine dependent cells of hematological lineage (e.g. BaF/3) into which the wild-type or mutant JAK kinases are ectopically expressed (James, C., et al. *Nature* 434:1144-1148; Staerk, J., et al. JBC 280:41893-41899). Endpoints include the effects of compounds on cell survival, proliferation, and phosphorylated JAK, STAT, Akt, or Erk proteins.

Certain compounds herein can be evaluated for their activity inhibiting T-cell proliferation. Such as assay can be considered a second cytokine (i.e. JAK) driven proliferation assay and also a simplistic assay of immune suppression or inhibition of immune activation. The following is a brief outline of how such experiments can be performed. Peripheral blood mononuclear cells (PBMCs) are prepared from human whole blood samples using Ficoll Hypaque separation method and T-cells (fraction 2000) can be obtained from PBMCs by elutriation. Freshly isolated human T-cells can be maintained in culture medium (RPMI 1640 supplemented with 10% fetal bovine serum, 100 U/ml penicillin, 100 μg/ml streptomycin) at a density of $2\times10^6$ cells/ml at 37° C. for up to 2 days. For IL-2 stimulated cell proliferation analysis, T-cells are first treated with Phytohemagglutinin (PHA) at a final concentration of 10 μg/mL for 72 h. After washing once with PBS, 6000 cells/well are plated in 96-well plates and treated with compounds at different concentrations in the culture medium in the presence of 100 U/mL human IL-2 (ProSpec-Tany TechnoGene; Rehovot, Israel). The plates are incubated at 37° C. for 72 h and the proliferation index is assessed using CellTiter-Glo Luminescent reagents following the manufactory suggested protocol (Promega; Madison, Wis.).

Example C

In Vivo Anti-Tumor Efficacy

Compounds herein can be evaluated in human tumor xenograft models in immune compromised mice. For example, a tumorigenic variant of the INA-6 plasmacytoma cell line can be used to inoculate SCID mice subcutaneously (Burger, R., et al. *Hematol J.* 2:42-53, 2001). Tumor bearing animals can then be randomized into drug or vehicle treatment groups and different doses of compounds can be administered by any number of the usual routes including oral, i.p., or continuous infusion using implantable pumps. Tumor growth is followed over time using calipers. Further, tumor samples can be harvested at any time after the initiation of treatment for analysis as described above (Example B) to evaluate compound effects on JAK activity and downstream signaling pathways. In addition, selectivity of the compound(s) can be assessed using xenograft tumor models that are driven by other know kinases (e.g. Bcr-Abl) such as the K562 tumor model.

Example D

Murine Skin Contact Delayed Hypersensitivity Response Test

Compounds herein can also be tested for their efficacies (of inhibiting JAK targets) in the T-cell driven murine delayed hypersensitivity test model. The murine skin contact delayed-type hypersensitivity (DTH) response is considered to be a valid model of clinical contact dermatitis, and other T-lymphocyte mediated immune disorders of the skin, such as psoriasis (*Immunol Today*. 1998 January; 19(1):37-44). Murine DTH shares multiple characteristics with psoriasis, including the immune infiltrate, the accompanying increase in inflammatory cytokines, and keratinocyte hyperproliferation. Furthermore, many classes of agents that are efficacious in treating psoriasis in the clinic are also effective inhibitors of the DTH response in mice (Agents Actions. 1993 January; 38(1-2):116-21).

On Day 0 and 1, Balb/c mice are sensitized with a topical application, to their shaved abdomen with the antigen 2,4, dinitro-fluorobenzene (DNFB). On day 5, ears are measured for thickness using an engineer's micrometer. This measurement is recorded and used as a baseline. Both of the animals' ears are then challenged by a topical application of DNFB in a total of 200 μL (10 μL on the internal pinna and 10 μL on the external pinna) at a concentration of 0.2%. Twenty-four to seventy-two hours after the challenge, ears are measured again. Treatment with the test compounds is given throughout the sensitization and challenge phases (day −1 to day 7) or prior to and throughout the challenge phase (usually afternoon of day 4 to day 7). Treatment of the test compounds (in different concentration) is administered either systemically or topically (topical application of the treatment to the ears). Efficacies of the test compounds are indicated by a reduction in ear swelling comparing to the situation without the treatment. Compounds causing a reduction of 20% or more were considered efficacious. In some experiments, the mice are challenged but not sensitized (negative control).

The inhibitive effect (inhibiting activation of the JAK-STAT pathways) of the test compounds can be confirmed by immunohistochemical analysis. Activation of the JAK-STAT pathway(s) results in the formation and translocation of functional transcription factors. Further, the influx of immune cells and the increased proliferation of keratinocytes should also provide unique expression profile changes in the ear that can be investigated and quantified. Formalin fixed and paraffin embedded ear sections (harvested after the challenge phase in the DTH model) are subjected to immunohistochemical analysis using an antibody that specifically interacts with phosphorylated STAT3 (clone 58E12, Cell Signaling Technologies). The mouse ears are treated with test compounds, vehicle, or dexamethasone (a clinically efficacious treatment for psoriasis), or without any treatment, in the DTH model for comparisons. Test compounds and the dexamethasone can produce similar transcriptional changes both qualitatively and quantitatively, and both the test compounds and dexamethasone can reduce the number of infiltrating cells. Both systemically and topical administration of the test compounds can produce inhibitive effects, i.e., reduction in the number of infiltrating cells and inhibition of the transcriptional changes.

Example E

In Vivo Anti-Inflammatory Activity

Compounds herein can be evaluated in rodent or non-rodent models designed to replicate a single or complex inflammation response. For instance, rodent models of arthritis can be used to evaluate the therapeutic potential of compounds dosed preventatively or therapeutically. These models include but are not limited to mouse or rat collagen-induced arthritis, rat adjuvant-induced arthritis, and collagen antibody-induced arthritis. Autoimmune diseases including, but not limited to, multiple sclerosis, type I-diabetes mellitus, uveoretinitis, thyroditis, myasthenia gravis, immunoglobulin nephropathies, myocarditis, airway sensitization (asthma), lupus, or colitis may also be used to evaluate the therapeutic potential of compounds herein. These models are well established in the research community and are familiar to those schooled in the art (Current Protocols in Immunology, Vol 3., Coligan, J. E. et al, Wiley Press.; *Methods in Molecular Biology*: Vol. 225, Inflammation Protocols., Winyard, P. G. and Willoughby, D. A., Humana Press, 2003.).

Example F

Animal Models for the Treatment of Dry Eye, Uveitis, and Conjunctivitis

Agents may be evaluated in one or more preclinical models of dry eye known to those schooled in the art including, but not limited to, the rabbit concanavalin A (ConA) lacrimal gland model, the scopolamine mouse model (subcutaneous or transdermal), the Botulinumn mouse lacrimal gland model, or any of a number of spontaneous rodent auto-immune models that result in ocular gland dysfunction (e.g. NOD-SCID, MRL/lpr, or NZB/NZW) (Barabino et al., Experimental Eye Research 2004, 79, 613-621 and Schrader et al., Developmental Opthalmology, Karger 2008, 41, 298-312, each of which is incorporated herein by reference in its entirety). Endpoints in these models may include histopathology of the ocular glands and eye (cornea, etc.) and possibly the classic Schirmer test or modified versions thereof (Barabino et al.) which measure tear production. Activity may be assessed by dosing via multiple routes of administration (e.g. systemic or topical) which may begin prior to or after measurable disease exists.

Agents may be evaluated in one or more preclinical models of uveitis known to those schooled in the art. These include, but are not limited to, models of experimental autoimmune uveitis (EAU) and endotoxin induced uveitis (EIU). EAU experiments may be performed in the rabbit, rat, or mouse and may involve passive or activate immunization. For instance, any of a number or retinal antigens may be used to sensitize animals to a relevant immunogen after which animals may be challenged ocuarly with the same antigen. The EIU model is more acute and involves local or systemic administration of lipopolysaccharide at sublethal doses. Endpoints for both the EIU and EAU models may include fundoscopic exam, histopathology amongst others. These models are reviewed by Smith et al. (Immunology and Cell Biology 1998, 76, 497-512, which is incorporated herein by reference in its entirety). Activity is assessed by dosing via multiple routes of administration (e.g. systemic or topical) which may begin prior to or after measurable disease exists. Some models listed above may also develop scleritis/episcleritis, chorioditis, cyclitis, or iritis and are therefore useful in investigating the potential activity of compounds for the therapeutic treatment of these diseases.

Agents may also be evaluated in one or more preclinical models of conjunctivitis known those schooled in the art. These include, but are not limited to, rodent models utilizing guinea-pig, rat, or mouse. The guinea-pig models include those utilizing active or passive immunization and/or immune challenge protocols with antigens such as ovalbumin or ragweed (reviewed in Groneberg, D. A., et al., Allergy 2003, 58, 1101-1113, which is incorporated herein by reference in its entirety). Rat and mouse models are similar in general design to those in the guinea-pig (also reviewed by Groneberg). Activity may be assessed by dosing via multiple routes of administration (e.g. systemic or topical) which may begin prior to or after measurable disease exists. Endpoints for such studies may include, for example, histological, immunological, biochemical, or molecular analysis of ocular tissues such as the conjunctiva.

Example G

In Vivo Protection of Bone

Compounds may be evaluated in various preclinical models of osteopenia, osteoporosis, or bone resorption known to those schooled in the art. For example, ovariectomized rodents may be used to evaluate the ability of compounds to affect signs and markers of bone remodeling and/or density (W. S. S. Jee and W. Yao, J Musculoskel. Nueron. Interact., 2001, 1(3), 193-207, which is incorporated herein by reference in its entirety). Alternatively, bone density and architecture may be evaluated in control or compound treated rodents in models of therapy (e.g. glucocorticoid) induced osteopenia (Yao, et al. Arthritis and Rheumatism, 2008, 58(6), 3485-3497; and id. 58(11), 1674-1686, both of which are incorporated herein by reference in its entirety). In addition, the effects of compounds on bone resorption and density may be evaluable in the rodent models of arthritis discussed above (Example E). Endpoints for all these models may vary but often include histological and radiological assessments as well as immunohisotology and appropriate biochemical markers of bone remodeling.

A number of embodiments of the invention have been described. Nevertheless, it will be understood that various modifications may be made without departing from the spirit and scope of the invention. Accordingly, other embodiments are within the scope of the following claims.

What is claimed is:

1. A compound of Formula VII:

VII

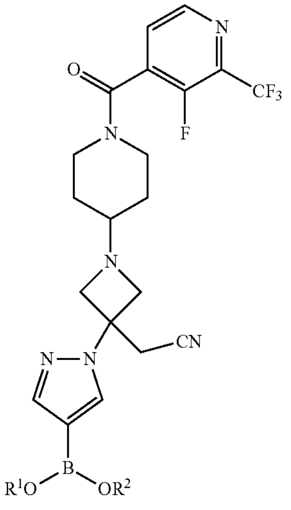

or a salt thereof; wherein:

$R^1$ and $R^2$ are each independently H or $C_{1-6}$ alkyl; or $R^1$ and $R^2$, together with the two oxygen atoms to which they are attached and the boron atom to which the oxygen atoms are attached, form a 5- to 6-membered heterocycloalkyl ring, which is optionally substituted with 1, 2, 3, or 4 $C_{1-4}$ alkyl groups.

2. The compound of claim 1, having Formula VIIa:

VIIa

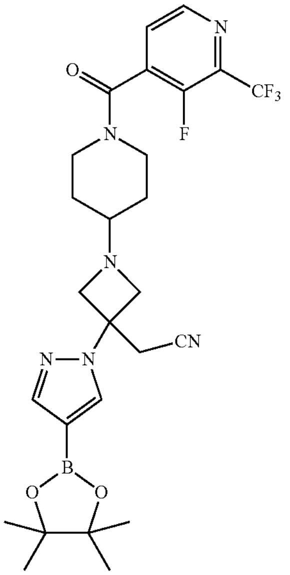

or a salt thereof.

3. A process, comprising:

reacting a compound of Formula VIII:

VIII

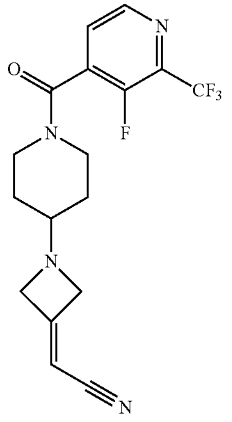

with a compound of Formula IX:

IX

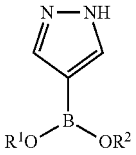

in the presence of a coupling agent to form a compound of claim 1; wherein:

$R^1$ and $R^2$ are each independently H or $C_{1-6}$ alkyl; or $R^1$ and $R^2$, together with the two oxygen atoms to which they are attached and the boron atom to which the oxygen atoms are attached, form a 5- to 6-membered heterocycloalkyl ring, which is optionally substituted with 1, 2, 3, or 4 $C_{1-4}$ alkyl groups.

4. The process according to claim 3, wherein the coupling agent is 1,8-diazabicyclo[5,4,0]undecene.

5. The process according to claim 4, wherein 1.05 to about 1.2 equivalents of coupling agent is used based on the compound of Formula VIII.

6. The process according to claim 5, wherein the reacting of the compound of Formula VIII with the compound of Formula IX is conducted in a solvent component comprising acetonitrile.

7. The process according to claim 5, wherein the reacting of the compound of Formula VIII with the compound of Formula IX is conducted in a solvent component comprising acetonitrile at a temperature of about 40° C. to about 60° C.

8. The process according to claim 7, wherein 1 to 1.2 equivalents of the compound of Formula IX are used based on the compound of Formula VIII.

9. The process according to claim 3, wherein the process comprises reacting a compound of Formula VIII:

VIII

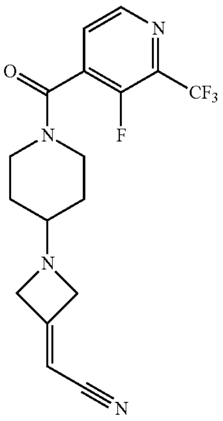

with a compound of Formula IXa:

IXa

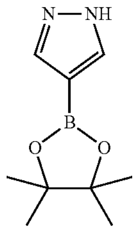

in the presence of a coupling agent to form a compound of Formula VIIa:

VIIa

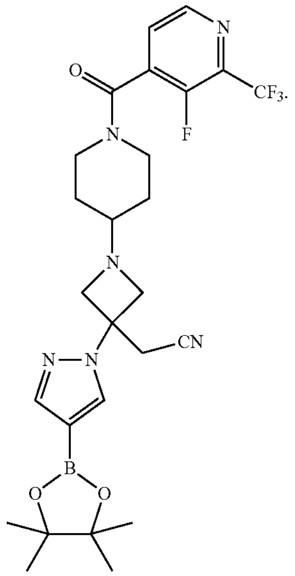

10. The process according to claim 9, wherein the coupling agent is 1,8-diazabicyclo[5,4,0]undecene.

11. The process according to claim 10, wherein 1.05 to about 1.2 equivalents of coupling agent is used based on the compound of Formula VIII.

12. The process according to claim 11, wherein the reacting of the compound of Formula VIII with the compound of Formula IXa is conducted in a solvent component comprising acetonitrile.

13. The process according to claim 10, wherein the reacting of the compound of Formula VIII with the compound of Formula IXa is conducted in a solvent component comprising acetonitrile at a temperature of about 40° C. to about 60° C.

14. The process according to claim 13, wherein 1 to 1.2 equivalents of the compound of Formula IXa are used based on the compound of Formula VIII.

15. The process according to claim 9, further comprising reacting the compound of Formula VIIa with a compound of Formula IVa:

IVa

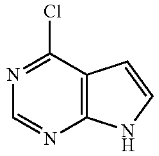

under Suzuki coupling conditions to form a compound of Formula I:

I

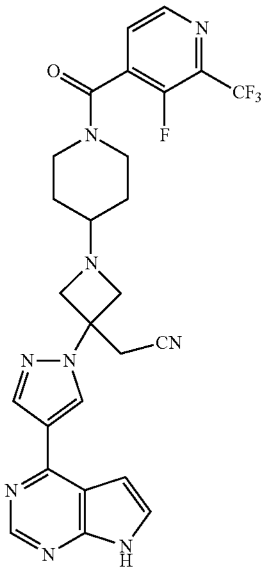

wherein the Suzuki coupling conditions comprise heating a reaction mixture comprising the compound of Formula VIIa, the compound of Formula IVa, a Suzuki coupling catalyst, a base and a second solvent component.

16. The process according to claim 15, wherein the catalyst is tetrakis(triphenylphosphine)palladium(0).

17. The process according to claim 16, wherein the base is sodium bicarbonate.

18. The process according to claim 17, wherein the sodium bicarbonate is present in 4 equivalents or more based on the compound of Formula VIIa.

19. The process according to claim 18, wherein the second solvent component comprises 1,4-dioxane and water.

20. The process according to claim 19, wherein the 1,4-dioxane and water are present in a 1:1 volume ratio.

21. The process according to claim 20, wherein the compounds of Formula VIIa and IVa are present in about a 1:1 molar ratio.

22. The process according to claim 9, further comprising reacting the compound of Formula VIIa with a compound of Formula IVa:

IVa

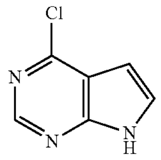

under Suzuki coupling conditions to form a compound of Formula I:

I

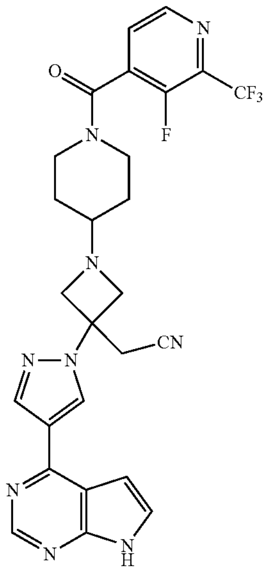

wherein the Suzuki coupling conditions comprise heating a reaction mixture comprising the compound of Formula VIIa, the compound of Formula IVa, tetrakis(triphenylphosphine)palladium(0), sodium bicarbonate, and a second solvent component, wherein the second solvent component comprises water and 1,4-dioxane.

23. A compound of Formula VIII:

VII

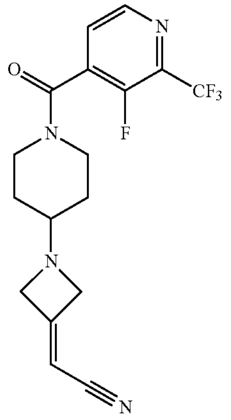

or a salt thereof.

24. A process of preparing a compound of claim 23, or a salt thereof, comprising reacting a compound of Formula VI:

VI

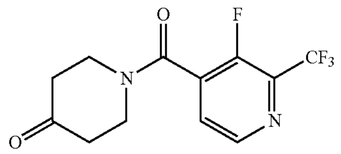

with a compound of Formula X:

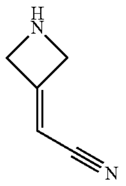

X or a salt thereof, in the presence of a reducing agent.

25. The process according to claim 24, wherein the compound of Formula X, or salt thereof, is 2-(azetidin-3-ylidene) acetonitrile hydrochloride.

26. The process according to claim 25, wherein the reducing agent is sodium cyanoborohydride or sodium triacetoxyborohydride.

27. The process according to claim 25, wherein the reducing agent is sodium triacetoxyborohydride.

28. The process according to claim 27, wherein about 1.5 to about 2.5 equivalents of the reducing agent are used based on the compound of Formula X, or salt thereof.

29. The process according to claim 27, wherein about 2 equivalents of the reducing agent are used based on the compound of Formula X, or salt thereof.

30. The process according to claim 28, wherein the reacting of the compound of Formula VI and the compound of Formula X, or salt thereof, are conducted in a solvent component comprising dichloromethane.

* * * * *